(12) United States Patent
Sirizzotti et al.

(10) Patent No.: US 11,072,800 B2
(45) Date of Patent: Jul. 27, 2021

(54) PARTHENOCARPIC WATERMELON PLANTS

(71) Applicant: NUNHEMS B.V., Nunhem (NL)

(72) Inventors: Alberto Sirizzotti, Sant'Agata Bolognese (IT); Richard Bernard Berentsen, Zutphen (NL); Hendrik Willem Vriezen, Haelen (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 16/338,262

(22) PCT Filed: Sep. 29, 2017

(86) PCT No.: PCT/EP2017/074809
§ 371 (c)(1),
(2) Date: Mar. 29, 2019

(87) PCT Pub. No.: WO2018/060444
PCT Pub. Date: Apr. 5, 2018

(65) Prior Publication Data
US 2019/0300900 A1    Oct. 3, 2019

(30) Foreign Application Priority Data
Sep. 30, 2016 (EP) .................................. 16191903

(51) Int. Cl.
*C12N 15/82* (2006.01)
*A01H 5/08* (2018.01)
*A01H 6/32* (2018.01)
*A01H 1/06* (2006.01)
*C07K 14/415* (2006.01)

(52) U.S. Cl.
CPC .......... *C12N 15/8287* (2013.01); *A01H 1/06* (2013.01); *A01H 5/08* (2013.01); *A01H 6/324* (2018.05); *C07K 14/415* (2013.01); *C12N 15/8213* (2013.01)

(58) Field of Classification Search
None
See application file for complete search history.

(56) References Cited

U.S. PATENT DOCUMENTS

2017/0335339 A1* 11/2017 Van Dun ............ C12N 15/8294

FOREIGN PATENT DOCUMENTS

| EP | 2959771 A1 | 12/2015 |
|---|---|---|
| EP | 3464333 A1 | 4/2019 |
| WO | 2012069539 A1 | 5/2012 |
| WO | 2016120438 A1 | 8/2016 |

OTHER PUBLICATIONS

Margulis. Biodiversity: molecular biological domains, symbiosis and kingdom origins. Biosystems. 1992;27(1):39-51. (Year: 1992).*
Sjolander. Phylogenomic inference of protein molecular function: advances and challenges. Bioinformatics. Jan. 22, 2004;20(2):170-9. (Year: 2004).*
Rhoads D.M. et al. Regulation of the cyanide-resistant alternative oxidase of plant mitochondria. Identification of the cysteine residue involved in alpha-keto acid stimulation and intersubunit disulfide bond formation. J Biol Chem. Nov. 13, 1998;273(46):30750-6. (Year: 1998).*
Lamberg A. et al. Site-directed mutagenesis of the alpha subunit of human prolyl 4-hydroxylase. Identification of three histidine residues critical for catalytic activity. J Biol Chem. Apr. 28, 1995;270(17):9926-31. (Year: 1995).*
Hill M.A. et al Functional analysis of conserved histidines in ADP-glucose pyrophosphorylase from *Escherichia coli*. Biochem Biophys Res Commun. Mar. 17, 1998;244(2):573-7. (Year: 1998).*
Doerks T. et al. Protein annotation: detective work for function prediction. Trends Genet. Jun. 1998;14(6):248-50. (Year: 1998).*
Whisstock J.C. et al. Prediction of protein function from protein sequence and structure. Q Rev Biophys. Aug. 2003;36(3):307-40. Review. (Year: 2003).*
Rose et al. The tomato 1-box binding factor LeMYBI is a member of a novel class of myb-like proteins. Plant J. Dec. 1999;20(6):641-52. (Year: 1999).*
Rubio-Somoza et al. Ternary complex formation between HvMYBS3 and other factors involved in transcriptional control in barley seeds. Plant J. Jul. 2006;47(2):269-81. Epub Jun. 7, 2006. (Year: 2006).*
Acciarri, et al., "Genetically modified parthenocarpic eggplants: improved fruit productivity under both greenhouse and open field cultivation", BMC Biotechnology, vol. 2, Issue 4, 2002, pp. 1-7.
Allen, et al., "Transcript-specific, single-nucleotide polymorphism discovery and linkage analysis in hexaploid bread wheat (*Triticum aestivum* L.)", Plant Biotechnology Journal, vol. 9, Issue 9, Dec. 2011, pp. 1086-1099.
Database Cucurbit Genomics [Online], "Cla012091 (gene) Watermelon (97103)", XP002776414, Database accession No. Cla012091, 2017, 6 pages.
Database UniProt [Online], "SubName: Full=Uncharacterized protein{EC0:0000313:EMBL:KGN54684.1}", XP002776413, Jan. 7, 2015, EBI accession No. UNIPROT:A0A0A0L0V3, Database accession No. A0A0A0L0V3, 2 page.
Guner, et al., "The Genes of Watermelon", HortScience, vol. 39, Issue 6, 2004, pp. 1175-1182.
Guo, et al., "The draft genome of watermelon (*Citrullus lanatus*) and resequencing of 20 diverse accessions", Nature Genetics, vol. 45, 2013, pp. 51-58.
Henikoff, et al., "Amino acid substitution matrices from protein blocks", Proceedings of the National Academy of Sciences of the United States of America, vol. 89, Issue 22, 1992, pp. 10915-10919.
Hitoshi Kihara , "Triploid watermelons", Proceedings of the American Society for Horticultural Science, vol. 58, 1951, pp. 217-230.
International Search Report for PCT Patent Application No. PCT/EP2017/074809, dated Jan. 10, 2018, 5 pages.

(Continued)

*Primary Examiner* — Cynthia E Collins
(74) *Attorney, Agent, or Firm* — Arent Fox LLP

(57) ABSTRACT

The present invention is directed to seedless fruit producing watermelon plants. The present invention also comprises methods for production of said plants and methods for producing seedless watermelon fruits.

17 Claims, 3 Drawing Sheets

Figure 1:
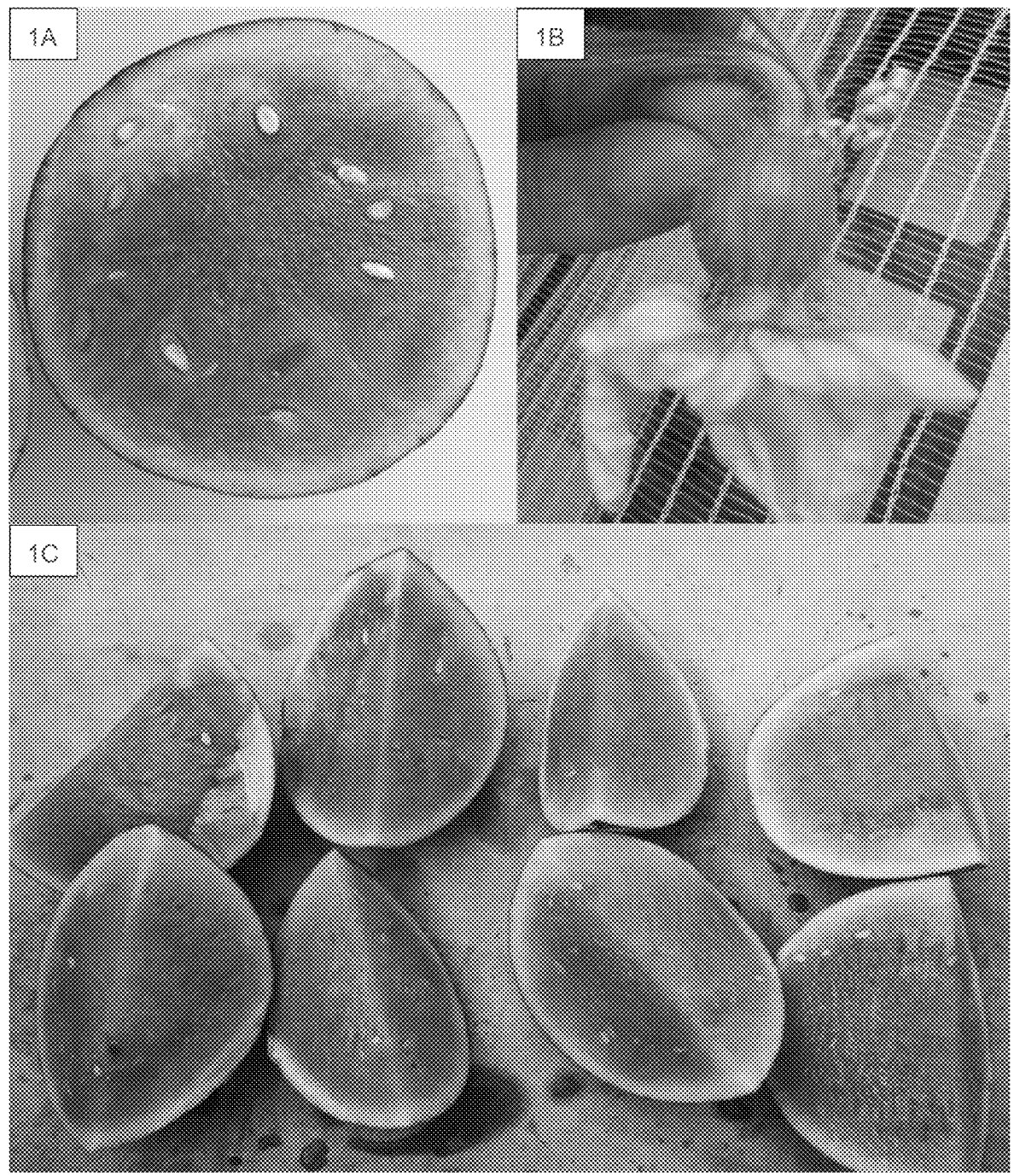

Specification includes a Sequence Listing.

(56) References Cited

OTHER PUBLICATIONS

Moussa, et al., "Parthenocarpy of watermelon cultivars induced by γ-irradiation", Russian Journal of Plant Physiology, vol. 57, Issue 4, Jul. 2010, pp. 574-581.

Ng, et al., "SIFT: predicting amino acid changes that affect protein function", Nucleic Acids Research, vol. 31, Issue 13, Jul. 2003, pp. 3812-3814.

Noh, et al., "Screening different methods of tetraploid induction in watermelon [*Citrullus lanatus* (thunb.) Manst. and Nakai]", Horticulture, Environment, and Biotechnology, vol. 53, Issue 6, Dec. 2012, pp. 521-529.

Oj Eigsti, et al., "About our cover", HortScience, vol. 6, 1971, 1 page.

Ren, et al., "A High Resolution Genetic Map Anchoring Scaffolds of the Sequenced Watermelon Genome", PLOS ONE, vol. 7, Issue 1, Jan. 2012, pp. e29453 (1-10).

Rotino, et al., "Open field trial of genetically modified parthenocarpic tomato: seedlessness and fruit quality", BMC Biotechnology, vol. 5, Issue 32, 2005, pp. 1-8.

Ruan, et al., "Molecular regulation of seed and fruit set", Trends in Plant Science, vol. 17, Issue 11, Nov. 2012, pp. 656-665.

Sari, et al., "Comparison of ploidy level screening methods in watermelon: Citrullus lanatus (Thunb.) Matsum. and Nakai", Scientia Horticulturae, vol. 82, Issue 3-4, Dec. 23, 1990, pp. 265-277.

Sugiyama, et al., "New Method of Producing Diploid Seedless Watermelon Fruit", Japan Agricultural Research Quarterly: JARQ, vol. 36, Issue 3, 2002, pp. 177-182.

Yin, et al., "The DefH9-iaaM-containing construct efficiently induces parthenocarpy in cucumber", Cellular & Molecular Biology Letters, vol. 11, Issue 24, 2006, pp. 279-290.

Zhang, et al., "Characteristics of a novel male-female sterile watermelon (*Citrullus lanatus*) mutant", Scientia Horticulturae, vol. 140, Jun. 1, 2012, pp. 107-114.

Zhang, et al., "Development of Genic Male-sterile Watermelon Lines with Delayed-green Seedling Marker", HortScience, vol. 31, Issue 1, 1996, pp. 123-126.

\* cited by examiner

PARTHENOCARPIC WATERMELON PLANTS

CROSS-REFERENCE TO RELATED APPLICATIONS

This application is a 35 U.S.C. 371 National Phase of PCT Application No. PCT/EP2017/074809, filed on Sep. 29, 2017, which claims priority to EP Application No. 16191903.0 filed Sep. 30, 2016, the disclosure of which is hereby incorporated by reference in its entirety.

FIELD

The present invention is directed to facultative parthenocarpic watermelon plants, producing seedless fruits without pollination of the female flowers, due to the presence of a mutant allele of a recessive gene referred to as WOP1 (for WithOutPapa 1). The present invention also comprises methods for production of said plants and the use of the mutant allele, referred to as wop1, for the production of seedless watermelon fruits. The invention also relates to other facultative parthenocarpic plants, such as cucumber and melon.

BACKGROUND

Most commercial seedless fruits have been developed from plants whose fruits normally contain numerous relatively large hard seeds distributed throughout the flesh of the fruit. Seedless fruits are e.g. known for watermelon, tomato, cucumber, eggplant, grapes, banana, citrus fruits, such as orange, lemon and lime. As consumption of seedless fruits is generally easier and more convenient, they are considered valuable.

Fruit development normally begins when one or more egg cells in the ovular compartment of the flower are fertilized by sperm nuclei from pollen.

Seedless fruits can result from two different phenomena. In some cases fruit develops without fertilization of the ovule by pollen, a phenomenon known as parthenocarpy. In other cases seedless fruits occur after pollination when seed (embryo and/or endosperm) growth is inhibited or the seed dies early, while the remainder of the fruit continues to grow (stenospermocarpy). In contrast to parthenocarpy, stenospermocarpy requires pollination for initiation of fruit growth.

Seedless orange fruits are an example for parthenocarpy. Some orange varieties (e.g. Navel) do not produce viable pollen. They however can be cross-pollinated with pollen from other varieties. In case only the male sterile variety is grown in an orchard, there will be no pollination and parthenocarp seedless fruits will be produced. Propagation of the respective orange trees is commonly done by cuttings followed by grafting to another rootstock.

Seedless bananas are triploid. Although pollination in some cases can be normal the vast majority of fruits is seedless. This is explained by the uneven sets of chromosomes (3×) leading to improper division of chromosomes during meiosis and as a consequence to the production of non-viable pollen. Without fertilization, triploid bananas are also able to set and develop seedless fruits. Even when pollination takes place, at most one in three hundred fruits comprises a few seeds. This may be due to the triploid pollen being non-viable, for the reasons explained. Therefore, banana plants can in general be seen to be parthenocarpic. Banana plants are commonly propagated asexually from side shoots or suckers at the base of the main stalk, which can be removed and replanted to continue the cultivar. Growers also propagate bananas by means of tissue culture, in particular for producing disease free material.

Seedless cucumber, seedless squash and seedless eggplant are examples for crops which can produce seedless fruits without pollination (parthenocarpy), e.g. under conditions where pollination is impaired (e.g. low temperatures). Nevertheless, commercial quality fruit can be produced under these conditions. All these crops however can produce seed bearing fruits upon pollination. Therefore, these crops are facultative parthenocarpic. Propagation of the crops can be done by self- or cross pollination, in vitro propagation, and grafting.

From tomato mutants it is also known that they can produce seedless fruits under conditions where normal pollination/fertilization is impaired (e.g. under circumstances of low temperature). Thus, these mutants are also facultative parthenocarpic. Mutants known for showing this phenotype are pat, pat-2 and the pat-3/pat-4 system. The genes underlying these mutations are not known and the pat-3/pat-4 system seems to depend on multiple loci.

Parthenocarpy has also been introduced into several plant species by means of genetic modification. Expression of a bacterial tryptophan monooxygenase (iaaM) conferring auxin synthesis under control of the ovule and placenta specific DefH9 promoter did induce parthenocarpy in cucumbers (Yin et al., 2006, Clular & molecular Biotech. Letters 11, 279-290), eggplant (Acciarri et al., 2002, BMC Biotech. 2(4)), tomato (Rotino et al., 2005, BMC Biotech. 5(32)) and tobacco.

These transgenic plants demonstrate the importance of plant hormones in seed and fruit development. That seed and fruit development are besides other factors strongly under control of several plant hormones is well known in the art. Parthenocarpy, including the logical consequence of fruit's seedlessness, can also be induced e.g. by exogenous application of plant hormones, in particular auxin or gibberellin (Ruan et al., Trends in Plant Sci. 17(11), 1360-1385).

Seedless watermelons produced currently by breeders are examples for stenospermocarp crops. Normal watermelon plants are diploid (2n). Seedless fruit producing watermelons are hybrids produced by crossing a male diploid (2n) watermelon plant with a female tetraploid (4n) watermelon plant. The resulting F1 hybrid seeds are triploid (3n). Induction of fruit setting of the triploid F1 hybrid plants requires pollination. As the triploid (3n) F1 hybrid plants do not produce fertile pollen, so called pollinator or polliniser plants have to be planted in the same field. The pollinator plants are diploid (2n). Generally a ratio of pollinator to hybrid plants of around 1 to 3 must be planted in a given scheme for providing sufficient pollen for pollinating all the F1 hybrid plants. The cross-pollination between the diploid (2n) pollinator and the flowers of the female triploid (3n) hybrid plant induces fruit set and leads to the production of seedless triploid fruits on the triploid hybrid plant. The diploid (2n) and tetraploid (4n) parents of the F1 hybrid each produce seed bearing fruits and can both be propagated independently from each other by self-pollination.

Seedless grapes can be produced from plants being either parthenocarp or stenospermocarp. The variety Black Corinth is parthenocarp, whereas Sultanina is stenospermocarp. Vine plants are in general propagated by cuttings and successive grafting to another rootstock.

Irregularities in meiosis can be a factor leading to plants producing seedless fruit. An example for plants producing seedless fruits is given in Zhang et al. (2012, Scientia Horticulture 140, 107-114), disclosing seedless watermelons. A male and female sterile (MFS) mutant was obtained from the progeny of a F1-hybrid after irradiation of its seeds with gamma-rays. Pollen from the MFS mutant was not viable at all. Seedless fruits are produced by the MFS plants, when pollinated with pollen from male fertile plants. The MFS watermelon plant therefore can be classified as being stenospermocarpic. Ovules were also nearly entirely non-viable, as almost no seeds were produced upon cross-pollination of MFS mutants with pollen from different male fertile plants. Incomplete synapsis and abnormal separation of chromatids during meiosis were observed in the MFS mutant and seen to be the cause of male and female sterility. The genes responsible for the effects present in the MFS mutant have not been identified but it seems likely that the phenotype in the MFS mutant is due to a single recessive gene.

From above discussion it is evident, that the factors determining if plants produce seedless fruits are multiple in nature and can reside in several, e.g. morphologic, physiologic and/or genetic causes.

For producing seedless fruits in stenospermocarpic crops, such as triploid (3n) watermelon plants, a female flower part of a plant must be pollinated. The stenospermocarpic crops grown today are male sterile. As a consequence, besides the female plant, a different male fertile plant (pollinator or polliniser) has to be grown in addition in the same field. As the area used for the pollinator plants is at the expense of the area which is available for the seedless fruit producing female plants, the yield per area under cultivation is reduced. In general, the pollinator plants are normal plants which can also be self-pollinated. Fruits produced by pollinator plants however do produce seeds. In watermelon, the pollinator plants are normally diploid (2n), which upon self-pollination produce seeded fruits, which may in some instances also be harvested and sold separately (see WO2012069539). For commercial reasons these seeded fruits from the pollinator plants must not be mixed with the seedless fruits. Therefore, it has to be ensured, that seedless fruits and seeded fruits are separated upon or after harvest, which may make machine harvesting difficult or impossible or require a further processing step after harvesting. Those additional precautions to be taken increase the input costs in seedless fruit production. In addition, pollinator plants are developed so that they flower and produce sufficient viable pollen at the same time the female plant flowers and its stigma can accept pollen for the induction of fruit set. Thus, the pollinator plant has to fit with the female plant producing seedless fruit in respect to flowering and fertilisation time. If flowering time of the pollinator pant and the respective female plant is not sufficiently synchronised, pollination will not take place or only take place in an unsufficient amount of cases. As a result fewer fruits are produced by the stenospermocarpic female plant. Furthermore, it is well known in the art that climate conditions, like rain, heat etc., may influence pollen production of a polliniser plant differently than stigma fertility time of the genotypic different female plant. Therefore, climate conditions can also lead to asynchrony of fertility time of pollinator and female plant with the effect of lowering the yield.

SUMMARY OF VARIOUS ASPECTS

The present inventors have found that mutating a single recessive gene in cultivated watermelon, referred herein to as the WOP1 gene, results in the watermelon plants developing seedless fruits when the flowers are not pollinated, i.e. parthenocarpy. If the flowers are pollinated, the fruits that develop produce normal viable seeds. This type of parthenocarpy is therefore referred to as facultative parthenocarpy, as it is only seen in the absence of pollination. The WOP1 gene is, therefore, responsible for facultative parthenocarpy in watermelon. Thus, when the mutant wop1 allele is present in homozygous form in a diploid watermelon plant, indicated herein as wop1/wop1, the plants are facultative parthenocarp and produce seedless fruits from non-pollinated flowers and normal seeded fruits from pollinated flowers.

This gene has great advantages in diploid watermelons, especially if combined with male sterility (MS) to ensure absence of pollination of the female flowers (as the male flowers produced on the plant are sterile) or combined with the emb1 mutant (in homozygous form, emb1/emb1) to ensure that, in case pollination does occur, the fruits are seedless due to the homozygous presence of the emb1 mutant in the plant. The emb1 mutant is a stenospermocarpy mutant, resulting in seedless fruits being produced upon pollination. Seeds comprising an emb1 mutant allele have been deposited by Nunhems B. V. on 27 Jan. 2016 under accession number NCIMB42532.

The WOP1 gene has also great advantages in triploid watermelons having three copies of the mutant allele (wop1/wop1/wop1) because there is no need anymore to interplant such triploid watermelon plants with a pollenizer plant (which is normally needed to induce fruit set in normal tripoids, having three copies of the wild type WOP1 allele). These parthenocarp triploid plants produce seedless fruits without the need for pollination to induce fruit set. Therefore basically the stenospermocarp nature of the normal triploid watermelons is changed into parthenocarpy. Yield of seedless triploid fruits is thereby increased greatly, as the pollenizer plants are not required anymore in a field and the entire field can comprise triploid watermelon plants.

In a population of mutagenized M2 diploid watermelon plants grown in insect-proof greenhouses so that no pollination could occur, a plant producing seedless fruits from un-pollinated female flowers (see FIG. 1B) was observed when screening more than 20,000 plants. The fruits contained only some traces of teguments of maternal origin (see FIGS. 1A and 1C), similar to what is seen in known triploid seedless fruits. Genetic analysis showed that the trait segregated as a single recessive gene. The gene was designated WOP1, and the mutant allele was designated wop1. Upon pollinating with other pollen of the same plant (selfpollination) or pollen of a different plant the female flowers of the plant homozygous for wop1 (i.e. wop1/wop1), fruits were produced containing normal viable seeds.

Figure 2:
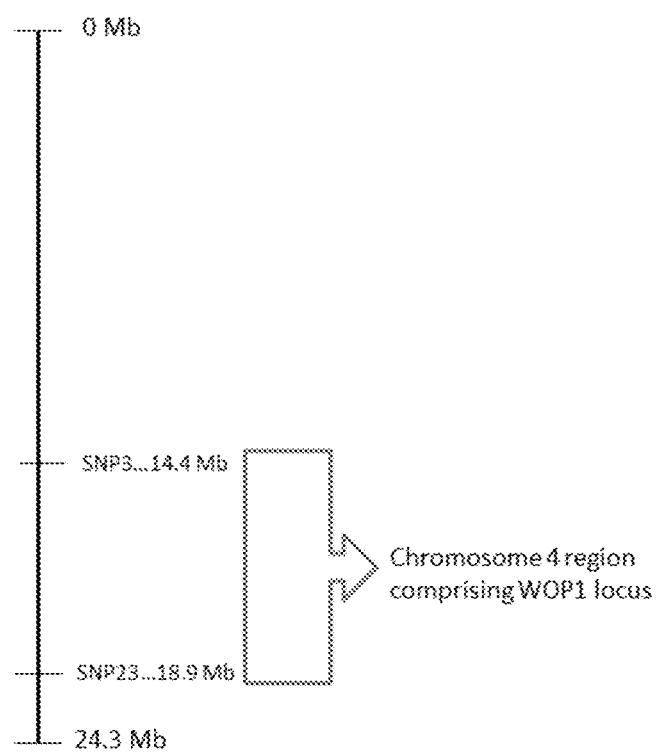

A mapping population was generated and the WOP1 locus was mapped to a region of cultivated watermelon chromosome 4 starting at 14.4 Mb (SNP3) and ending at 18.9 Mb (SNP23) of chromosome 4, i.e. a region of approximately 4.5 Mb in size (see FIG. 2). The chromosome 4 region comprising the WOP1 locus (and the mutant wop1 allele or wild type WOP1 allele) is defined herein by single nucleotide polymorphism (SNP) markers spanning the region between SNP3 and SNP23 and also the wider region between SNP1 and SNP24 (starting at 11.9 Mb and ending at 21.8 Mb) and even between SNP1a and SNP24 (starting at 8.3 Mb and ending at 21.8 Mb).

Whole genome sequencing was carried out to narrow down the region and to identify the WOP1 gene sequence, including the genomic sequence of the mutant wop1 allele and the wild type WOP1 allele. In one aspect the WOP1 gene is found in the region between SNP16 and SNP17. In one aspect the WOP1 gene is linked to SNP16a or SEQ ID NO: 30 or a nucleotide sequence comprising at least 95% sequence identity to SEQ ID NO: 30 and comprising the SNP nucleotide linked to the mutant (Adenine at nucleotide 428 of SEQ ID NO: 30).

In one aspect the WOP1 gene is the gene encoding a WOP1 protein, wherein a WOP1 protein is the protein of SEQ ID NO: 32 or a protein comprising at least 95% sequence identity to SEQ ID NO: 32. Putative orthologs of WOP1 were identified for cucumber and melon.

In one aspect of the invention a plant or plant cell is provided, characterized in that the plant or plant cell has decreased activity of a WOP1 protein compared to a corresponding wild type plant cell, wherein the WOP1 protein of the wild type plant cell is encoded by nucleic acid molecules selected from the group consisting of:
- a) nucleic acid molecules, which encode a protein with the amino acid sequence given under SEQ ID NO: 32 (watermelon) or SEQ ID NO: 33 (cucumber) or SEQ ID NO: 34 (melon);
- b) nucleic acid molecules, which encode a protein, the sequence of which has an identity of at least 95%, 96%, 97% or 98% with the amino acid sequence given under SEQ ID NO: 32 (watermelon) or SED ID NO: 33 (cucumber) or SEQ ID NO: 34 (melon);
- c) nucleic acid molecules, which encode a protein, the sequence of which has an identity of at least 95%, 96%, 97% or 98% with the amino acid sequence given under SEQ ID NO: 32 (watermelon) or SED ID NO: 33 (cucumber) or SEQ ID NO: 34 (melon) and wherein the protein comprises the amino acid sequence of SEQ ID NO: 35.

The decreased activity of the WOP1 protein is caused by a mutant wop1 allele. Decreased activity may be caused by a knock-down or knock-out of the expression of the mutant wop1 allele (e.g. through a mutation in the promoter or other regulatory sequence) or through the mutant wop1 allele encoding a loss-of-function or decreased-function WOP1 protein (mutant WOP1 protein).

In one aspect the mutant wop1 allele encodes a mutant WOP1 protein having decreased function or loss-of-function compared to the wild type protein, e.g. the mutant WOP1 protein comprises one or more amino acids replaced, deleted or inserted compared to the wild type protein. In one aspect the mutant WOP1 protein comprises one or more amino acids replaced, deleted or inserted in the conserved "myb like DNA binding domain, SHAQKYF" and/or in the "SHAQKYF" domain of the protein. In a preferred aspect, at least one amino acid in the conserved "myb like DNA binding domain, SHAQKYF" and/or in the "SHAQKYF" domain is replaced, resulting in a loss of function or decreased function protein and facultative parthenocarpy when the allele is in homozygous form (when no wild type allele is present in the plant or plant cell).

Also seeds were deposited by Nunhems B.V. on 27 Jan. 2016 under accession number NCIMB42533 produced by selfing a plant heterozygous for the mutant wop1 allele (i.e. WOP1/wop1). The deposited seeds consist of 25% WOP1/WOP1 (homozygous wild type WOP1 allele), 50% WOP1/wop1 (heterozygous) and 25% wop1/wop1 (homozygous for the mutant wop1 allele) plants. Phenotypically the wop1/wop1 plants show the facultative parthenocarpic phenotype, but selfing of the heterozygous plants will again result in a phenotypic segregation of 3:1 (75% wild type:25% facultative parthenocarpic). In addition, as mentioned above, SNP markers are provided herein by which plants homozygous or heterozygous for the mutant wop1 allele can be identified and/or selected. The seeds comprise the mutant wop1 allele of SEQ ID NO: 30, encoding the mutant WOP1 protein of SEQ ID NO: 31.

DETAILED DESCRIPTION

A cultivated watermelon plant or plant part is provided comprising at least one copy of a mutant allele of a gene name WOP1, said mutant allele conferring facultative parthenocarpy when the mutant allele is in homozygous form.

In one aspect the gene is located on chromosome 4, especially the gene is located in a region starting at base pair 11.906.147 and ending at base pair 21.897.585 of chromosome 4.

In one aspect said gene is located in a region starting at nucleotide 76 of SEQ ID NO: 1, or at nucleotide 76 of a sequence comprising at least 95% sequence identity to SEQ ID NO: 1, and ending at nucleotide 76 of SEQ ID NO: 24 or at nucleotide 76 of a sequence comprising at least 95% sequence identity to SEQ ID NO: 24.

In a further aspect the gene is linked a nucleotide sequence selected from the group consisting of SEQ ID NO: 1 or a sequence comprising at least 95% sequence identity to SEQ ID NO: 1; SEQ ID NO: 2 or a nucleotide sequence comprising at least 95% sequence identity to SEQ ID NO: 2; SEQ ID NO: 3 or a nucleotide sequence comprising at least 95% sequence identity to SEQ ID NO: 3; SEQ ID NO: 4 or a nucleotide sequence comprising at least 95% sequence identity to SEQ ID NO: 4; SEQ ID NO: 5 or a nucleotide sequence comprising at least 95% sequence identity to SEQ ID NO: 5; SEQ ID NO: 6 or a nucleotide sequence comprising at least 95% sequence identity to SEQ ID NO: 6; SEQ ID NO: 7 or a nucleotide sequence comprising at least 95% sequence identity to SEQ ID NO: 7; SEQ ID NO: 8 or a nucleotide sequence comprising at least 95% sequence identity to SEQ ID NO: 8; SEQ ID NO: 9 or a nucleotide sequence comprising at least 95% sequence identity to SEQ ID NO: 9; SEQ ID NO: 10 or a nucleotide sequence comprising at least 95% sequence identity to SEQ ID NO: 10; SEQ ID NO: 11 or a nucleotide sequence comprising at least 95% sequence identity to SEQ ID NO: 11; SEQ ID NO: 12 or a nucleotide sequence comprising at least 95% sequence identity to SEQ ID NO: 12; SEQ ID NO: 13 or a nucleotide sequence comprising at least 95% sequence identity to SEQ ID NO: 13; SEQ ID NO: 14 or a nucleotide sequence comprising at least 95% sequence identity to SEQ ID NO: 14; SEQ ID NO: 15 or a nucleotide sequence comprising at least 95% sequence identity to SEQ ID NO: 15; SEQ ID NO: 16 or a nucleotide sequence comprising at least 95% sequence identity to SEQ ID NO: 16; SEQ ID NO: 17 or a nucleotide sequence comprising at least 95% sequence identity to SEQ ID NO: 17; SEQ ID NO: 18 or a nucleotide sequence comprising at least 95% sequence identity to SEQ ID NO: 18; SEQ ID NO: 19 or a nucleotide sequence comprising at least 95% sequence identity to SEQ ID NO: 19; SEQ ID NO: 20 or a nucleotide sequence comprising at least 95% sequence identity to SEQ ID NO: 20; SEQ ID NO: 21 or a nucleotide sequence comprising at least 95% sequence identity to SEQ ID NO: 21; SEQ ID NO: 22 or a nucleotide sequence comprising at least 95% sequence identity to SEQ ID NO: 22; SEQ ID NO: 23 or a nucleotide sequence comprising at least 95% sequence identity to SEQ ID NO: 23; SEQ ID NO: 24 or a nucleotide sequence comprising at least 95% sequence identity to SEQ ID NO: 24.

In one embodiment the gene is located between a pair of markers selected from the group consisting of SNP1 and SNP3; SNP2 and SNP4; SNP3 and SNP5; SNP4 and SNP6; SNP5 and SNP7; SNP6 and SNP8; SNP7 and SNP9; SNP8 and SNP10; SNP9 and SNP11; SNP10 and SNP12; SNP11 and SNP13; SNP12 and SNP14; SNP13 and SNP15; SNP14 and SNP16; SNP15 and SNP17; SNP16 and SNP18; SNP17 and SNP19; SNP18 and SNP20; SNP19 and SNP21; SNP20 and SNP22; SNP21 and SNP23; SNP22 and SNP24.

In one embodiment the plant or plant part comprising the mutant allele of the WOP1 gene is diploid, tetraploid, triploid or polyploid. Preferably the mutant allele is present in two copies in a diploid plant or plant part, in four copies in a tetraploid plant or plant part or in three copies in a triploid plant or plant part.

In one aspect the mutant allele is the allele as found in seeds deposited under NCIMB42533 or progeny thereof.

Optionally the plant or plant part further comprises a gene conferring male sterility or a gene conferring stenospermocarpy.

The plant part comprising the mutant allele of the WOP1 gene may be a cell, a flower, a leaf, a stem, a cutting, an ovule, pollen, a root, a rootstock, a scion, a fruit, a protoplast, an embryo, an anther.

Also encompassed is a vegetatively propagated watermelon plant propagated from such a plant part comprising at least one mutant allele of the WOP1 gene.

Likewise a seed from which a plant of the invention can be grown is provided.

Further, a seedless fruit produced by a plant according to the invention is provided.

A method of producing seedless watermelon fruits is provided, said method comprising growing a triploid plant comprising three copies of a mutant allele of a WOP1 gene and harvesting the fruits produced by said plants. In particular the fruits develop without pollination of the female flowers.

A method for production of a facultative parthenocarpic cultivated watermelon plant is provided comprising the steps of:
a) introducing mutations in a population of watermelon plants;
b) selecting a plant producing seedless fruits without pollination of the female flowers and producing a seeded fruit after pollination of the female flowers;
c) optionally verifying if the plant selected under b) comprises a mutant allele of a WOP1 gene on chromosome 4; and
d) optionally growing the plants obtained under c).

A watermelon plant produced by the method is encompassed herein.

Use of a facultative parthenocarpic watermelon plant for producing seedless watermelon fruits, preferably without pollination of the female flowers of the plant is also an aspect of the invention.

Use of a mutant wop1 allele of a WOP1 gene according to the invention for producing facultative parthenocarpic watermelon plants is also an aspect of the invention.

GENERAL DEFINITION

The verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one", e.g. "a plant" refers also to several cells plants, etc. Similarly, "a fruit" or "a plant" also refers to a plurality of fruits and plants.

As used herein, the term "plant" includes the whole plant or any parts or derivatives thereof, preferably having the same genetic makeup as the plant from which it is obtained, such as plant organs (e.g. harvested or non-harvested fruits, leaves, flowers, anthers, etc.), plant cells, plant protoplasts, plant cell tissue cultures from which whole plants can be regenerated, plant calli, plant cell clumps, plant transplants, seedlings, plant cells that are intact in plants, plant clones or micropropagations, or parts of plants, such as plant cuttings, embryos, pollen, anthers, ovules, fruits (e.g. harvested tissues or organs), flowers, leaves, seeds, clonally propagated plants, roots, stems, root tips, grafts (scions and/or root stocks) and the like. Also any developmental stage is included, such as seedlings, cuttings prior or after rooting, etc. When "seeds of a plant" are referred to, these either refer to seeds from which the plant can be grown or to seeds produced on the plant, after self-fertilization or cross-fertilization.

As used herein, the term "variety" or "cultivar" means a plant grouping within a single botanical taxon of the lowest known rank, which can be defined by the expression of the characteristics resulting from a given genotype or combination of genotypes.

The term "allele(s)" means any of one or more alternative forms of a gene at a particular locus, e.g. the WOP1 locus (where the WOP1 gene is located; the alleles of the gene may be wild type alleles designated WOP1, or mutant alleles designated wop1), all of which alleles relate to one trait or characteristic at a specific locus (e.g. facultative parthenocarpy). In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous), e.g. two identical copies of the mutant wop1 allele (i.e. wop1/wop1) or one copy of the mutant wop1 allele and one copy of the wild type allele (i.e. wop1/WOP1). Likewise a triploid plant is referred to as homozygous for the gene if it has three identical alleles of a gene (e.g. three copies of the mutant wop1 allele, i.e. wop1/wop1/wop1) and a tetraploid plant is referred to as homozygous for the gene if it has four identical alleles of the gene, e.g. four copies of the mutant wop1 allele (i.e. wop1/wop1/wop1/wop1).

"WOP1 gene" is a single, recessive gene identified in cultivated watermelon on chromosome 4, which when mutated results in parthenocarpy, especially facultative parthenocarpy. WOP1 is the wild type (WT), functional allele as present in non-parthenocarpic cultivated watermelon plants and wop1 is the mutant allele resulting in parthenocarpy if the allele is in homozygous form in a diploid (wop1/wop1), triploid (wop1/wop1/wop1), tetraploid (wop1/wop1/wop1/wop1), or other polyploidy, e.g. octaploid (wop1/wop1/wop1/wop1/wop1/wop1/wop1/wop1) etc. In one aspect the WOP1 gene is the gene encoding a protein of SEQ ID NO: 32 or encoding a protein comprising at least 95%, 96%, 97% or 98% sequence identity to SEQ ID NO: 32 (watermelon), when aligned pairwise. This includes in one aspect orthologs of WOP1 in cucumber (SEQ ID NO: 33) and melon (SEQ ID NO: 34).

"Parthenocarpy" or "parthenocarpic" is generally understood in the art and also to be understood in connection with the present invention to describe the development of fruits without fertilization of the female ovule. A pollination process is not needed for producing fruits which fruits however as a consequence of the lack of pollination are seedless. Thus, parthenocarpy means herein that fruits are formed on the plant without pollination of the female flowers. Likewise a "parthenocarpic plant" or a "plant comprising a mutant gene (or mutant allele of a gene) conferring parthenocarpy when in homozygous form" means that the plant produces seedless fruits without pollination of the female flowers.

"Facultative parthenocarpy" is understood to mean that the parthenocarpy trait is not seen when the flower of the facultative parthenocarpic plant is pollinated, in which case normal fertilization and normal fruit development takes place. As normal fertilization takes place, the fruits are seeded.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 5, 6, 7 or more) of inbreeding, resulting in a plant line with a high uniformity.

The term "gene" means a (genomic) DNA sequence comprising a region (transcribed region), which is transcribed into a messenger RNA molecule (mRNA) in a cell, and an operably linked regulatory region (e.g. a promoter). An example is the WOP1 gene of the invention. Different alleles of a gene are thus different alternatives form of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

"Mutant wop1 allele" or "wop1 allele" refers herein to a mutant allele of the WOP1 gene on chromosome 4, which causes the plant to be facultative parthenocarpic when the mutant allele is in homozygous form. The mutation in the mutant allele can be any mutation or combination of mutations, including deletions, truncations, insertions, point mutations, non-sense mutations, mis-sense mutations or non-synonymous mutations, splice-site mutations, frame shift mutations and/or mutations in one or more regulatory sequences such as promoter sequence, or enhancer or silencer sequences. One example of a mutant wop1 allele is the allele found in 25% of the seeds deposited under NCIMB42533 in homozygous form. In one aspect the mutant wop1 allele is a mutant allele of the WOP1 gene whereby the WOP1 gene is the gene encoding a protein of SEQ ID NO: 32 or encoding a protein comprising at least 95%, 96%, 97% or 98% sequence identity to SEQ ID NO: 32 (when aligned pairwise). This includes in one aspect mutant alleles of orthologs of the WOP1 gene in cucumber (SEQ ID NO: 33) and melon (SEQ ID NO: 34) present in cucumber or melon plants or plant cells.

"Wild type WOP1 allele" or "WOP1 allele" refers herein to the functional allele of the WOP1 gene, which causes the plant to have a normal fruit set, requiring normal pollination and fertilization to set fruits. The wild type WOP1 allele is found in any commercial variety of watermelon (e.g. Nunhems variety Premium F1, Montreal F1, and others) and also in 25% of the seeds deposited under NCIMB42533 in homozygous form. In one aspect the wild type WOP1 allele is a wild type allele of the WOP1 gene whereby the WOP1 gene is the gene encoding a protein of SEQ ID NO: 32 or encoding a protein comprising at least 95%, 96%, 97% or 98% sequence identity to SEQ ID NO: 32 (when aligned pairwise). This includes in one aspect orthologs of the WOP1 gene in cucumber (SEQ ID NO: 33) and melon (SEQ ID NO: 34) present in cucumber or melon plants or plant cells.

The term "locus" (loci plural) means a specific place or places or a site on a chromosome where for example a gene or genetic marker is found. The WOP1 locus is, thus, the location in the genome of watermelon, where the mutant allele and/or the wild type allele of the WOP1 gene is found. The WOP1 locus is a locus on cultivated watermelon chromosome 4 (using the chromosome assignment of the published watermelon genome found at world wide web at icugi.org/cgi-bin/ICuGI/index.cgi under "Watermelon: Genome", "Watermelon genome (97103)—version 1" and as described in Guo S, Zhang J, Sun H, Salse J, Lucas W, Zhang H, Zheng Y, Mao L, Ren Y, Wang Z (2013) "The draft genome of watermelon (*Citrullus lanatus*) and resequencing of 20 diverse accessions" (Nature Genetics 45:51-58) i.e. wop1 was generated in the cultivated watermelon genome by mutagenesis and the mutant wop1 allele was mapped to a defined region of chromosome 4 of cultivated watermelon.

"Diploid plant" refers to a plant, vegetative plant part(s), or seed from which a diploid plant can be grown, having two sets of chromosome, designated herein as 2n.

A "DH plant" or "doubled-haploid plant" is a diploid plant produced by doubling the haploid genome of the diploid plant using e.g. in vitro techniques. A DH plant is, therefore, homozygous at all loci.

"Triploid plant" refers to a plant, vegetative plant part(s), or seed from which a triploid plant can be grown, having three sets of chromosomes, designated herein as 3n.

"Tetraploid plant" refers to a plant, vegetative plant part(s), or seed from which a tetraploid plant can be grown, having four sets of chromosomes, designated herein as 4n.

"Polyploid plant" refers to plants having a higher ploidy than diploid, i.e. triploid (3n), tetraploid (4n), hexaploid (6n), octaploid (8n), etc.

"Pollenizer plant" or "pollenizer" refers to the (inbred or hybrid) diploid plant, or parts thereof (e.g. its pollen or scion), suitable as pollenizer for inducing fruit set on triploid plants. A pollenizer plant is, thus, able to lead to good fruit set (and good triploid fruit yield) of normal triploid plants (comprising three copies of the wild type WOP1 allele), by producing an appropriate amount of pollen at the appropriate day-time and for an appropriate period of time.

"Hybrid triploid plant" or "F1 triploid" or "triploid hybrid" is a triploid plant grown from hybrid, triploid seed obtained from cross fertilizing a male diploid parent with a female tetraploid parent. The male parent is used for inducing fruit set and seed production on a tetraploid female parent, resulting in fruits containing F1 hybrid triploid seeds. Both the male parent and the female parent used to produce F1 triploid seeds are inbred so that each parent line is nearly homozygous and stable.

"Seedless fruit" are fruits which contain no viable mature seeds. The fruit may contain one or more small, edible, white ovules, e.g. as seen in FIGS. 1A and 1C. Optionally the fruit may contain a few brown or black seeds, but these are not viable. Viable mature seeds are seeds which can be germinated in soil under appropriate conditions and grow into plants.

"Planting" or "planted" refers to seeding (direct sowing) or transplanting seedlings (plantlets) into a field by machine or hand.

"Vegetative propagation" or "clonal propagation" refers to propagation of plants from vegetative tissue, e.g. by in vitro propagation or grafting methods (using scions and rootstocks). In vitro propagation involves in vitro cell or tissue culture and regeneration of a whole plant from the in vitro culture. Grafting involves propagation of an original plant by grafting onto a rootstock. Clones (i.e. genetically identical vegetative propagations) of the original plant can thus be generated by either in vitro culture or grafting. "Cell culture" or "tissue culture" refers to the in vitro culture of cells or tissues of a plant. "Regeneration" refers to the development of a plant from cell culture or tissue culture or vegetative propagation. "Non-propagating cell" refers to a cell which cannot be regenerated into a whole plant.

"Recessive" refers to an allele which expresses its phenotype (e.g. parthenocarpy or facultative parthenocarpy) when no dominant allele is present in the genome, i.e. when it is homozygous. The wop1 allele according to the invention results in a (facultative) parthenocarp plant when present in homozygous form, i.e. in two copies in a diploid plant, in four copies in a tetraploid plant or in three copies in a triploid plant or in the respective number of copies in another polyploidy (e.g. 8 copies in an octaploid), whereby a dominant allele WOP1 allele is absent in these plants. The dominant allele is herein also referred to as the wild type (WT) allele.

"Cultivated watermelon" or "*Citrullus lanatus*" refers herein to *Citrullus lanatus* ssp. *vulgaris*, or *Citrullus lanatus* (Thunb.) *Matsum.* & *Nakai* subsp. *vulgaris* (Schrad.), and having good agronomic characteristics, especially producing marketable fruits of good fruit quality and fruit uniformity. Cultivated cucumber and cultivated melon refer to *Cucumis sativus* and *Cucumis melo* plants having good agronomic characteristics, especially producing marketable fruits of good fruit quality and fruit uniformity.

"Wild watermelon" refers herein to *Citrullus lanatus* ssp. *lanatus* and *Citrullus lanatus* ssp. *mucosospermus*, producing fruits of poor quality and poor uniformity.

"SNP marker" refers to a Single Nucleotide Polymorphism between different cultivated watermelon lines and the SNP markers provided herein define the chromosome 4 region in which the WOP1 gene is found. The term "SNP genotype" refers to the nucleotide present at the particular SNP. The SNP haplotype refers to a particular genotype at several SNPs. It is noted that the wop1 mutant is a mutation in cultivated watermelon, not an introgression from a wild watermelon, meaning that the SNP genotype of the SNP marker linked to the WOP1 gene is not relevant as such (except where the SNP is in in one embodiment in the allele itself, e.g. as in one aspect for SNP16a), as the SNP genotype depends on the background breeding line, elite line or cultivar. The SNPs (the single nucleotide and/or the sequence comprising the SNP, or a variant sequence comprising at least 95% sequence identity to the given sequence) do however delimit the physical region on the chromosome 4 in which the WOP1 gene is found and can be used e.g. to distinguish plants comprising the mutant wop1 allele from plants lacking the mutant wop1 allele and having the wild type WOP1 allele instead, in plants grown from NCIMB42533 or progeny thereof.

"Cultivated watermelon genome" and "physical position on the cultivated watermelon genome" and "chromosome 4" refers to the physical genome of cultivated watermelon, world wide web at www.icugi.org/cgi-bin/ICuGI/index.cgi under "Watermelon: Genome", "Watermelon genome (97103)-version 1" and the physical chromosomes and the physical position on the chromosomes. So, for example SNP_01 (at nucleotide 76 of SEQ ID NO:1) is located at the nucleotide (or 'base') positioned physically at nucleotide 11.906.147 of chromosome 4, SNP_02 (at nucleotide 76 of SEQ ID NO: 2) is located at the nucleotide (or 'base') positioned physically at nucleotide 13.357.557 of chromosome 4, and SNP_03 (at nucleotide 76 of SEQ ID NO: 3) is located at the nucleotide (or 'base') positioned physically at nucleotide 14.402.485 of chromosome 4. Chromosome 4 has a physical size from 0 to 24.3 Mb.

A "chromosome 4 region comprising the mutant wop1 allele" refers to the genomic region of chromosome 4 of cultivated watermelon which region carries the mutant wop1 allele. The presence of the allele can be determined phenotypically and/or by the presence of one or more molecular markers, e.g. SNP markers or other markers, linked to the wop1 allele. A marker is "linked to the wop1 allele", if it is physically coupled to the allele. In one aspect a marker, such as a SNP marker, (or a nucleotide sequence comprising a marker) is linked to the wop1 allele if it is within a physical distance of 2.5 Mb or less, such as 2.0 Mb or less, 1.5 Mb or less, 1.0 Mb or less, 0.8 Mb or less, 0.5 Mb or less, 0.4 Mb or less, 0.3 Mb or less, 0.2 Mb or less, 0.1 Mb or less, 74 kb, 50 kb, 20 kb, 10 kb, 5 kb, 2 kb, 1 kb or less of the wop1 allele. In one aspect a marker or a nucleotide sequence comprising a marker is "closely linked to the mutant wop1 allele" if it is within a physical distance of 0.5 Mb or less, 0.4 Mb or less, 0.3 Mb or less, 0.2 Mb or less, 0.1 Mb or less, 74 kb, 50 kb, 20 kb, 10 kb, 5 kb, 2 kb, 1 kb or less of the wop1 allele.

A pair of "flanking markers" refers to two markers, preferably two SNP markers or two sequences comprising the SNP markers, which are linked to the wop1 allele, and/or which are closely linked to the wop1 allele, whereby the wop1 allele is located in-between the two markers or in-between the two sequences comprising the markers.

"Brix" or "degree Brix" or "° brix" refers to the mean total soluble solids content as measured on several mature fruits using a refractometer. Preferably the mean of at least three fruits, each measured between the centre and the rind of the cut-open fruit, is calculated.

"Marketable" in relation to fruit quality means that the watermelon fruits are suitable for being sold for fresh consumption, having good flavour (no off-flavours), a degree brix of at least 9.0, preferably at least 10.0 or at least 11.0 and preferably also a uniform fruit flesh color, being e.g. white (e.g. variety Cream of Saskatchewan), yellow (e.g. variety Yamato Cream 1), orange (e.g. variety Tendersweet), pink (e.g. variety Sadul), pinkish red (e.g. variety Crimson Sweet), red (e.g. variety Sugar Baby) or dark red (e.g. variety Dixie Lee).

"Uniform fruit flesh color" means that the color throughout the mature fruits, when cut open through the middle (midsection), is evenly distributed throughout the fruit flesh, i.e. not patchy. Thus, a red fruit is red throughout the fruit flesh and does not contain white patches. An example of a fruit with uniform red color is the diploid variety Premium F1 (Nunhems).

"Physical distance" between loci (e.g. between molecular markers and/or between phenotypic markers) on the same chromosome is the actually distance expressed in bases or base pairs (bp), kilo bases or kilo base pairs (kb) or megabases or mega base pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of about 1%. If no recombinants can be found, the RF is zero and the loci are either extremely close together physically or they are identical. The further apart two loci are, the higher the RF.

"Uniformity" or "uniform" relates to the genetic and phenotypic characteristics of a plant line or variety. Inbred lines are genetically highly uniform as they are produced by several generations of inbreeding. Likewise, and the F1 hybrids and the triploid hybrids which are produced from such inbred lines are highly uniform in their genotypic and phenotypic characteristics and performance.

A genetic element, an introgression fragment, or a gene or allele conferring a trait (such as parthenocarpy) is said to be "obtainable from" or can be "obtained from" or "derivable from" or can be "derived from" or "as present in" or "as found in" a plant or seed or tissue or cell if it can be transferred from the plant or seed in which it is present into another plant or seed in which it is not present (such as a non-parthenocarp line or variety) using traditional breeding techniques without resulting in a phenotypic change of the recipient plant apart from the addition of the trait conferred by the genetic element, locus, introgression fragment, gene or allele. The terms are used interchangeably and the genetic element, locus, introgression fragment, gene or allele can thus be transferred into any other genetic background lacking the trait. Not only seeds deposited and comprising the genetic element, locus, introgression fragment, gene or allele can be used, but also progeny/descendants from such seeds which have been selected to retain the genetic element, locus, introgression fragment, gene or allele, can be used and are encompassed herein, such as commercial varieties developed from the deposited seeds or from descendants or ancestors thereof. Likewise, other cultivated watermelons containing the genetic element, locus, introgression fragment, gene or allele (e.g. a mutant wop1 allele) can be generated de novo, e.g. by mutagenesis (e.g. chemical mutagenesis, CRISPR-Cas induced, etc.). The same applies for cucumber and melon, i.e. mutant wop1 alleles can be generated de novo by mutagenesis. Whether a plant (or genomic DNA, cell or tissue of a plant) comprises the same (or variant thereof) genetic element, locus, introgression fragment, gene or allele as obtainable from the deposited seeds can be determined by the skilled person using one or more techniques known in the art, such as phenotypic assays, whole genome sequencing, molecular marker analysis, trait mapping, chromosome painting, allelism tests and the like, or combinations of techniques.

"Average" or "mean" refers herein to the arithmetic mean and both terms are used interchangeably. The term "average" or "mean" thus refers to the arithmetic mean of several measurements. The skilled person understands that the phenotype of a plant line or variety depends to some extent on growing conditions and that, therefore, arithmetic means of at least 10, 15, 20, 30, 40, 50 or more plants (or plant parts) are measured, preferably in randomized experimental designs with several replicates and suitable control plants grown under the same conditions in the same experiment.

"Statistically significant" or "statistically significantly" different or "significantly" different refers to a characteristic of a plant line or variety that, when compared to a suitable control show a statistically significant difference in that characteristic (e.g. the p-value is less than 0.05, p<0.05, using ANOVA) from the (mean of the) control.

The term "traditional breeding techniques" encompasses herein crossing, backcrossing, selfing, selection, double haploid production, chromosome doubling, embryo rescue, protoplast fusion, marker assisted selection, mutation breeding etc., all as known to the breeder (i.e. methods other than genetic modification/transformation/transgenic methods), by which, for example, a chromosome 4 comprising a mutant wop1 allele can be obtained, identified and/or transferred.

"Backcrossing" refers to a breeding method by which a (single) trait, such as the facultative parthenocarpy trait, can be transferred from one (often an inferior) genetic background (also referred to as "donor") into another (often a superior) genetic background (also referred to as "recurrent parent". An offspring of a cross (e.g. an F1 plant obtained by crossing e.g. the donor with the recurrent parent watermelon, or an F2 plant or F3 plant, etc., obtained from selfing the F1), is "backcrossed" to the parent with e.g. the superior genetic background. After repeated backcrossing, the trait of the one (often inferior) genetic background will have been incorporated into the other (often superior) genetic background.

"Marker assisted selection" or "MAS" is a process of using the presence of molecular markers (such as SNP markers), which are genetically and physically linked to a particular locus or to a particular chromosome region, to select plants for the presence of the specific locus or region. For example, a molecular marker genetically and physically linked to the mutant wop1 allele, can be used to detect and/or select watermelon plants, or plant parts, comprising the wop1 allele. The closer the linkage of the molecular marker to the locus, the less likely it is that the marker is dissociated from the locus through meiotic recombination. Likewise, the closer two markers are linked to each other the less likely it is that the two markers will be separated from one another (and the more likely they will co-segregate as a unit).

A molecular marker (or a sequence comprising a molecular marker) within 5 Mb, 3 Mb, 2.5 Mb, 2 Mb, 1 Mb, 0.5 Mb, 0.4 Mb, 0.3 Mb, 0.2 Mb, 0.1 Mb, 74 kb, 50 kb, 20 kb, 10 kb, 5 kb, 2 kb, 1 kb or less of another marker (or a sequence comprising the molecular marker), or of a locus, refers to a marker which is physically located within the 5 Mb, 3 Mb, 2.5 Mb, 2 Mb, 1 Mb, 0.5 Mb, 0.4 Mb, 0.3 Mb, 0.2 Mb, 0.1 Mb, 74 kb, 50 kb, 20 kb, 10 kb, 5 kb, 2 kb, 1 kb or less, of the genomic DNA region flanking the marker (i.e. either side of the marker). See e.g. the diagram of FIG. 2, showing a region comprising the WOP1 locus, which was mapped to the region between SNP3 and SNP23. SNP4 to SNP22 lie in-between these two markers (not shown).

"LOD-score" (logarithm (base 10) of odds) refers to a statistical test often used for linkage analysis in animal and plant populations. The LOD score compares the likelihood of obtaining the test data if the two loci (molecular marker loci and/or a phenotypic trait locus) are indeed linked, to the likelihood of observing the same data purely by chance. Positive LOD scores favor the presence of linkage and a LOD score greater than 3.0 is considered evidence for linkage. A LOD score of +3 indicates 1000 to 1 odds that the linkage being observed did not occur by chance.

"Transgene" or "chimeric gene" refers to a genetic locus comprising a DNA sequence, such as a recombinant gene, which has been introduced into the genome of a plant by transformation, such as *Agrobacterium* mediated transformation. A plant comprising a transgene stably integrated into its genome is referred to as "transgenic plant".

An "isolated nucleic acid sequence" or "isolated DNA" refers to a nucleic acid sequence which is no longer in the natural environment from which it was isolated, e.g. the nucleic acid sequence in a bacterial host cell or in the plant nuclear or plastid genome. When referring to a "sequence" herein, it is understood that the molecule having such a sequence is referred to, e.g. the nucleic acid molecule.

A "host cell" or a "recombinant host cell" or "transformed cell" are terms referring to a new individual cell (or organism) arising as a result of at least one nucleic acid molecule, having been introduced into said cell. The host cell is preferably a plant cell or a bacterial cell. The host cell may contain the nucleic acid as an extra-chromosomally (episomal) replicating molecule, or comprises the nucleic acid integrated in the nuclear or plastid genome of the host cell, or as introduced chromosome, e.g. minichromosome.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimising the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 92%, 95%, 98%, 99% or more (as determined by Emboss "needle" using default parameters, i.e. gap creation penalty=10, gap extension penalty=0.5, using scoring matrix DNAFULL for nucleic acids an Blosum62 for proteins).

When reference is made to a nucleic acid sequence (e.g. DNA or genomic DNA) having "substantial sequence identity to" a reference sequence or having a sequence identity of at least 80%, e.g. at least 85%, 90%, 92%, 95%, 98%, 99%, 99.2%, 99.5%, 99.9% nucleic acid sequence identity to a reference sequence, in one embodiment said nucleotide sequence is considered substantially identical to the given nucleotide sequence and can be identified using stringent hybridisation conditions. In another embodiment, the nucleic acid sequence comprises one or more mutations compared to the given nucleotide sequence but still can be identified using stringent hybridisation conditions.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"M1 generation" or "M1 plants" in context with the present invention shall refer to the first generation that is produced directly from the mutagenic treatment. A plant grown from seeds treated with a mutagen e.g. is a representative of an M1 generation.

"M2 generation" or "M2 plant" shall refer herein to the generation obtained from self-pollination of the M1 generation. A plant grown from seeds obtained from a self-pollinated M1 plant represents a M2 plant. M3, M4, etc. refers to further generations obtained after self-pollination.

"Allelism test" refers to a genetic test whereby it can be tested whether a phenotype, e.g. facultative parthenocarpy, seen in two plant lines or varieties are determined by the same gene or locus or by different genes or loci. For example, the plants to be tested are crossed with each other (preferably after selfing to ensure they are homozygous), the segregation of the phenotypes amongst the F1 or further selfing or backcross progeny is determined. The ratio of segregation indicates if the genes or loci are allelic or if they are different. So for example if the alleles are of the same gene, F1 plants (produced by crossing two homozygous plants) will all (100%) have the same phenotype, while that may not be the case if the alleles are of different genes. Likewise in F2 plants phenotypic segregation will indicate whether the same or different genes are involved.

"Fine-mapping" refers to methods by which the position of a gene can be determined more accurately (narrowed down). For example a large population segregating for the trait can be analysed for segregation of the trait and the DNA markers, e.g. SNP1 to SNP24, and plants comprising recombination events in the region between SNP1 and SNP24 can be selected, in order to determine between which pair of SNP markers the gene is located. One can also search for additional markers between the most linked pair of marker to narrow down the interval in which the gene is located.

An "mRNA coding sequence" shall have the common meaning herein. An mRNA coding sequence corresponds to the respective DNA coding (cDNA) sequence of a gene/allele apart from that thymine (T) is replaced by uracil (U).

A "mutation" in a nucleic acid molecule (DNA or RNA) is a change of one or more nucleotides compared to the corresponding wild type sequence, e.g. by replacement, deletion or insertion of one or more nucleotides. Examples of such a mutation are point mutation, nonsense mutation, missense mutation, splice-site mutation, frame shift mutation or a mutation in a regulatory sequence.

A "nucleic acid molecule" shall have the common understanding in the art. It is composed of nucleotides comprising either of the sugars deoxyribose (DNA) or ribose (RNA).

A "point mutation" is the replacement of a single nucleotide, or the insertion or deletion of a single nucleotide.

A "nonsense mutation" is a (point) mutation in a nucleic acid sequence encoding a protein, whereby a codon in a nucleic acid molecule is changed into a stop codon. This results in a pre-mature stop codon being present in the mRNA and results in translation of a truncated protein. A truncated protein may have decreased function or loss of function.

A "missense or non-synonymous mutation" is a (point) mutation in a nucleic acid sequence encoding a protein, whereby a codon is changed to code for a different amino acid. The resulting protein may have decreased function or loss of function.

A "splice-site mutation" is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have decreased function or loss of function.

A "frame shift mutation" is a mutation in a nucleic acid sequence encoding a protein by which the reading frame of the mRNA is changed, resulting in a different amino acid sequence. The resulting protein may have decreased function or loss of function.

A "deletion" in context of the invention shall mean that anywhere in a given nucleic acid sequence at least one nucleotide is missing compared to the nucleic sequence of the corresponding wild type sequence or anywhere in a given amino acid sequence at least one amino acid is missing compared to the amino acid sequence of the corresponding (wild type) sequence.

A "truncation" shall be understood to mean that at least one nucleotide at either the 3'-end or the 5'-end of the nucleotide sequence is missing compared to the nucleic sequence of the corresponding wild type sequence or that at least one amino acid at either the N-terminus or the C-terminus of the protein is missing compared to the amino acid sequence of the corresponding wild type protein, whereby in a 3'-end or C-terminal truncation at least the first nucleotide at the 5'-end or the first amino acid at the N-terminus, respectively, is still present and in a 5'-end or N-terminal truncation at least the last nucleotide at the 3'-end or the last amino acid at the C-terminus, respectively, is still present. The 5'-end is determined by the ATG codon used as start codon in translation of a corresponding wild type nucleic acid sequence.

"Replacement" shall mean that at least one nucleotide in a nucleic acid sequence or one amino acid in a protein sequence is different compared to the corresponding wild type nucleic acid sequence or the corresponding wild type amino acid sequence, respectively, due to an exchange of a nucleotide in the coding sequence of the respective protein.

"Insertion" shall mean that the nucleic acid sequence or the amino acid sequence of a protein comprises at least one additional nucleotide or amino acid compared to the corresponding wild type nucleic acid sequence or the corresponding wild type amino acid sequence, respectively.

"Pre-mature stop codon" in context with the present invention means that a stop codon is present in a coding sequence (cds) which is closer to the start codon at the 5'-end compared to the stop codon of a corresponding wild type coding sequence.

A "mutation in a regulatory sequence", e.g. in a promoter or enhancer of a gene, is a change of one or more nucleotides compared to the wild type sequence, e.g. by replacement, deletion or insertion of one or more nucleotides, leading for example to decreased or no mRNA transcript of the gene being made.

A "mutation in a protein" is a change of one or more amino acid residues compared to the wild type sequence, e.g. by replacement, deletion, truncation or insertion of one or more amino acid residues.

"Mutant protein" is herein a protein comprising one or more mutations in the nucleic acid sequence encoding the protein, whereby the mutation results in (the mutant nucleic acid molecule encoding) a "reduced-function" or "loss-of-function" protein, as e.g. measurable in vivo, e.g. by the phenotype conferred by the mutant allele.

In context of the present invention, "decreased activity" of a protein shall mean a decrease in activity of a WOP1 protein when compared to a corresponding wild type plant cell or a corresponding wild type plant. Decrease shall in one aspect comprise an entire knock-out or knock-down of gene expression, or the production of a loss-of-function or of a reduced-function WOP1 protein, e.g. a mutant WOP1 protein may have lost function or decreased function compared to the wild type, functional WOP1 protein. A decrease in activity can be a decrease in the expression of a gene encoding a WOP1 protein (also referred to as knock-down), or a knock-out of the expression of a gene encoding a WOP1 protein and/or a decrease in the quantity of a WOP1 protein in the cells, or a reduced-function or loss-of-function in the activity of a WOP1 protein in the cells.

In context with the present invention, the term "wild type plant cell" or "wild type plant" means that they comprise wild type wop1 alleles and not mutant wop1 alleles. Thus, the wild type plant or wild type plant cell is a plant or plant cell comprising fully functional WOP1 genes, encoding a fully functional WOP1 proteins (also referred to as wild type WOP1 protein), e.g. regarding watermelon plants or plant cells a diploid watermelon plant producing the protein of SEQ ID NO: 32 (or a protein comprising at least 95% sequence identity to SEQ ID NO: 32) and producing fruits only after pollination. Or regarding melon plants or cells a diploid melon plant producing the protein of SEQ ID NO: 34 (or a protein comprising at least 95% sequence identity to SEQ ID NO: 34) or regarding cucumber plants or cells a diploid cucumber plant producing the protein of SEQ ID NO: 33 (or a protein comprising at least 95% sequence identity to SEQ ID NO: 34).

"Knock-out" or "entire knock-out" shall be understood that expression of the respective gene is not detectable anymore.

"Loss-of-function" or "reduced-function" or "decreased function" shall mean in context of the present invention that the protein, although possibly present in amounts equal or similar to a corresponding wild type protein, does not evoke its normal effect anymore, i.e. for mutant alleles encoding such a protein when present in homozygous form in a diploid plant, the plant produces seedless fruits in the absence of pollination and seeded fruits in the presence of pollination.

"Conserved domain" refer to conserved protein domains, such as the "myb-like DNA-binding domain, SHAQKYF class", e.g. of SEQ ID NO: 35, or the "SHAQKYF domain" of amino acids 47 to 54 of SEQ ID NO: 35. Conserved domains can e.g. be found in the Conserved Domain Database of the NCBI (world wide web at ncbi.nlm.nih.gov/cdd).

FIGS. 1: 1A and 1C show seedless fruits of a diploid, parthenocarpic watermelon plant of the invention, homozygous for the wop1 allele as e.g. found in NCIMB42533. FIG. 1B shows a female flower of the same plant developing a seedless fruit without pollination.

FIG. 2: schematic (not to scale) diagram of chromosome 4 of cultivated watermelon and the region to which WOP1 was mapped. The SNP markers found in between SNP3 and SNP23 are not shown, i.e. SNP4 to SNP22. The physical location and distance between the SNPs, as well as the SNP genotype, is shown in Table 1.

Figure 3:
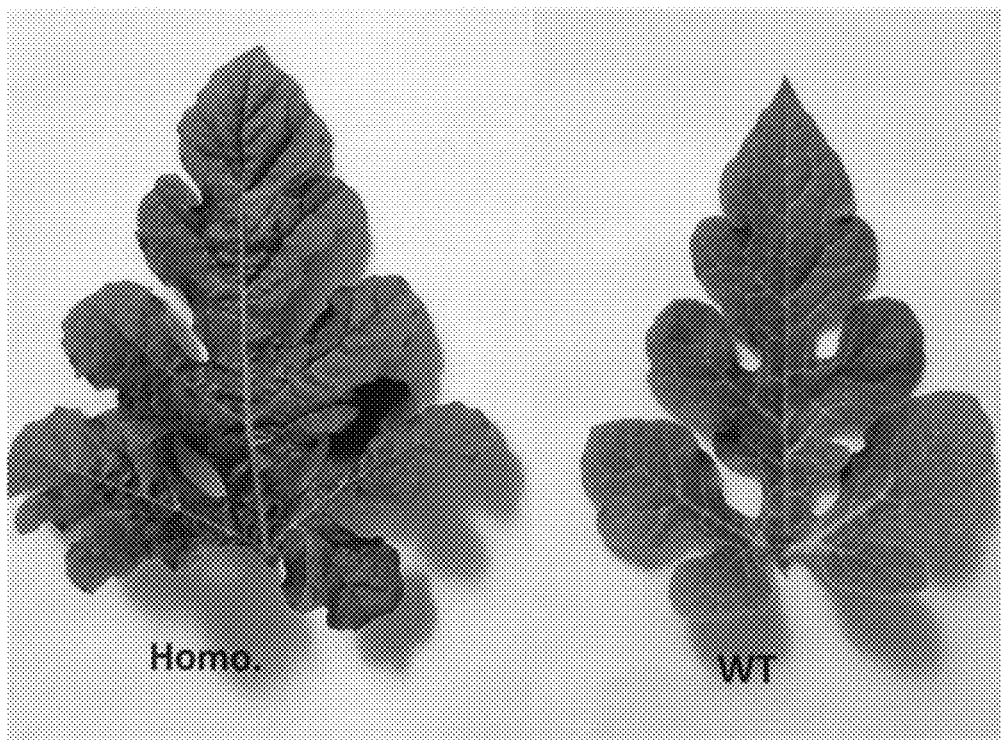

FIG. 3: leaf of a facultative parthenocarpic watermelon inbred backcross line homozygous for the mutant wop1 allele (as e.g. found in NCIMB42533) (left leaf) and leaf of a wild type watermelon plant (right leaf). The modified leaf morphology (left leaf) is also seen in backcross inbred lines heterozygous for the mutant wop1 allele.

DETAILED DESCRIPTION

A first embodiment of the present invention concerns cultivated watermelon plants, *Citrullus lanatus*, comprising at least one copy of a mutant allele of a gene conferring parthenocarpy when the mutant allele is in homozygous form, especially facultative parthenocarpy. Thus in one aspect cultivated watermelon plants are provided, comprising at least one copy of a mutant allele of a single recessive gene called WOP1.

The WOP1 gene is an endogenous gene of cultivated watermelon, which when mutated and in homozygous form results in parthenocarpy, especially facultative parthenocarpy.

A segregating population made by crossing the mutant parthenocarp watermelon plant identified by the inventors with an elite watermelon line enabled mapping of the WOP1 gene to a region on chromosome 4 between 8.3 Mb (SNP1a) or 11.9 Mb (SNP1) and 21.8 Mb (SNP24) of the chromosome, in particular the WOP1 gene was mapped to the region of chromosome 4 starting at nucleotide 14.402.485 (SNP3) and ending at nucleotide 18.942.612 (SNP23) of chromosome 4, see Table 1 below and FIG. 2.

Further analysis led to the identification of SNP16a comprising a polymorphism in a protein coding sequence. In the mutant parthenocapric watermelon plant SNP16a comprised an Adenine at nucleotide 428 of SEQ ID NO: 30, while the wild type plant comprised a Guanine at nucleotide 428. This resulted in a single amino acid change of the encoded protein, as codon AGC (encoding a Serine) was changed to codon AAC (encoding an Asparagine). Thus, the wild type protein, depicted in SEQ ID NO: 32, comprises a Serine at amino acid 143, and the mutant protein, depicted in SEQ ID NO: 31, comprises an Aspargine at amino acid 143. There were no introns in the sequence, so the genomic DNA and coding DNA (cDNA, and corresponding mRNA) are identical.

TABLE 1

| SNP marker name | Physical position (in base pairs) on chromosome 4 according to ICUGI.org version 1 of the genome | SNP nucleotide in plant comprising mutant wop1 allele (as found in NCIMB42533 plants comprising wop1) | SNP nucleotide in plant comprising wild type WOP1 allele (as found in NCIMB42533 plants lacking wop1) | Sequence comprising the SNP (with SNP indicated between brackets in bold) |
| --- | --- | --- | --- | --- |
| SNP1a | 8.385.759 | A | G | ATTGGTTTGTGACTCGGATTCAGAG GAATTGTTATTGGAAGAGAAGCTA TCATTTATGCATGAAACGAGGCAT GC[A/G]TTCGGAAGGACTGCCCTGC TCTTAAGTGGAGGTGCTTCACTTGG AGCTTTTCATACAGGAGTTGTCAAA ACTCTG (SEQ ID NO: 29) |
| SNP1 | 11.906.147 | A | G | TAGCTTTCAATTAGAATTTCTTATG AAAATTGTTTACGTATCAATTATCA TTGTCATTTTGCTAGTTTTACCTTT [A/G]AAGTTTAATTGATACAATTGTA AATCTCACCATGTTTTTCAAACGAA ATCTAAAAGAGTATAAATTGATAC AATT (SEQ ID NO: 1) |
| SNP2 | 13.357.557 | T | C | AGAAGARGGCGAAGTTGAGGAAAG AGCTCAGAGCCCTAAGAAGAGGAG CAGAGGAAATTGCTAAGGACGCAT TGT[C/T]CAACAAAAAGGTGTGCAG GGTAGTGCAACCTGAAGAAGAAAT ACAAACGCATAGACTTCCTGATCCT CAAGTAGA (SEQ ID NO: 2) |
| SNP3 | 14.402.485 | C | T | TAAAATGGTTGTTCAAGGAAGGTT ATTGAAAGATGATAATTTGATTTTC AAGTCAAACGATAATAGGAGACGC AT[C/T]AAAGAATCAAAAGGGATTT TTGAGTGAAAATTATTATTTAAAT GTTTCCTAATTGGTTATAAGGATGT TTTTCC (SEQ ID NO: 3) |

TABLE 1-continued

| SNP marker name | Physical position (in base pairs) on chromosome 4 according to ICUGI.org version 1 of the genome | SNP nucleotide in plant comprising mutant wop1 allele (as found in NCIMB42533 plants comprising wop1) | SNP nucleotide in plant comprising wild type WOP1 allele (as found in NCIMB42533 plants lacking wop1) | Sequence comprising the SNP (with SNP indicated between brackets in bold) |
| --- | --- | --- | --- | --- |
| SNP4 | 14.971.673 | C | T | CCGAGAGCGAGATTCTGAGCGAGA GCGAGAGAGCGAGAGTCTGAGCGA GAGAGTGAGATTCTGGCGAGGGAC TTC[C/T]CGGAAAGTAGAATCCGTC AAGGCGAGCGGCGACTGAGAGAGA GACAACGGGAAACAAAGGTAAAG AGAGAGTGTG (SEQ ID NO: 4) |
| SNP5 | 15.141.259 | A | G | AAGCAGCAGGCATTTTAGTTAATTA AACGAAAACTTACGGGAATTAGGA TTCATTAACTTAAATTAACTAAAGT T[A/G]ATTTTAAAAAATAGTGGAAT TGGTTTAACTTAAGTTTAATTAACT AATTAAAAATATAAAACTTAATCA GCTTTG (SEQ ID NO: 5) |
| SNP6 | 15.159.947 | C | T | AAAATTTACCTTTAGAGTTTGGACT CGCTGCCACTGGAAATCGACTCACT CACTAGCACTGATCTGAGACTTTTA [C/T]AAAAATGGAGAAAGACTTTTA CATGAGTTGGTAACACATACGGTG ACCAACTCCAACAAACAATCATCG CCTTAC (SEQ ID NO: 6) |
| SNP7 | 15.182.361 | T | C | CACCTCTTAGATGCAGGGTTGATAG TTTTTGGACTCGTAGTGCACTAGTT AGACGCCTAATTTTCTTCATAAAGG [C/T]TCTCAACTTTTCTTAATTTGAG TTCTAAAGTGATTTTCAGTGAGTAA AGAAGTGATTCCCCGAGTCTTATTT ATA (SEQ ID NO: 7) |
| SNP8 | 15.229.617 | G | A | AAATGAAGTTAAACCGAAAAAAGT GTGCTTTCGGAGTAGCTTCAGGCAA GTTTCTAGGCTTCATGGTCAATCAT A[A/G]AGGAATTAAAGCAAATCTA GACAAGATACGAGCTGTCCTGGAG ATGGAGTCTCCTAAGACACTAAAG CAACTTCA (SEQ ID NO: 8) |
| SNP9 | 15.341.020 | C | T | AAGGGTGATTGTACAAGAGAAGGA TTTGTAGCTAAGAATGGACATAAG GAAAGAGAGAGGACGCATGATAGT ATG[C/T]GATTAAGGCAGACGCATG GTATTATATGGTAAGCTGAAACGT ATAGTAGTATGCGTTTAAGACTTAA ACACCTAG (SEQ ID NO: 9) |
| SNP10 | 15.425.952 | A | G | ATGTTTGATTGAAACCAAAAACCA GAAGAATTCGAAGCTCAACCCAAT CCCAAGAAAGAGGAGTTGGAAGTG GTG[A/G]AAACGGGAGAAGAAGAA GAAGAACAACAACAACAACAAGAT GCTGAATCTTACTGTTCGAAGTTTA CTGGGTAGA (SEQ ID NO: 10) |
| SNP11 | 15.573.767 | G | A | GTTTGGTGAATATCTGAAACATACA AAATGGATTTAATTGTGTAGATAA ATTCATTGTTTAGAAACTTTCAAAT T[A/G]AATTGAAATTTCAAATTAAA ATGATGTTTCATGTACAAATTTAAC ATGTATGAAAGTTAAATTTGTAGTT TCTTC (SEQ ID NO: 11) |
| SNP12 | 15.638.032 | A | G | TTTTGTTATCTACTTTCTAAAAGTG TTCTAAAAAACCAATCAATGGTTTG GAAACTAGTTTTCAAAAATTTATTT TTGTTTTTAA[A/G]AATTTGACGAA |

TABLE 1-continued

| SNP marker name | Physical position (in base pairs) on chromosome 4 according to ICUGI.org version 1 of the genome | SNP nucleotide in plant comprising mutant wop1 allele (as found in NCIMB42533 plants comprising wop1) | SNP nucleotide in plant comprising wild type WOP1 allele (as found in NCIMB42533 plants lacking wop1) | Sequence comprising the SNP (with SNP indicated between brackets in bold) |
|---|---|---|---|---|
| | | | | AAATTCAAAAGTTTCTTTAAGAAA GGTTGAAGCTATAGTAAAGAATTT NTGAGG (SEQ ID NO: 12) |
| SNP13 | 15.961.924 | G | T | CAAAAGTTGCATGATATAGTAATA GCCAAACACATAATGTAATGTTAA GTATCCGAAGGTCGTAGTAATTCTC TT[G/T]ACTTACATTAACAGCAACA ATGGAAGGAAAAAAAAACCCAAAT AAGTACCCAAAAATTAAAGAATAC TTTCTATG (SEQ ID NO: 13) |
| SNP14 | 15.984.532 | A | G | TTGTAGAAATTAAACCCACAAATG ATAGAAATCGAACTCTCACATTTGT ACGATTATTACAATTTGTACAATTA T[A/G]TTAGTCTGAGAGTTCAATTTT AACATTTGTATAAGTTTGAAGTCTC AATTTTTAAAATTAAAAGTTTAAGG GGAT (SEQ ID NO: 14) |
| SNP15 | 16.021.388 | G | A | TGGAGTCACCCTTCGTCGGCCATAT TCTCGCATTTCCCCGTCACTCAGTT GCAGCGCTCCAGCCTTCACGGTGC G[A/G]CCTTAATCGCAGTTCACAGC ATTGTGGCATCGTCATAGTTGTCGC GCCGCAGCATCTTGGTCGTCGCGCC CCAGC (SEQ ID NO: 15) |
| SNP16 | 16.540.678 | A | G | ACTTTTCTAAAAAACAACCATTACT TATGCAATATGATTGATTCCTAATT TCTTGAAACCAAGTTAATAAGCAT A[A/G]CATTAAGATTAGTCATGATC AACTTTTTCTAATAACCTAGCTATT TAATTAATAGAGATTCAATGCTATA GATCC (SEQ ID NO: 16) |
| SNP16a | 16.610.755 | A | G | ATGAGGGAAGAACACTCGAATTGG TTCTCTAGGTGGGAAGAGGAGCTT CCATCTCCAGATGAATTGATGCCTC TTTCTCAAACCCTAATAACCCCCGA TCTAGCTTTGGCCTTTGATATTCAG AATCCCAGCAATAGCAGTCCGCCG TTGCCTTGTCCATCTCCGCCGCTTT CGAATCCTCTGCCTGGCTCTGGCAA CGGAATTGCGCAGCCCAACTCGGC GGATTTCGGCGATTCTGCCGATTTG GGCTCCGGCGCCGCCAGCGACGAG CCGGCTCGGACCCTCAAGCGACCA CGCCTTGTTTGGACGCCTCAGCTCC ACAAGCGATTCGTCGATGCTGTTGC TCATTTAGGGATAAAAAATGCCGT CCCCAAGACCATAATGCAGCTCAT GAGTGTCGATGGCTTGACCCGAGA GAACGTAGCTA[A/G]CCATTTGCAG AAGTACCGCCTCTATCTCAAGCGG ATGCAGGGGTTGTCCTCCGGCGGC GGCGGTGGTGGTGGTGGCTTGGTT GCTTCCTCCGATCCCGCCACTGACC ATTTGTTTGCCAGCTCCCCAGTTCC ACCCCATTTGCTTCACTCTGCTCGC ACCAGTTCAGACCATTTCTTGCCCT TTGTTCCCATGGCCACTCTGCAGCA GCACCACCATCACCAGCAGCAGAT GGCCGCTGCTGCTGCTGTCGCCGTC CATCCGCAGCTCCAGCCGCCTTATC ATCGGCAGGTCGGGCATTTCGGGT CACCGCCGAATGGCCAGTTTGAGC ATCCATTTTTAGCTAGACAGTCCCA |

TABLE 1-continued

| SNP marker name | Physical position (in base pairs) on chromosome 4 according to ICUGI.org version 1 of the genome | SNP nucleotide in plant comprising mutant wop1 allele (as found in NCIMB42533 plants comprising wop1) | SNP nucleotide in plant comprising wild type WOP1 allele (as found in NCIMB42533 plants lacking wop1) | Sequence comprising the SNP (with SNP indicated between brackets in bold) |
|---|---|---|---|---|
| | | | | GCCTATCCATAGAATGGGAGCACC AGTGCCTAATTCAGTTCCTAATTAC ATAGAGGATTTGGAATCAGCCAAT GCCAGTGGAGGAAGAAAAGTTCTC ACCTTATTTCCTACTGGGGATGATT GA (SEQ ID NO: 30) |
| SNP17 | 16.908.561 | G | A | ATGTAATTAGAGTAAGTATCCATAT GAAATATGATCCAATCGATATTTGA AATAATTAACAAACTTGCTACTAA A[A/G]AAAACTTTAGCTTTTAAACC TACACAAATTTAATATATGAAATAC ACTTTTGATCTGGTTGAATTCCAAT TCTAA (SEQ ID NO: 17) |
| SNP18 | 17.231.215 | C | A | TTTACTCAAATTTTAAAAAACTTGT TTTGTTTTTAGAACGGTGAAAATTA CCATAATTTAAAAATTGGAAGGAA C[A/C]AATATAAATTTTTAAGGAAA AAAAAACAAAAAAATTAAAACAAA ATCGTTGCAAAAGACCTTTAATTA TATTGA (SEQ ID NO: 18) |
| SNP19 | 17.429.279 | G | A | TCTACCAATCTTACTCTATTAATTC TCCCAATTTTTATTAGAAAAATTCT AAGAAAATTCTTATTCCCATAAGCG [A/G]TTCCCACAAACCAGATCTTTG CGCGAGTCATAGCGAGGAAGATCT CTTGGAAAAGAAAGACTACAAGGA GAAGAC (SEQ ID NO: 19) |
| SNP20 | 17.675.772 | T | C | AACATTTTACTATAAATTTTGGAAA CACATTCACATATTATATTTCTTTA CATAAAAATTATTGTTGTTATTTAA [C/T]CAATTTCAATAAAAATTAACTT TGAGAGACTAAATTTAAGATTTATT AAAAATACATAAATTAAAATTGGA CAAT (SEQ ID NO: 20) |
| SNP21 | 17.819.497 | G | T | AACATCCTAAAACTATGAGTTTAGC CACGGATAGACATCAAATACATAC ATTCATATGAGTTCTCAAGCATAAA A[G/T]TAAAAGAGAAAGAGAAACT TAGGAAGAAAGACTCTCGAATTGC TTCCCCGCGTTGAATTCCTTCGATC TCCACTT (SEQ ID NO: 21) |
| SNP22 | 18.708.457 | G | C | CTTTTCAGGTGGCTACTCCTAAACA TTTCTTTACAGGTGGGTGCTTCTAG CATGACAGTTTTACGTAGTATTTGG CAGA[C/G]TTACTGGCTCGATAAGC ATGGGGATGCCATGGAGAGCGTTG TTGATCAGCTTGCACGAAGTCTATC AGAGA (SEQ ID NO: 22) |
| SNP23 | 18.942.612 | G | T | ATATGTCATTAATAAATTGCTAACT AGACTAAAAATTTAGATGTCTAAA CACATATGTTGCTTAGGTGTGCCAA ATAATC[G/T]GATTGATATATATGG AAATTTACGATCATAGAATAATTAT TTTAGGGCCATTTTTTTAATTGACG TTTAA (SEQ ID NO: 23) |

TABLE 1-continued

| SNP marker name | Physical position (in base pairs) on chromosome 4 according to ICUGI.org version 1 of the genome | SNP nucleotide in plant comprising mutant wop1 allele (as found in NCIMB42533 plants comprising wop1) | SNP nucleotide in plant comprising wild type WOP1 allele (as found in NCIMB42533 plants lacking wop1) | Sequence comprising the SNP (with SNP indicated between brackets in bold) |
|---|---|---|---|---|
| SNP24 | 21.897.585 | C | A | TCAGATGAGTGACGTTCAATTTGTC TATTTTATTGTACAATCAATGATCA CAACAAAGCTATTTATATTTTCAAT [A/C]ATTCTATTTTTGTTGTATAGTA ATTTTGTTATATAGTAATTTCGTTA TCCTAAACTATTTTCATTCTTCTAA GTA (SEQ ID NO: 24) |

When referring to specific SNPs, reference is either made to the specific nucleotide number of the SNP and/or to the entire sequence comprising the SNP. For example, SNP1 refers herein either to nucleotide 76 of SEQ ID NO: 1, or nucleotide 76 of a sequence comprising at least 95%, 96%, 97%, 98% or 99% sequence identity to SEQ ID NO: 1, and/or, SNP1 refers to SEQ ID NO: 1, or a sequence comprising at least 95%, 96%, 97%, 98% or 99% sequence identity to SEQ ID NO: 1. To indicate both possibilities brackets are used as follows: SNP1 refers herein to (nucleotide 76 of) SEQ ID NO: 1, or (nucleotide 76 of) a sequence comprising at least 95%, 96%, 97%, 98% or 99% sequence identity to SEQ ID NO: 1.

Thus, SNP1a refers herein to (nucleotide 76 of) SEQ ID NO: 29, or (nucleotide 76 of) a sequence comprising at least 95%, 96%, 97%, 98% or 99% sequence identity to SEQ ID NO: 29; SNP1 refers herein (to nucleotide 76) of SEQ ID NO: 1, or (nucleotide 76 of) a sequence comprising at least 95%, 96%, 97%, 98% or 99% sequence identity to SEQ ID NO: 1; SNP2 refers (to nucleotide 76 of) SEQ ID NO: 2, or (nucleotide 76 of) a sequence comprising at least 95%, 96%, 97%, 98% or 99% sequence identity to SEQ ID NO:2; SNP3 refers (to nucleotide 76 of) SEQ ID NO: 3, or (nucleotide 76 of) a sequence comprising at least 95%, 96%, 97%, 98% or 99% sequence identity to SEQ ID NO:3; SNP4 refers to (nucleotide 76 of) SEQ ID NO: 4, or (nucleotide 76 of) a sequence comprising at least 95%, 96%, 97%, 98% or 99% sequence identity to SEQ ID NO:4; SNP5 refers to (nucleotide 76 of) SEQ ID NO: 5, or (nucleotide 76 of) a sequence comprising at least 95%, 96%, 97%, 98% or 99% sequence identity to SEQ ID NO:5; SNP6 refers to (nucleotide 76 of) SEQ ID NO: 6, or (nucleotide 76 of) a sequence comprising at least 95%, 96%, 97%, 98% or 99% sequence identity to SEQ ID NO:6; SNP7 refers to (nucleotide 76 of) SEQ ID NO: 7, or (nucleotide 76 of) a sequence comprising at least 95%, 96%, 97%, 98% or 99% sequence identity to SEQ ID NO:7; SNP8 refers to (nucleotide 76 of) SEQ ID NO: 8, or (nucleotide 76 of) a sequence comprising at least 95%, 96%, 97%, 98% or 99% sequence identity to SEQ ID NO:8; SNP9 refers to (nucleotide 76 of) SEQ ID NO: 9, or (nucleotide 76 of) a sequence comprising at least 95%, 96%, 97%, 98% or 99% sequence identity to SEQ ID NO:9; SNP10 refers to (nucleotide 76 of) SEQ ID NO: 10, or (nucleotide 76 of) a sequence comprising at least 95%, 96%, 97%, 98% or 99% sequence identity to SEQ ID NO:10; SNP11 refers to (nucleotide 76 of) SEQ ID NO: 11, or (nucleotide 76 of) a sequence comprising at least 95%, 96%, 97%, 98% or 99% sequence identity to SEQ ID NO:11; SNP12 refers to (nucleotide 86 of) SEQ ID NO: 12, or (nucleotide 86 of) a sequence comprising at least 95%, 96%, 97%, 98% or 99% sequence identity to SEQ ID NO:12; SNP13 refers to (nucleotide 76 of) SEQ ID NO: 13, or (nucleotide 76 of) a sequence comprising at least 95%, 96%, 97%, 98% or 99% sequence identity to SEQ ID NO:13; SNP14 refers to (nucleotide 76 of) SEQ ID NO: 14, or (nucleotide 76 of) a sequence comprising at least 95%, 96%, 97%, 98% or 99% sequence identity to SEQ ID NO:14; SNP15 refers to (nucleotide 76 of) SEQ ID NO: 15, or (nucleotide 76 of) a sequence comprising at least 95%, 96%, 97%, 98% or 99% sequence identity to SEQ ID NO:15; SNP16 refers to (nucleotide 76 of) SEQ ID NO: 16, or (nucleotide 76 of) a sequence comprising at least 95%, 96%, 97%, 98% or 99% sequence identity to SEQ ID NO:16; SNP16a refers to (nucleotide 428 of) SEQ ID NO: 30, or (nucleotide 428 of) a sequence comprising at least 95%, 96%, 97%, 98% or 99% sequence identity to SEQ ID NO:30; SNP17 refers to (nucleotide 76 of) SEQ ID NO: 17, or (nucleotide 76 of) a sequence comprising at least 95%, 96%, 97%, 98% or 99% sequence identity to SEQ ID NO:17; SNP18 refers to (nucleotide 76 of) SEQ ID NO: 18, or (nucleotide 76 of) a sequence comprising at least 95%, 96%, 97%, 98% or 99% sequence identity to SEQ ID NO:18; SNP19 refers to (nucleotide 76 of) SEQ ID NO: 19, or (nucleotide 76 of) a sequence comprising at least 95%, 96%, 97%, 98% or 99% sequence identity to SEQ ID NO:19; SNP20 refers to (nucleotide 76 of) SEQ ID NO: 20, or (nucleotide 76 of) a sequence comprising at least 95%, 96%, 97%, 98% or 99% sequence identity to SEQ ID NO:20; SNP21 refers to (nucleotide 76 of) SEQ ID NO: 21, or (nucleotide 76 of) a sequence comprising at least 95%, 96%, 97%, 98% or 99% sequence identity to SEQ ID NO:21; SNP22 refers to (nucleotide 80 of) SEQ ID NO: 22, or (nucleotide 80 of) a sequence comprising at least 95%, 96%, 97%, 98% or 99% sequence identity to SEQ ID NO:22; SNP23 refers to (nucleotide 81 of) SEQ ID NO: 23, or (nucleotide 81 of) a sequence comprising at least 95%, 96%, 97%, 98% or 99% sequence identity to SEQ ID NO:23; SNP24 refers to (nucleotide 76 of) SEQ ID NO: 24, or (nucleotide 76 of) a sequence comprising at least 95%, 96%, 97%, 98% or 99% sequence identity to SEQ ID NO:24. Sequence identity is preferably determined by pairwise alignment of sequences of the same length.

In one aspect the WOP1 gene and the copy of the mutant allele is located in the region between 8.3 Mb (SNP1a) or 11.9 Mb (SNP1) and 21.8 Mb (SNP24), preferably between 14.4 Mb (SNP3) and 18.9 Mb (SNP23) of chromosome 4. In another aspect the WOP1 gene and the copy of the mutant allele is located in the region between 16.5 Mb (SNP16) and 16.9 Mb (SNP17). In another aspect the WOP1 gene and the copy of the mutant wop1 allele is linked to SNP16a or to SEQ ID NO: 30 or a sequence comprising at least 95% sequence identity to SEQ ID NO: 30, preferably to a Adenine at nucleotide 428 of SEQ ID NO: 30.

As nucleotide 11.906.147 of chromosome 4 is SNP1 and nucleotide 21.897.585 is SNP24 herein, the copy of the mutant allele is, in one aspect, located between (nucleotide 76 of) SEQ ID NO:1 or (nucleotide 76 of) a sequence comprising at least 95%, 96%, 97%, 98% or more sequence identity to SEQ ID No:1 and (nucleotide 76 of) SEQ ID No: 24 or (nucleotide 76 of) a sequence comprising at least 95%, 96%, 97%, 98% or more sequence identity to SEQ ID No:24.

As nucleotide 8.385.759 of chromosome 4 is SNP1a and nucleotide 21.897.585 is SNP24 herein, the copy of the mutant allele is, in one aspect, located between (nucleotide 76 of) SEQ ID NO:29 or (nucleotide 76 of) a sequence comprising at least 95%, 96%, 97%, 98% or more sequence identity to SEQ ID No:29 and (nucleotide 76 of) SEQ ID NO 24 or (nucleotide 76 of) a sequence comprising at least 95%, 96%, 97%, 98% or more sequence identity to SEQ ID No:24.

In another aspect the WOP1 gene and the copy of the mutant allele is located in the region between 14.4 Mb (SNP3) and 18.9 Mb (SNP23).

As nucleotide 14.402.485 is SNP3 herein and nucleotide 18.942.612 is SNP23 herein, the copy of the mutant allele is, in another aspect, located between (nucleotide 76 of) SEQ ID NO:3 or (nucleotide 76 of) a sequence comprising at least 95%, 96%, 97%, 98% or more sequence identity to SEQ ID No:3 and (nucleotide 81 of) SEQ ID No: 23 or (nucleotide 81 of) a sequence comprising at least 95%, 96%, 97%, 98% or more sequence identity to SEQ ID No:23.

In another aspect the WOP1 gene and the copy of the mutant allele is located in the region between 16.5 Mb (SNP16) and 16.9 Mb (SNP17).

As nucleotide 16.540.678 is SNP16 herein and nucleotide 16.908.561 is SNP17 herein, the copy of the mutant allele is, in another aspect, located between (nucleotide 76 of) SEQ ID NO:16 or (nucleotide 76 of) a sequence comprising at least 95%, 96%, 97%, 98% or more sequence identity to SEQ ID No:16 and (nucleotide 76 of) SEQ ID No: 17 or (nucleotide 76 of) a sequence comprising at least 95%, 96%, 97%, 98% or more sequence identity to SEQ ID No:17.

In a further embodiment, the mutant allele is located in the region between any two SNP markers selected from the group consisting of SNP1a to SNP24; or between any two SNP markers selected from the group consisting of SNP1 to SNP24; or between any two SNP markers selected from the group consisting of SNP3 to SNP23. So for example, in one aspect the mutant wop1 allele is found between SNP1 (or SNP1a) and SNP3, between SNP2 and SNP4, between SNP3 and SNP5, between SNP4 and SNP6, etc. up to between SNP22 and SNP24. In one aspect the mutant wop1 allele is found between SNP3 and SNP5, or between SNP4 and SNP6, or between SNP5 and SNP7, or between SNP6 and SNP8, etc. up to between SNP21 and SNP23. In a preferred aspect the mutant wop1 allele is found between SNP16 and SNP17.

Fine-mapping and/or sequencing can be done do determine between which pair of SNP markers the mutant allele is located and/or to identify the gene itself. For example, comparison of the genomic sequence of chromosome 4 in the region between SNP1 (or SNP1a) and SNP24 (or between SNP3 and SNP23) between a plant homozygous for the wild type WOP1 gene and a plant homozygous for the mutant wop1 gene allows identification of the gene itself. In one aspect the WOP1 gene is the gene encoding the protein of SEQ ID NO: 32, herein referred to as the WOP1 protein. One mutant wop1 allele according to the invention is the mutant allele comprising the nucleotide sequence of SEQ ID NO: 30, encoding the mutant WOP1 protein of SEQ ID NO: 31, but other mutant wop1 alleles are also encompassed herein, as described elsewhere herein.

In one aspect the mutant wop1 allele is linked to (preferably closely linked to) at least one molecular marker, preferably a SNP marker (or sequence comprising the SNP marker, or a sequence comprising at least 90%, 95%, 96%, 97%, 98% or 99% sequence identity to the sequence comprising the SNP marker) selected from the group consisting of SNP1a, SNP1, SNP2, SNP3, SNP4, SNP5, SNP6, SNP7, SNP8, SNP9, SNP10, SNP11, SNP12, SNP13, SNP14, SNP15, SNP16, SNP16a, SNP17, SNP18, SNP19, SNP20, SNP21, SNP22, SNP23 and SNP24. In one aspect the wop1 allele is linked to, preferably closely linked to, at least one marker selected from the group consisting of SNP3, SNP4, SNP5, SNP6, SNP7, SNP8, SNP9, SNP10, SNP11, SNP12, SNP13, SNP14, SNP15, SNP16, SNP16a, SNP17, SNP18, SNP19, SNP20, SNP21, SNP22 and SNP23. In a further aspect the mutant wop1 allele is linked to SNP16, SNP16a and/or SNP17, preferably to at least SNP16a, e.g. to an Adenine at nucleotide 428 of SEQ ID NO: 30.

The mutant allele of the WOP1 gene is in one aspect the mutant allele as found in seeds deposited under accession number NCIMB42533 or progeny thereof. The mutant allele comprises a mutation in the genomic DNA (identical to the cDNA and mRNA, whereby in the mRNA 'Thymine' is replaced by 'Uracil') of SEQ ID NO: 30, resulting in the expression of a mutant WOP1 protein (SEQ ID NO: 31). The mutant WOP1 protein comprises a single amino acid replacement of Serine 143 (replaced by Asparagine). This amino acid replacement is in the conserved domain referred to as myb-like DNA binding domain SHAQKYF class. In fact the amino acid substitution is in the C-terminal of that conserved domain, in the SHAQKYF domain. The myb-like DNA binding domain SHAQKYF class is highly relevant for the three dimensional structure of the protein and comprises several alpha helices. The amino acid substitution in this conserved domain leads to a reduced function of the protein, possibly even a loss-of-function, compared to the wild type WOP1 protein of SEQ ID NO: 32.

The mutant WOP1 allele as found in the deposited seeds is one aspect of the invention. However, also different mutant alleles of the WOP1 gene, causing facultative parthenocarpy when in homozygous form, are embodiments of the invention. Such different mutant wop1 alleles can be generated by the skilled person without undue burden. The skilled person can, for example, generate other mutants in the WOP1 gene and determine whether they equally result in facultative parthenocarpy when in homozygous form in a diploid watermelon plant.

As mentioned the WOP1 gene in watermelon was identified to be a gene encoding a protein of SEQ ID NO: 32, which is a small protein comprising the conserved "myb-like DNA binding SHAQKYF class" domain from amino acid 97 to amino acid 150 of SEQ ID NO: 32. The conserved domain is also depicted in SEQ ID NO: 35. An amino acid substitution in the SHAQKYF domain, which is part of this larger conserved domain at (and including) amino acid 143 to (and including) amino acid 150, was found in the facultative parthenocarpic mutant and is responsible for the phenotype when the mutant allele is in homozygous form. The mutant protein of SEQ ID NO: 31, comprising the S143N mutation (Serine 143 to Asparagine substitution), thus has a reduced function or loss-of-function compared to the wild type protein of SEQ ID NO: 32, causing facultative parthenocarpy in watermelon. Also orthologs in cucumber and melon of the WOP1 gene were identified, enabling parthenocarpic cucumber and melon plants to be made without undue burden.

Having identified the nucleotide sequence of the gene, the skilled person can generate watermelon plants comprising mutants in the WOP1 gene by various methods, e.g. mutagenesis, TILLING or CRISPR-Cas or other methods known in the art. Especially with targeted gene modification technologies such as Crispr-Cas, TALENS and others, targeted mutations can be made by the person skilled in the art. He can then confirm the phenotype of a plant homozygous for the mutant wop1 allele, i.e. being facultative parthenocarpic, optionally in comparison to the phenotype of plants accession number NCIMB42533 or progeny thereof. Therefore the skilled person is not limited to the specific WOP1 mutant generated by the inventors and of which the mutant allele is present in the deposited seeds, but the skilled person can equally generate other mutations in the wop1 allele of watermelon, and also of cucumber and melon, and thereby generate other mutants which lead to facultative parthenocarpy when in homozygous form. Various mutations can be generated and tested for the resulting phenotype, for example the regulatory elements can be mutated to reduce expression (knock-down) or eliminate expression (knock-out) of the allele and thus reduce or eliminate the amount of WOP1 protein present in the cell or plant. Alternatively, mutations which lead to reduced function or loss-of-function of the WOP1 protein can be generated, i.e. mutations (such as missense mutations or frame shift mutations) which lead to one or more amino acids being substituted, inserted or deleted, or whereby the protein is truncated through the introduction of a stop-codon in the coding sequence (nonsense mutations). As the WOP1 protein comprises a large conserved domain, the "myb-like DNA binding SHAQKYF class domain", encompassing a smaller conserved domain, the SHAQKYF domain", it is in one aspect encompassed that one or more amino acids are replaced, deleted or inserted in either of" these domains, as such mutations will likely reduced the protein function or result in a loss of function. Whether the mutation results in the expected phenotype (facultative parthenocarpy) can then be tested by generating plants homozygous for the mutation through selfing and growing the plant line with and without pollination of the flowers to see if fruits develop in a facultative parthenocarpic way.

Alternatively, the skilled person can carry out a method for production of a facultative parthenocarpic cultivated watermelon plant comprising the steps of:
a) introducing mutations in a population of watermelon plants, especially cultivated watermelon plants or providing a population of mutated plants or progeny thereof;
b) selecting a plant producing seedless fruits without pollination of the female flowers and producing a seeded fruit after pollination of the female flowers;
c) optionally determining if the plant selected under b) comprises a mutant allele of a WOP1 gene; and
d) optionally growing the plants obtained under c).

Steps b) and c) can also be switched, so that step b) is selecting a plant comprising a mutant allele of a WOP1 gene and step c) is determining if the plant (or a progeny thereof produced by selfing) producing seedless fruits without pollination of the female flowers and producing a seeded fruit after pollination of the female flowers.

Step a) can be carried out by e.g. mutagenizing seeds of one or more lines or varieties of watermelon, for example by treatment with mutagenizing agents such as chemical mutagens, e.g. EMS (ethyl methane sulphonate), or irradiation with UV radiation, X-rays or gamma rays or the like. The population may for example be a TILLING population. Preferably the mutagnized plant population is selfed at least once (e.g. to produce an M2 generation, or M3, M4, etc.) prior to carrying out step b). In step b) relating to phenotyping, plants are preferably grown in an insect proof environment to avoid the presence of pollinators. Regular visual inspection of female flowers, fruit setting of those flowers without pollination and visual inspection of the mature fruits (e.g. presence of viable seeds or seedless) can be carried out to identify mutants which producing seedless fruits without pollination of the female flowers. Such plants, or selfing progeny thereof, can be tested for the presence of the mutant WOP1 gene by pollinating the female flowers to see if the fruits are seeded after pollination, genotyping the plants for mutations in the WOP1 gene and encoded protein, or expression of the WOP1 gene, or genotyping the plant for one or more or all of SNP1 (or SNP1a) to SNP24, allelism tests by e.g. crossing the plants with plants comprising wop1 derived from seeds deposited under NCIMB42533, sequencing and other methods known to the skilled person. There are, thus, various methods, or combinations of methods, for verifying if a phenotypically selected plant comprises a mutant allele of a WOP1 gene on chromosome 4. If step b) is the selection of plants comprising a mutant allele of the WOP1 gene, the skilled person can also use various methods for detecting the DNA, mRNA or protein of the WOP1 gene in order to identify a plant comprising a mutant wop1 allele. The genomic coding DNA of the wild type WOP1 gene, encoding a functional WOP1 protein (SEQ ID NO: 32) is the DNA of SEQ ID NO: 30, except that the Adenine at nucleotide 428 is a Guanine. The promoter is upstream of this sequence and can e.g. be retrieved by sequencing or from the watermelon genome database.

In one aspect the mutant allele of the WOP1 gene is a mutant allele resulting in reduced expression or no expression of the WOP1 gene or is a mutant allele resulting in one or more amino acids of the encoded WOP1 protein being replaced, inserted or deleted, compared to the wild type WOP1 protein.

In one aspect the mutant allele of the WOP1 gene is obtainable from seeds deposited under accession number NCIMB42533 or progeny thereof, e.g. by crossing a plant comprising one or two copies of the mutant wop1 allele with another cultivated watermelon plant. To select or identify a plant comprising one or two copies of the mutant wop1 allele as found in NCIMB42533, the SNP genotype of one or more or all of the SNP markers selected from SNP1 (or SNP1a) to SNP24 (or SNP3 to 23) can be determined. Especially in one aspect the genotype of SNP16a can be determined and used to select progeny plants comprising an Adenine at nucleotide 428 of SEQ ID NO: 30 and thus comprising the mutant wop1 allele. The diploid plant heterozygous for wop1 (i.e. wop1/WOP1) will be heterozygous for the SNP markers, e.g. will have the genotype 'AG' for SNP1 (i.e. the plant comprises one chromosome 4 having an Adenine, A, at nucleotide 76 of SEQ ID NO: 1 or at nucleotide 76 of a sequence comprising at least 95%, 96%, 97%, 98% or more sequence identity to SEQ ID NO:1 and a second chromosome 4 having a Guanine, G, at nucleotide 76 of SEQ ID NO: 1 or at nucleotide 76 of a sequence comprising at least 95%, 96%, 97%, 98% or more sequence identity to SEQ ID NO:1), while a plant homozygous for wop1 (i.e. wop1/wop1) will have the genotype 'AA' for SNP1 (i.e. the plant comprises two chromosomes 4 which both have an Adenine, A, at nucleotide 76 of SEQ ID NO: 1 or at nucleotide 76 of a sequence comprising at least 95%, 96%, 97%, 98% or more sequence identity to SEQ ID NO:1). Or the diploid plant heterozygous for wop1 (i.e. wop1/WOP1) will be heterozygous for the SNP16a, i.e. will have the genotype 'AG' for SNP16a (i.e. the plant comprises one chromosome 4 having an Adenine, A, at nucleotide 428 of SEQ ID NO: 30 or at nucleotide 428 of a sequence comprising at least 95%, 96%, 97%, 98% or more sequence identity to SEQ ID NO:30 and a second chromosome 4 having a Guanine, G, at nucleotide 428 of SEQ ID NO: 30 or at nucleotide 428 of a sequence comprising at least 95%, 96%, 97%, 98% or more sequence identity to SEQ ID NO:30), while a plant homozygous for wop1 (i.e. wop1/wop1) will have the genotype 'AA' for SNP16a (i.e. the plant comprises two chromosomes 4 which both have an Adenine, A, at nucleotide 428 of SEQ ID NO:30 or at nucleotide 428 of a sequence comprising at least 95%, 96%, 97%, 98% or more sequence identity to SEQ ID NO:30). The same holds true for the other markers disclosed in Table 1. Likewise the SNP genotype of triploids homozygous for wop1 will be 'AAA' for SNP1 and/or for SNP16a, and distinguishable from the other genotypes 'AAG', 'AGG' and 'GGG'. The same holds true for tetraploids or other polyploids. So the SNP genotype of a tetraploid homozygous for wop1 will be 'AAAA' and distinguishable from the other genotypes 'AAAG', 'AAGG', AGGG' and 'GGGG'. In one aspect SNP16a is linked to the mutant wop1 allele and plants can be selected comprising an Adenine for SNP16a.

Plants and Plant Parts According to the Invention

In one embodiment a cultivated watermelon plant is provided, or a part thereof (such as a cell, a tissue, organ, fruit, etc.), comprising at least one copy of a mutant allele of a gene name WOP1, said mutant allele conferring facultative parthenocarpy when the mutant allele is in homozygous form. As mentioned above the WOP1 gene is located on chromosome 4 of the cultivated watermelon genome. The whole genome of watermelon has been sequenced, see Guo et al. 2013, Nature Genetics, page 51-60 and the sequence database is available for all chromosomes. In Table 1 above the SNP markers SNP1 (and SNP1a) to SNP24 are shown, including their physical position on chromosome 4. Thus, in one aspect the gene is located in a region starting at base pair 11.906.147 (SNP1) and ending at base pair 21.897.585 (SNP24) of chromosome 4. In another aspect the gene is located in a region starting at base pair 8.385.759 (SNP1a) and ending at base pair 21.897.585 (SNP24) of chromosome 4. In a further aspect the gene is located in a region starting at base pair 16.540.678 (SNP16) and ending at base pair 16.908.561 (SNP17).

In other words, a cultivated watermelon plant is provided, or a part thereof, comprising at least one copy of a mutant allele of a gene name WOP1, said mutant allele conferring facultative parthenocarpy when the mutant allele is in homozygous form, wherein said gene is located in a region starting at (nucleotide 76 of) SEQ ID NO: 1 (SNP1), or at (nucleotide 76 of) a sequence comprising at least 95%, 96%, 97%, 98% or 99% sequence identity to SEQ ID NO: 1 (SNP1), and ending at (nucleotide 76 of) SEQ ID NO: 24 (SNP24) or at (nucleotide 76 of) a sequence comprising at least 95%, 96%, 97%, 98% or 99% sequence identity to SEQ ID NO: 24 (SNP24). In another aspect the gene is located in a region starting at (nucleotide 76 of) SEQ ID NO: 29 (SNP1a), or at (nucleotide 76 of) a sequence comprising at least 95%, 96%, 97%, 98% or 99% sequence identity to SEQ ID NO: 29 (SNP1a), and ending at (nucleotide 76 of) SEQ ID NO: 24 (SNP24) or at (nucleotide 76 of) a sequence comprising at least 95%, 96%, 97%, 98% or 99% sequence identity to SEQ ID NO: 24 (SNP24). In further aspect the gene is located in a region starting at (nucleotide 76 of) SEQ ID NO: 16 (SNP16), or at (nucleotide 76 of) a sequence comprising at least 95%, 96%, 97%, 98% or 99% sequence identity to SEQ ID NO: 16 (SNP16), and ending at (nucleotide 76 of) SEQ ID NO: 17 (SNP17) or at (nucleotide 76 of) a sequence comprising at least 95%, 96%, 97%, 98% or 99% sequence identity to SEQ ID NO: 17 (SNP17).

In one aspect the mutant allele is a mutant allele of the gene which encodes the WOP1 protein of SEQ ID NO: 32 or a protein comprising at least 95%, 96%, 97% or 98% sequence identity to SEQ ID NO: 32 (wild type functional protein), whereby the mutant allele has a reduced expression or no expression, or whereby the mutant allele encodes a mutant WOP1 protein comprising one or more amino acids replaced, inserted or deleted compared to the wild type protein. In one embodiment the one or more amino acid replacements, insertions or deletions comprise or consist of the replacement, insertion or deletion of one or more amino acids in one or both of the conserved domains. The mutant protein has a reduced-function or loss-of-function compared to the wild type protein (and thus compared to a wild type plant comprising the wild type WOP1 gene), preferably the plant cell or plant comprising the mutant allele in homozygous form is facultative parthenocarpic.

When referring herein to a SNP nucleotide or SNP genotype at a specific nucleotide position, e.g. at nucleotide 76 of SEQ ID NO: 1, "or at nucleotide 76 of a sequence comprising at least 95%, 96%, 97%, 98% or 99% sequence identity to the SEQ ID NO", this means that the SNP nucleotide or SNP genotype is present in a variant sequence at a nucleotide corresponding to the same nucleotide (e.g. corresponding to nucleotide 76 of SEQ ID NO: 1) in the variant sequence, i.e. in a sequence comprising at least 95%, 96%, 97%, 98% or 99% sequence identity to the mentioned SEQ ID NO. It may for example be that the variant sequence is one or a few nucleotides shorter, but when one pairwise aligns the variant sequence with the mentioned SEQ ID NO, one can see which nucleotide of the variant sequence corresponds to the same nucleotide. In the variant sequence this may for example be nucleotide number 75 or 77 of that variant sequence which corresponds to nucleotide 76 of the mentioned sequence.

In one aspect a cultivated watermelon plant is provided, or a part thereof, comprising at least one copy of a mutant allele of a gene name WOP1, said mutant allele conferring facultative parthenocarpy when the mutant allele is in homozygous form, wherein said gene is located between SEQ ID NO: 1 (comprising SNP1), or a sequence comprising at least 95%, 96%, 97%, 98% or 99% sequence identity to SEQ ID NO: 1, and SEQ ID NO: 24 (comprising SNP24) or a sequence comprising at least 95%, 96%, 97%, 98% or 99% sequence identity to SEQ ID NO: 24. In another aspect said gene is located between SEQ ID NO: 29 (comprising SNP1a), or a sequence comprising at least 95%, 96%, 97%, 98% or 99% sequence identity to SEQ ID NO: 29, and SEQ ID NO: 24 (comprising SNP24) or a sequence comprising at least 95%, 96%, 97%, 98% or 99% sequence identity to SEQ ID NO: 24.

In a different aspect, the gene is located in a region starting at base pair 14.402.485 (SNP3) and ending at base pair 18.942.612 (SNP23) of chromosome 4.

In other words, a cultivated watermelon plant is provided, or a part thereof, comprising at least one copy of a mutant allele of a gene name WOP1, said mutant allele conferring facultative parthenocarpy when the mutant allele is in homozygous form, wherein said gene is located in a region starting at nucleotide 76 of SEQ ID NO: 3 (SNP3), or at nucleotide 76 of a sequence comprising at least 95%, 95%, 96%, 97%, 98% or 99% sequence identity to SEQ ID NO: 3 (SNP3), and ending at nucleotide 81 of SEQ ID NO: 23 (SNP23) or at nucleotide 81 of a sequence comprising at least 95%, 95%, 96%, 97%, 98% or 99% sequence identity to SEQ ID NO: 23 (SNP23).

In a further aspect a cultivated watermelon plant is provided, or a part thereof, comprising at least one copy of a mutant allele of a gene name WOP1, said mutant allele conferring facultative parthenocarpy when the mutant allele is in homozygous form, wherein said gene is located between SEQ ID NO: 3 (comprising SNP3), or a sequence comprising at least 95% 95%, 96%, 97%, 98% or 99% sequence identity to SEQ ID NO: 3, and SEQ ID NO: 23 (comprising SNP23) or a sequence comprising at least 95%, 95%, 96%, 97%, 98% or 99% sequence identity to SEQ ID NO: 23.

In a further aspect a cultivated watermelon plant is provided, or a part thereof, comprising at least one copy of a mutant allele of a gene name WOP1, said mutant allele conferring facultative parthenocarpy when the mutant allele is in homozygous form, wherein said gene is located between SEQ ID NO: 16 (comprising SNP16), or a sequence comprising at least 95%, 96%, 97%, 98% or 99% sequence identity to SEQ ID NO: 16, and SEQ ID NO: 17 (comprising SNP17) or a sequence comprising at least 95%, 96%, 97%, 98% or 99% sequence identity to SEQ ID NO: 17. In another aspect the WOP1 gene is the gene encoding a protein of SEQ ID NO: 32 or a protein comprising at least 95%, 96%, 97% or 98% sequence identity to SEQ ID NO: 32.

The mutant allele is a mutation in an endogenous gene of cultivated watermelon. The existence of a gene conferring facultative parthenocarpy and the location of the gene to the defined region on chromosome 4 enables the skilled person to generate other de novo mutants in the gene, i.e. in other cultivated watermelon lines or varieties. Other lines and varieties have some variation in their genome, which is why the SNP genotype may be different in different genetic backgrounds and which is why SEQ ID NO: 1 to SEQ ID NO: 24 (and SEQ ID NO: 29) may not be 100% identical in other genetic backgrounds to the sequences provided herein, but may comprise at least 95%, 96%, 97%, 98% or 99% sequence identity to the sequences provided as SEQ ID NO:1 to SEQ ID NO: 24 (and SEQ ID NO: 29). Nonetheless, the skilled person can, without undue burden, generate plants according to the invention, e.g. by carrying out a method for identification of mutants in a mutant population, based e.g. on the phenotype, as described elsewhere herein and further analysing the genetic inheritance, mapping the mutation, or sequencing the chromosome 4 region, allelism testing, etc. to verify that the phenotype is caused by a mutation in the WOP1 gene located on chromosome 4 between SNP1 (or SNP1a) and SNP24, preferably between SNP3 and SNP23, more preferably between SNP16 and SNP17.

As mentioned above, as the WOP1 gene has been identified to be the gene encoding a protein of SEQ ID NO: 32 (wild type protein) in normal, non-parthenocarpic watermelon plants, other mutants than the one generated by the inventors (encoding the mutant protein of SEQ ID NO: 31) can be generated de novo. As natural variation may exist in the wild type functional WOP1 proteins, the wild type WOP1 protein need not be 100% identical to the protein of SEQ ID NO: 32, but may have less sequence identity, e.g. 95%, 96%, 97% or 98% when aligned pairwise over the entire length. In one aspect the conserved myb-like DNA binding SHAQKYF-class domain is however 100% identical to that of SEQ ID NO: 32, i.e. has the sequence of SEQ ID NO: 35, in such wild type variant proteins, so that WOP1 genes are encompassed comprising mutants in genes encoding WOP1 proteins which proteins comprise at least 95% sequence identity to SEQ ID NO: 32 when aligned over the entire length, and such proteins comprise the conserved myb-like DNA binding SHAQKYF-class domain of SEQ ID NO: 35.

In a further aspect the plant according to the invention is a cultivated watermelon plant or a part thereof, comprising at least one copy of a mutant allele of a gene name WOP1, said mutant allele conferring facultative parthenocarpy when the mutant allele is in homozygous form, wherein said gene is linked a nucleotide sequence selected from the group consisting of SEQ ID NO: 1 or a sequence comprising at least 95%, 96%, 97%, 98% or 99% sequence identity to SEQ ID NO: 1; SEQ ID NO: 2 or a nucleotide sequence comprising at least 95%, 96%, 97%, 98% or 99% sequence identity to SEQ ID NO: 2; SEQ ID NO: 3 or a nucleotide sequence comprising at least 95%, 96%, 97%, 98% or 99% sequence identity to SEQ ID NO: 3; SEQ ID NO: 4 or a nucleotide sequence comprising at least 95%, 96%, 97%, 98% or 99% sequence identity to SEQ ID NO: 4; SEQ ID NO: 5 or a nucleotide sequence comprising at least 95%, 96%, 97%, 98% or 99% sequence identity to SEQ ID NO: 5; SEQ ID NO: 6 or a nucleotide sequence comprising at least 95%, 96%, 97%, 98% or 99% sequence identity to SEQ ID NO: 6; SEQ ID NO: 7 or a nucleotide sequence comprising at least 95%, 96%, 97%, 98% or 99% sequence identity to SEQ ID NO: 7; SEQ ID NO: 8 or a nucleotide sequence comprising at least 95%, 96%, 97%, 98% or 99% sequence identity to SEQ ID NO: 8; SEQ ID NO: 9 or a nucleotide sequence comprising at least 95%, 96%, 97%, 98% or 99% sequence identity to SEQ ID NO: 9; SEQ ID NO: 10 or a nucleotide sequence comprising at least 95%, 96%, 97%, 98% or 99% sequence identity to SEQ ID NO: 10; SEQ ID NO: 11 or a nucleotide sequence comprising at least 95%, 96%, 97%, 98% or 99% sequence identity to SEQ ID NO: 11; SEQ ID NO: 12 or a nucleotide sequence comprising at least 95%, 96%, 97%, 98% or 99% sequence identity to SEQ ID NO: 12; SEQ ID NO: 13 or a nucleotide sequence comprising at least 95%, 96%, 97%, 98% or 99% sequence identity to SEQ ID NO: 13; SEQ ID NO: 14 or a nucleotide sequence comprising at least 95%, 96%, 97%, 98% or 99% sequence identity to SEQ ID NO: 14; SEQ ID NO: 15 or a nucleotide sequence comprising at least 95%, 96%, 97%, 98% or 99% sequence identity to SEQ ID NO: 15; SEQ ID NO: 16 or a nucleotide sequence comprising at least 95%, 96%, 97%, 98% or 99% sequence identity to SEQ ID NO: 16; SEQ ID NO: 30 or a nucleotide sequence comprising at least 95%, 96%, 97%, 98% or 99% sequence identity to SEQ ID NO: 30; SEQ ID NO: 17 or a nucleotide sequence comprising at least 95%, 96%, 97%, 98% or 99% sequence identity to SEQ ID NO: 17; SEQ ID NO: 18 or a nucleotide sequence comprising at least 95%, 96%, 97%, 98% or 99% sequence identity to SEQ ID NO: 18; SEQ ID NO: 19 or a nucleotide sequence comprising at least 95%, 96%, 97%, 98% or 99% sequence identity to SEQ ID NO: 19; SEQ ID NO: 20 or a nucleotide sequence comprising at least 95%, 96%, 97%, 98% or 99% sequence identity to SEQ ID NO: 20; SEQ ID NO: 21 or a nucleotide sequence comprising at least 95%, 96%, 97%, 98% or 99% sequence identity to SEQ ID NO: 21; SEQ ID NO: 22 or a nucleotide sequence comprising at least 95%, 96%, 97%, 98% or 99% sequence identity to SEQ ID NO: 22; SEQ ID NO: 23 or a nucleotide sequence comprising at least 95%, 96%, 97%, 98% or 99% sequence identity to SEQ ID NO: 23; SEQ ID NO: 24 or a nucleotide sequence comprising at least 95%, 96%, 97%, 98% or 99% sequence identity to SEQ ID NO: 24. In one aspect the mutant wop1 allele is linked to any one of the above sequences, or to the SNP present in those sequences, at a physical distance of 2.5 Mb or less, such as 2.0 Mb or less, 1.5 Mb or less, 1.0 Mb or less, 0.8 Mb or less, 0.5 Mb or less, 0.4 Mb or less, 0.3 Mb or less, 0.2 Mb or less, 0.1 Mb or less, 74 kb, 50 kb, 20 kb, 10 kb, 5 kb, 2 kb, 1 kb or less. In another aspect the mutant wop1 allele is linked to any one of the above sequences, or to the SNP present in those sequences, at a physical distance of 0.5 Mb or less, 0.4 Mb or less, 0.3 Mb or less, 0.2 Mb or less, 0.1 Mb or less, 74 kb, 50 kb, 20 kb, 10 kb, 5 kb, 2 kb, 1 kb or less. The mutant allele is located in the region of chromosome 4 starting at SNP1 (or at SNP1a) and ending at SNP24, preferably starting at SNP3 and ending at SNP23, as described elsewhere. The linkage can be determined using mapping e.g. fine mapping. Linkage can also be expressed in centiMorgans (cM), so in one aspect the wop1 allele is linked to any one of the above markers within a genetic distance of 5 cM or less, e.g. 4 cM, 3 cM, 2 cM, 1 cM or less.

In yet a further aspect the plant according to the invention is a cultivated watermelon plant or a part thereof, comprising at least one copy of a mutant allele of a gene name WOP1, said mutant allele conferring facultative parthenocarpy when the mutant allele is in homozygous form, wherein said gene is located between a pair of SNP markers, or between a pair of sequences comprising the markers, selected from the group consisting of SNP1a (or SEQ ID NO: 29) and SNP3 (or SEQ ID NO: 3); SNP1 (or SEQ ID NO: 1) and SNP3 (or SEQ ID NO:3); SNP2 (or SEQ ID NO: 2) and SNP4 (or SEQ ID NO: 4); SNP3 (or SEQ ID NO: 3) and SNP5 (or SEQ ID NO: 5); SNP4 (or SEQ ID NO: 4) and SNP6 (or SEQ ID NO: 6); SNP5 (or SEQ ID NO: 5) and SNP7 (or SEQ ID NO: 7); SNP6 (or SEQ ID NO: 6) and SNP8 (or SEQ ID NO: 8); SNP7 (or SEQ ID NO: 7) and SNP9 (or SEQ ID NO: 9); SNP8 (or SEQ ID NO: 8) and SNP10 (or SEQ ID NO: 10); SNP9 (or SEQ ID NO: 9) and SNP11 (or SEQ ID NO: 11); SNP10 (or SEQ ID NO: 10) and SNP12 (or SEQ ID NO: 12); SNP11 (or SEQ ID NO: 11) and SNP13 (or SEQ ID NO: 13); SNP12 (or SEQ ID NO: 12) and SNP14 (or SEQ ID NO: 14); SNP13 (or SEQ ID NO: 13) and SNP15 (or SEQ ID NO: 15); SNP14 (or SEQ ID NO: 14) and SNP16 (or SEQ ID NO: 16); SNP15 (or SEQ ID NO: 15) and SNP17 (or SEQ ID NO: 17); SNP16 (or SEQ ID NO: 16) and SNP18 (or SEQ ID NO: 18); SNP17 (or SEQ ID NO: 17) and SNP19 (or SEQ ID NO: 19); SNP18 (or SEQ ID NO: 18) and SNP20 (or SEQ ID NO: 20); SNP19 (or SEQ ID NO: 19) and SNP21 (or SEQ ID NO: 21); SNP20 (or SEQ ID NO: 20) and SNP22 (or SEQ ID NO: 22); SNP21 (or SEQ ID NO: 21) and SNP23 (or SEQ ID NO: 23); SNP22 (or SEQ ID NO: 22) and SNP24 (or SEQ ID NO: 24). As mentioned previously, when referring to SNP markers, this includes the SNP markers in variant genomic sequences, such as a sequence comprising at least 95% sequence identity to the SEQ ID NO comprising the SNP and, likewise, when referring to sequences this also includes variant genomic sequences, such as a sequence comprising at least 95% sequence identity to the SEQ ID NO.

In yet a further aspect the plant according to the invention is a cultivated watermelon plant or a part thereof, comprising at least one copy of a mutant allele of a gene name WOP1, said mutant allele conferring facultative parthenocarpy when the mutant allele is in homozygous form, wherein said gene is located between a pair of SNP markers, or between a pair of sequences comprising the markers, selected from the group consisting of SNP16 (or SEQ ID NO: 16) and SNP17 (or SEQ ID NO: 17).

In one aspect the mutant wop1 allele is the allele as present in, and as obtainable from, plants grown from seeds deposited under accession number NCIMB42533, or progeny thereof, e.g. F1, F2, F3 or further selfing progeny or BC1, BC2, BC3, etc., or DH progeny, or tetraploid or triploids (or other polyploids) made using the allele present in NCIMB42533. In plants and plant parts grown from seeds deposited under NCIMB42533, or progeny thereof, the wop1 allele is in one aspect detectable by SNP genotyping using one or more or all of SNP1 (or SNP1a) to SNP24, preferably one or more or all of SNP3 to SNP23, or a subset of these SNPs linked to wop1. In one aspect the subset of SNP markers linked to the mutant wop1 allele is one, or more or all of SNP1a, SNP1, SNP2, SNP12, SNP16, SNP16a, SNP19, SNP22 and SNP23. In one aspect especially SNP16a is linked to the mutant gene, as it is in fact present in the protein coding sequence of the mutant wop1 allele. As mentioned further above, the SNP nucleotide of SNP1 (or SNP1a) to SNP24 linked to the mutant wop1 allele as found in seeds deposited under NCIMB42533 is given in Table 1, in column 3, and the SNP nucleotide of SNP1 (or SNP1a) to SNP24 linked to the wild type WOP1 allele as found in seeds deposited under NCIMB42533 is given in Table 1, column 4. When genotyping plants or plant parts derived from NCIMB42533, the SNP genotype for one or more or all of SNP1 (or SNP1a) to SNP24, or for one or more or all of SNP3 to SNP23, or for one or more or all of a subset thereof, e.g. one or more or all of SNP1a, SNP1, SNP2, SNP12, SNP16, SNP16a, SNP19, SNP22 and SNP23, the genotype detected confirms whether the mutant wop1 allele and/or the wild type WOP1 allele is present, and how many copies are present of each. Especially genotyping for SNP16a is sufficient, as this SNP is in the coding sequence of the allele.

Thus, in one aspect the plant or plant part according to the invention comprises at least one (but optionally 2 in a homozygous diploid, 3 in a triploid or 4 in a tetraploid or even more in other polyploids) 'A' nucleotide for SNP1a, and/or at least one 'A' nucleotide for SNP1, and/or at least one 'T' nucleotide for SNP2, and/or at least one 'C' nucleotide for SNP3, and/or at least one 'C' nucleotide for SNP4, and/or at least one 'A' nucleotide for SNP5, and/or at least one 'C' nucleotide for SNP6, and/or at least one 'T' nucleotide for SNP7, and/or at least one 'G' nucleotide for SNP8, and/or at least one 'C' nucleotide for SNP9, and/or at least one 'A' nucleotide for SNP10, and/or at least one 'G' nucleotide for SNP11, and/or at least one 'A' nucleotide for SNP12, and/or at least one 'G' nucleotide for SNP13, and/or at least one 'A' nucleotide for SNP14, and/or at least one 'G' nucleotide for SNP15, and/or at least one 'A' nucleotide for SNP16, and/or at least one 'A' nucleotide for SNP16a, and/or at least one 'G' nucleotide for SNP17, and/or at least one 'C' nucleotide for SNP18, and/or at least one 'G' nucleotide for SNP19, and/or at least one 'T' nucleotide for SNP20, and/or at least one 'G' nucleotide for SNP21, and/or at least one 'G' nucleotide for SNP22, and/or at least one 'G' nucleotide for SNP23, and/or at least one 'C' nucleotide for SNP24. In one specific aspect the plant or plant part according to the invention comprises at least one (but optionally 2 in a homozygous diploid, 3 in a triploid or 4 in a tetraploid or even more in other polyploids) 'A' nucleotide for SNP16a.

In a further aspect the plant or plant part according to the invention comprises at least one (but optionally 2 in a homozygous diploid, 3 in a triploid or 4 in a tetraploid or even more in other polyploids) 'C' nucleotide for SNP3, and/or at least one 'C' nucleotide for SNP4, and/or at least one 'A' nucleotide for SNP5, and/or at least one 'C' nucleotide for SNP6, and/or at least one 'T' nucleotide for SNP7, and/or at least one 'G' nucleotide for SNP8, and/or at least one 'C' nucleotide for SNP9, and/or at least one 'A' nucleotide for SNP10, and/or at least one 'G' nucleotide for SNP11, and/or at least one 'A' nucleotide for SNP12, and/or at least one 'G' nucleotide for SNP13, and/or at least one 'A' nucleotide for SNP14, and/or at least one 'G' nucleotide for SNP15, and/or at least one 'A' nucleotide for SNP16, and/or at least one 'A' nucleotide for SNP16a, and/or at least one 'G' nucleotide for SNP17, and/or at least one 'C' nucleotide for SNP18, and/or at least one 'G' nucleotide for SNP19, and/or at least one 'T' nucleotide for SNP20, and/or at least one 'G' nucleotide for SNP21, and/or at least one 'G' nucleotide for SNP22, and/or at least one 'G' nucleotide for SNP23.

In yet a further aspect the plant or plant part according to the invention comprises at least one (but optionally 2 in a homozygous diploid, 3 in a triploid or 4 in a tetraploid or even more in other polyploids) 'A' nucleotide for SNP1a, and/or at least one 'A' nucleotide for SNP1, and/or at least one 'T' nucleotide for SNP2, and/or at least one 'A' nucleotide for SNP12, and/or at least one 'A' nucleotide for SNP16, and/or at least one 'A' nucleotide for SNP16a, and/or at least one 'G' nucleotide for SNP19, and/or at least one 'G' nucleotide for SNP22, and/or at least one 'G' nucleotide for SNP23.

In yet a further aspect the plant or plant part according to the invention comprises at least one (but optionally 2 in a homozygous diploid, 3 in a triploid or 4 in a tetraploid or even more in other polyploids) 'A' nucleotide for SNP16a, which is the mutation in the coding sequence of the mutant wop1 allele present in the deposited seeds.

The SNP markers described herein may be detected according to standard method. For example SNP markers can easily be detected using a KASP-assay (see world wide web at kpbioscience.co.uk) or other SNP genotyping assays. For developing a KASP-assay, for example 70 base pairs upstream and 70 base pairs downstream of the SNP can be selected and two allele-specific forward primers and one allele specific reverse primer can be designed. See e.g. Allen et al. 2011, Plant Biotechnology J. 9, 1086-1099, especially p097-1098 for KASP-assay method.

Thus, in one aspect, the SNP markers and the presence/absence of the SNP nucleotide associated with the wop1 allele is determined using a KASP assay, but equally other genotyping assays can be used. For example, a TaqMan SNP genotyping assay, a High Resolution Melting (HRM) assay, SNP-genotyping arrays (e.g. Fluidigm, Illumina, etc.) or DNA sequencing may equally be used.

Genotyping of diploid plants or plant parts (cells, leaves, DNA, etc.) can distinguish SNP genotypes, e.g. plants or parts comprising AA for SNP1 can be distinguished from plants or parts comprising AG for SNP1 in their genome. Genotyping of tetraploid plants or plant parts (cells, leaves, DNA, etc.) can be done in the same way as for diploids, using for example a KASP-assay to distinguish SNP genotypes, e.g. plants or parts comprising AAAA for SNP1 can be distinguished from plants or parts comprising other genotypes for SNP1, e.g. AGGG, AAGG, etc. in their genome. The same applies for triploids. Thus, genotyping of triploid plants or plant parts (cells, leaves, DNA, etc.) can be done in the same way, using for example a KASP-assay to distinguish SNP genotypes, e.g. plants or parts comprising AAA for SNP1 can be distinguished from plants or parts comprising AAG, AGG, GGG for SNP1 in their genome. The same also applies for other polyploids.

The skilled person can also derive the mutant wop1 gene from seeds deposited under NCIMB42533 without deriving any of the SNP nucleotides/genotypes indicated in Table 1, column 3 from the deposited seeds. This can for example be done by finding other markers close to the wop1 allele and using such markers to select for the presence of the wop1 allele. In that way the mutant allele can be crossed into any different genetic background without transferring all the SNP markers of the deposited seeds, i.e. without transferring the chromosome 4 region around the wop1 allele, e.g. only SNP16a may be transferred to progeny. Similarly, phenotypic selection can be used to cross the mutant wop1 allele into any different genetic background than the genetic background of NCIMB42533.

Thus in one aspect a cultivated watermelon plant or plant part is provided comprising at least one copy of the wop1 allele in its genome, said allele conferring facultative parthenocarpy when it is in homozygous form, wherein said allele is obtainable (derivable; the allele is the allele as present in) seeds deposited under accession number NCIMB42533, e.g. by crossing plants grown from the seeds comprising the wop1 allele (preferably in homozygous form) with another watermelon plant, such as a breeding line or variety, e.g. comprising only the wild type WOP1 allele. The F1 will then comprise wop1 in heterozygous form and can be e.g. selfed and/or backcrossed to the breeding line or variety, to introduce the wop1 allele on chromosome 4 of that breeding line or variety. Alternatively, the same mutant allele as present in the deposited seed can be generated and/or selected for by the skilled person, e.g. in a different watermelon background, optionally even in a variant of the WOP1 gene. Thus the mutant allele may comprise a replacement of the serine of amino acid 143 in a protein which comprises at least 95%, 96%, 97% or 98% sequence identity to SEQ ID NO: 32. Optionally this protein comprises the conserved domain of SEQ ID NO: 35.

As mentioned, also other mutants in the WOP1 gene can be generated, which also confer facultative parthenocarpy when in homozygous form.

Thus in one aspect the invention encompasses a plant or plant part comprising at least one copy of a mutant allele of a gene name WOP1, wherein said gene is the gene encoding a protein of SEQ ID NO: 32, or a protein comprising at least 95%, 96%, 97% or 98% sequence identity to SEQ ID NO: 32, said mutant allele conferring facultative parthenocarpy when the mutant allele is in homozygous form. In one aspect the invention encompasses a plant or plant part comprising at least one copy of a mutant allele of a gene name WOP1 encoding a protein of SEQ ID NO: 32, or a protein comprising at least 95%, 96%, 97% or 98% sequence identity to SEQ ID NO: 32 and whereby said protein comprises the conserved domain of SEQ ID NO: 35, said mutant allele conferring facultative parthenocarpy when the mutant allele is in homozygous form.

A mutant allele of a WOP1 protein-encoding gene causes a plant to produce seedless fruits in the absence of pollination and seeded fruits in the presence of pollination, when the plant is homozygous for the mutant allele. Concerning the embodiments of the invention, the mutation in the mutant allele of a WOP1 protein-encoding gene can be any mutation, including deletions, truncations, insertions, point mutations, nonsense mutations, missense or non-synonymous mutations, splice-site mutations, frame shift mutations and/or mutations in regulatory sequences. In one aspect the mutation in the mutant allele of a WOP1 protein-encoding gene is a point mutation. The mutation can occur in a DNA sequence comprising the coding sequence of a WOP1 protein-encoding gene or in a RNA sequence encoding a WOP1 protein or it can occur in the amino acid of a WOP1 protein. Concerning a DNA sequence of a WOP1 protein-encoding gene the mutation can occur in the coding sequence or it can occur in non-coding sequences like 5'- and 3'-untranslated regions, promoters, enhancers etc. of a WOP1 protein-encoding gene. In respect to RNA encoding a WOP1 protein the mutation can occur in the pre-mRNA or the mRNA. In one aspect the mutant allele results in the protein having a loss-of-function or decrease of function due to one or more amino acids being replaced, inserted and/or deleted, for example resulting in one or more amino acids being replaced, inserted or deleted in the conserved myb-like DNA binding SHAQKYF-class domain or in the SHAQKYF domain. For example, truncation of the protein to cause deletion of either or both of these domains, or a part of either of these domains, will result in a loss of function or decrease of function of the protein. Thus, stop codon mutations e.g. in the N-terminal part (amino acid 1 to 96 of SEQ ID NO: 32 or a sequence comprising at least 95% sequence identity to SEQ ID NO: 32) or in one of the conserved domains result in truncated proteins having a reduced function or loss of function. Likewise amino acid insertions, deletions or replacements in the N-terminal part or one of the conserved domains can result in a protein having a reduced function or loss of function. Examples of amino acid replacements in the N-terminal part of the protein are E4 (amino acid 4 of SEQ ID NO: 32, Glutamic acid, e.g. to Leucine), S6 (amino acid 6 of SEQ ID NO: 32, Serine, e.g. to Leucine), E14 (amino acid 14 of SEQ ID NO: 32, Glutamic acid, e.g. to Leucine), P32 ((amino acid 32 of SEQ ID NO: 32, Proline, e.g. to Leucine), A35 (amino acid 35 of SEQ ID NO: 32, Alanine, e.g. to Valine), S54 (amino acid 54 of SEQ ID NO: 32, Serine, e.g. to phenylalanine), P56 (amino acid 56 of SEQ ID NO: 32, Proline, e.g. to Leucine), L57 (amino acid 57 of SEQ ID NO: 32, Leucine, e.g. to Histidine). Examples of amino acid replacements in the conserved domain are P104 (amino acid 104 of SEQ ID NO: 32, Proline, e.g. to Leucine) and S143 (amino acid 143 of SEQ ID NO: 32, Serine, e.g. to. Asparagine).

A further embodiment of the invention therefore concerns plant cells or plants according to the invention comprising a mutant allele of a WOP1 protein-encoding gene characterized in that the mutant allele comprises or effects one or more of the mutations selected from the group consisting of
a) a deletion, truncation, insertion, point mutation, nonsense mutation, missense or non-synonymous mutation, splice-site mutation, frame shift mutation in the genomic sequence;
b) a mutation in one or more regulatory sequences;
c) a deletion, truncation, insertion, point mutation, nonsense mutation, missense or non-synonymous mutation, splice-site mutation, frame shift mutation in the coding sequence;
d) a deletion, truncation, insertion, point mutation, nonsense mutation, missense or non-synonymous mutation, splice-site mutation, frame shift mutation in the pre-mRNA or mRNA; and/or
e) a deletion, truncation, insertion or replacement of one or more amino acids in the WOP1 protein.

In one aspect the mutant allele results in reduced expression or no expression of the WOP1 gene or the mutant allele encodes a protein having a decreased function or a loss-of-function.

Reduced expression or no expression means that there is a mutation in a regulatory region of the WOP1 gene, such as the promoter, whereby reduced mRNA transcript or no mRNA transcript of the WOP1 allele is being made, compared to plants and plant parts comprising a wild type WOP1 allele. The decrease in the expression can, for example, be determined by measuring the quantity of mRNA transcripts encoding WOP1 protein, e.g. using Northern blot analysis or RT-PCR. Here, a reduction preferably means a reduction in the amount of RNA transcripts by at least 50%, in particular by at least 70%, optionally by at least 85% or by at least 95%, or even by 100% (no expression) compared to the plant or plant part comprising a wild type WOP1 gene. Expression can be analysed e.g. in young leaf tissue or ovary tissue, see e.g. Examples.

In one aspect the protein comprising one or more amino acids replaced, inserted or deleted compared to the wild type protein. Thus, for watermelon, one or more amino acids are inserted, deleted or replaced compared to the wild type WOP1 protein of SEQ ID NO: 32 or a wild type WOP1 protein comprising at least 95%%, 96%, 97% or 98% sequence identity to SEQ ID NO: 32; for cucumber, one or more amino acids are inserted, deleted or replaced compared to the wild type WOP1 protein of SEQ ID NO: 33 or a wild type WOP1 protein comprising at least 95%%, 96%, 97% or 98% sequence identity to SEQ ID NO: 33; for melon, one or more amino acids are inserted, deleted or replaced compared to the wild type WOP1 protein of SEQ ID NO: 34 or a wild type WOP1 protein comprising at least 95%%, 96%, 97% or 98% sequence identity to SEQ ID NO: 34; whereby the mutant protein has reduced function or loss of function compared to the wild type protein and thus results in facultative parthenocarpy when the mutant allele is present in homozygous form in a diploid plant.

In one aspect the WOP1 protein comprises the conserved myb-like DNA binding domain SHAQKYF-class of SEQ ID NO: 35. Thus in one aspect the mutant allele is a mutant allele of the gene WOP1, which gene encodes a protein of SEQ ID NO: 32 (watermelon) or of SEQ ID NO: 33 (cucumber) or of SEQ ID NO: 34 (melon), or a protein comprising at least 95%, 96%, 97% or 98% sequence identity to SEQ ID NO: 32, SEQ ID NO: 33 or SEQ ID NO: 34, and whereby the protein comprises the conserved domain of SEQ ID NO: 35.

The myb-like DNA binding domain SHAQKYF-class of SEQ ID NO: 35 is found in the watermelon WOP1 protein of SEQ ID NO: 32 at amino acid 97 to 150, and comprises the SHAQKYF domain at amino acid 143 to 150. Thus in one aspect the wild type WOP1 gene encodes a wild type protein comprising a myb-like DNA binding domain SHAQKYF-class which is 100% identical to amino acids 97 to 150 of SEQ ID NO: 32. The myb-like DNA binding domain SHAQKYF-class of SEQ ID NO: 35 is found in the cucumber WOP1 protein of SEQ ID NO: 33 at amino acid 97 to 150, and comprises the SHAQKYF domain at amino acid 143 to 150. Thus in one aspect the wild type WOP1 gene encodes a wild type protein comprising a myb-like DNA binding domain SHAQKYF-class which is 100% identical to amino acids 97 to 150 of SEQ ID NO: 33. The myb-like DNA binding domain SHAQKYF-class of SEQ ID NO: 35 is found in the melon WOP1 protein of SEQ ID NO: 34 at amino acid 97 to 150, and comprises the SHAQKYF domain at amino acid 143 to 150. Thus in one aspect the wild type WOP1 gene encodes a wild type protein comprising a myb-like DNA binding domain SHAQKYF-class which is 100% identical to amino acids 97 to 150 of SEQ ID NO: 34.

In one aspect the mutant allele comprises a mutation whereby one or more amino acids in said myb-like DNA binding domain SHAQKYF-class of SEQ ID NO: 35 (i.e. of amino acids 97 to 150 of SEQ ID NO: 32, SEQ ID NO: 33 and SEQ ID NO: 34) are replaced, inserted or deleted.

In a preferred aspect one or more amino acids of the SHAQKYF domain, i.e. amino acids 47 to 54 of SEQ ID NO: 35 (i.e. of amino acids 143 to 150 of SEQ ID NO: 32, SEQ ID NO: 33 and SEQ ID NO: 34), are replaced, inserted or deleted.

When amino acids from one amino acid to another amino acid are mentioned herein this includes the start/first and end/last amino acid mentioned.

In a specific aspect at least one amino acid of amino acids of SEQ ID NO: 35 is replaced by another amino acid, preferably amino acid 47 is not a Serine and/or amino acid 8 is not a Proline. In one aspect the Serine at amino acid 47 is replaced by an Asparagine and/or the Proline of amino acid 8 is replaced by a Leucine.

In a specific aspect at least one amino acid of amino acids 47 to 54 of SEQ ID NO: 35 is replaced by another amino acid, preferably amino acid 47 is not a Serine. In one aspect the Serine is replaced by an Asparagine.

In one aspect the invention encompasses a plant or plant part comprising at least one copy of a mutant allele of a gene name WOP1 encoding a protein of SEQ ID NO: 32 (in watermelon), SEQ ID NO: 33 (in cucumber) or SEQ ID NO: 34 (in melon), or a protein comprising at least 95%, 96%, 97% or 98% sequence identity to SEQ ID NO: 32, SEQ ID NO: 33 or SEQ ID NO: 34, respectively, said mutant allele conferring facultative parthenocarpy when the mutant allele is in homozygous form, whereby the protein comprises at least one amino acid substitution in the myb-like DNA binding domain SHAQKYF-class of SEQ ID NO: 35, for example the Serine at amino acid 143 of SEQ ID NO: 32, or at amino acid 143 of SEQ ID NO: 33 or of SEQ ID NO: 34, is replaced by a different amino acid, e.g. an Asparagine, and/or the Proline at amino acid 104 is replaced by a different amino acid, e.g. a Leucine.

The plants and plant parts comprising at least one copy of a mutant wop1 allele may be plants of the family Cucurbitaceae, especially cultivated species such as cucumber (*Cucumis sativus*), melon (*Cucumis melo*) and watermelon (*Citrullus lanatus*). Also plants and plant parts of the family Cucurbitaceae, especially cucumber, melon and watermelon, comprising two copies of a mutant wop1 allele are encompassed herein, whereby diploid plants comprising two copies of the mutant wop1 allele results in plants exhibiting the phenotype of facultative parthenocarpy.

In one aspect the mutant wop1 allele is heterozygous in a diploid plant cell or plant, e.g. in a diploid watermelon, cucumber or melon plant. In another aspect the mutant wop1 allele is homozygous in a diploid plant cell or plant.

The plant cells and plants are preferably cultivated plants, such as elite breeding lines or varieties, and not wild plants. Cucumber may be any type of cucumber, such as long cucumber, pickling cucumber, slicing cucumber, etc. Likewise melon may be any type of melon (Galia, Piel de Sapo, Cantaloupe, honeydew, etc.) and watermelon may be any type of watermelon.

Watermelon plants, and parts thereof, which comprises at least one copy of the mutant wop1 allele, may be diploid, tetraploid or triploid. In another aspect it may be another polyploid, e.g. a pentaploid, hexaploid, heptaploid, octaploid, etc. A tetraploid plant comprising four copies of wop1 can for example be used to make an octaploid, by doubling the chromosomes. Crossing such an octoploid with a diploid homozygous for wop1 will result in a pentaploid comprising five copies of wop1. In one aspect the polyploidy watermelon plant comprises at least one copy of the mutant wop1 allele, but it may also comprise more copies, e.g. in a preferred aspect it is homozygous for wop1 and lacks the wild type WOP1 allele. Thus all chromosomes 4 comprise the mutant wop1 allele.

A diploid plant may thus have the genotype wop1/WOP1 (heterozygous for the mutant allele) or wop1/wop1 (homozygous for the mutant allele). In one aspect the diploid plant comprising the wop1 allele in homozygous form is a double haploid plant (DH), e.g. a double haploid watermelon, cucumber or melon plant or plant cell or plant part.

A triploid watermelon plant may have the genotype wop1/WOP1/WOP1 or wop1/wop1/WOP1 or wop1/wop1/wop1. The triploid plant with genotype wop1/WOP1/WOP1 can be made by crossing a wild type female tetraploid (WOP1/WOP1/WOP1/WOP1) with a diploid male homozygous for the mutant allele (wop1/wop1). The triploid plant with genotype wop1/wop1/WOP1 can be made by crossing a female tetraploid (wop1/wop1/wop1/wop1) with a diploid male homozygous for the wild type allele (WOP1/WOP1).

A tetraploid watermelon plant may have the genotype wop1/WOP1/WOP1/WOP1 or wop1/wop1/WOP1/WOP1 or wop1/wop1/wop1/WOP1 or wop1/wop1/wop1/wop1. The genotypes wop1/wop1/WOP1/WOP1 can be made by doubling the chromosomes of a diploid wop1/WOP1. The genotypes wop1/wop1/wop1/wop1 can be made by doubling the chromosomes of a diploid wop1/wop1. The other two genotypes, wop1/WOP1/WOP1/WOP1 and wop1/wop1/wop1/WOP1 can for example be made by crossing two tetraploids of genotype wop1/wop1/WOP1/WOP1 and identifying the genotypes in the progeny.

In one aspect the watermelon plant is homozygous for wop1, in another aspect it is heterozygous for wop1. In one aspect it is an inbred line or a variety. In a further aspect it is an F1 hybrid.

Seeds from which any of the watermelon plants, cucumber plants or melon plants described can be grown are also encompassed herein, as are parts of such a plant, such as seedless fruits produced in the absence of pollination, flowers, cells, roots, rootstocks, scions, leaves, stems, vegetative propagations, cuttings, seed propagations (e.g. selfings) and also in vitro cell- or tissue cultures, as well as pollen, ovaries, etc. are encompassed herein.

Diploid Watermelon, Cucumber and Melon Plants Comprising a Mutant wop1 Allele

In one aspect the watermelon plant or cucumber or melon plant is a diploid line (e.g. an inbred line) or variety, comprising at least one mutant copy of wop1, preferably two mutant copies (i.e. is homozygous for wop1). When preventing pollination of the female flowers, the diploid plant homozygous for wop1 will produce fruits which are seedless. When pollination does occur, the fruits will be seeded.

To prevent pollination one can, for example, grow the plant in an insect free environment. However, one can also produce a diploid plant which are male sterile. Thus, in one aspect of the invention a diploid plant is provided which is homozygous for wop1, and which additionally is male sterile. Male sterility is the failure of plants to produce functional anthers, pollen, or male gametes. Several male sterility genes have been identified in watermelon, including the ms-1 gene. The ms-1 nuclear gene controls male sterility and, in plants with an ms-1 gene in homozygous form (ms-1 is recessive), the normal development of anthers is hindered while female flower development is normal. The gene eliminates pollen production. Markers for the ms-1 gene and plants comprising the gene are described in EP2959771 and the database PINTO mentions that variety Bonta or Bonta F1 of Seminis is a plant according to this patent. The ms-1 gene has also been described in Zhang et al. 1996 (HortScience 31(1): 123-126). The ms-1 gene is on chromosome 6 of watermelon and can therefore easily be combined with wop1 on chromosome 4. In melon also male sterility genes exist. In cucumber the mutant wop1 allele can be combined with gynociousness, i.e. production of female, pistillate flowers.

Therefore, in one aspect the diploid plant and plant part according to the invention is male sterile and/or comprises a male sterility gene. If the male sterility gene is a recessive gene, the plant and plant part preferably comprises the gene in homozygous form. In one aspect the watermelon plant comprises the ms-1 gene, preferably in homozygous form. Thus, in one aspect the diploid watermelon plant comprises on chromosome 4 the mutant wop1 gene in homozygous form (wop1/wop1) and further comprises a male sterility gene, e.g. ms-1, in homozygous form, e.g. if the male sterility gene is recessive (e.g. ms-1/ms-1) or optionally in heterozygous form if the male sterility is dominant One preferred plant is a diploid plant homozygous for wop1 and homozygous for ms-1.

A further way of ensuring that plants according to the invention, especially diploid watermelon plants, produce seedless fruits at all times (not only in the absence of pollination) is to combine the wop1 gene in homozygous form with a gene conferring stenospermocarpy, so that if pollination does occur the fruits will be seedless despite pollination. In one aspect the stenospermocarpy gene is the recessive gene called emb1. The wild type and mutant Emb1 gene has been described in co-pending application EP16171462.1. The Emb1 gene encodes a cyclin SDS like protein. When the mutant allele emb1 is in homozygous form, stenospermocarpy results. "Stenospermocarpy" means that induction of fruit set and development requires pollination but without the fruits producing mature or viable seeds. Mature or viable seeds are not developed in stenospermocarpic plants due to arrested seed development or degradation of ovules and/or embryos and/or endosperm or abortion of the ovules and/or embryos and/or endosperm before maturity is reached. Thus, when diploid plants homozygous for a mutant emb1 allele (emb1/emb1) are self-pollinated or pollinated by pollen from another plant, they produced seedless, diploid fruits.

Thus, in one aspect the diploid watermelon plant comprises on chromosome 4 the wop1 gene in homozygous form (wop1/wop1) and further comprises a stenospermocarpy gene, e.g. emb1, in homozygous form, e.g. if the stenospermocarpy gene is recessive (e.g. emb1/emb1) or optionally in heterozygous form if the stenospermocarpy gene is dominant. One preferred plant is a diploid plant homozygous for wop1 and homozygous for emb1.

One mutant allele of emb1 can be obtained from the watermelon seeds being heterozygous or homozygous for the mutant allele of the cyclin SDS like protein encoding gene (also referred to as Emb1 gene), deposited by Nunhems B.V. under NCIMB 42532. Of these seeds 25% contain the mutant allele (see mRNA of SEQ ID NO: 27) encoding a mutant protein of SEQ ID NO: 28. The wild type allele of the Emb1 gene can be obtained from the watermelon seeds being heterozygous or homozygous for the wild type cyclin SDS like protein encoding gene, deposited by Nunhems B.V. under NCIMB 42532. Of these seeds 25% contain the wild type allele of SEQ ID NO: 25 in homozygous form, encoding the wild type protein of SEQ ID NO: 26. Other mutant alleles of the Emb1 gene can be generated de novo, e.g. by mutagenesis or by other methods known to the skilled person. The genomic Emb1 nucleotide sequence shown under SEQ ID NO: 25 encodes a wild type cyclin SDS like protein of *Citrullus lanatus* having the amino acid sequence as shown under SEQ ID NO: 26. The mRNA sequence shown under SEQ ID NO: 27, and the mutant protein shown under SEQ ID NO: 28, is of the mutant emb1 allele found in seeds deposited under NCIMB42532.

A mutant allele of emb1 causes a plant to be male fertile but producing seedless fruits, when the plant is homozygous for the mutant allele. The mutation in the Emb1 gene can be any mutation, including deletions, truncations, insertions, point mutations, nonsense mutations, missense or non-synonymous mutations, splice-site mutations, frame shift mutations and/or mutations in regulatory sequences. Preferably the mutation is a point mutation and/or splice-site mutation. The mutation can occur in a DNA sequence comprising the coding sequence of a cyclin SDS like protein encoding gene (Emb1 gene) or in a RNA sequence encoding a cyclin SDS like protein or it can occur in the amino acid of a cyclin SDS like protein (or Emb1 protein). Concerning a DNA sequence of a cyclin SDS like protein encoding gene the mutation can occur in the coding sequence (cds, composed of the exons) or it can occur in non-coding sequences like 5'- and 3'-untranslated regions, introns, promoters, enhancers etc. of a cyclin SDS like protein encoding gene. In respect to RNA encoding a cyclin SDS like protein the mutation can occur in the pre-mRNA or the mRNA.

Diploid *Citrullus lanatus* seeds of plants segregating for a mutant allele of a cyclin SDS like protein encoding gene have been deposited by Nunhems B.V. under the Budapest Treaty under accession No. NCIMB 42532 at NCIMB Ltd., Ferguson Building, Craibstone Estate Bucksburn Aberdeen AB21 9YA, Scotland, UK on 27 Jan. 2016. For the seed deposit the allele of the cyclin SDS like protein encoding gene was designated emb1.

The deposited seeds were obtained from a self-pollinated back-cross of a plant homozygous for the emb1 mutant allele with plants homozygous for the emb1 wild type allele. Therefore 25% of the deposited seeds are homozygous for the emb1 mutant allele and produce seedless fruits, 50% are heterozygous for the mutant allele and 25% are homozygous for the wild type allele, encoding the wild type cyclin SDS like protein.

In one aspect the invention, therefore, relates to a diploid watermelon plant or plant part comprising at least one copy of the mutant wop1 allele, preferably two copies, and at least one copy of a mutant emb1 allele, preferably two copies of a mutant emb1 allele. In one aspect the mutant emb1 allele is the allele found in seeds deposited under NCIMB 42532.

In one aspect the mutant wop1 allele is the allele found in seeds deposited under NCIMB42533 or a different mutant wop1 allele as described.

Seeds from which such a diploid plant can be grown are also encompassed herein, as are parts of such a plant, such as diploid seedless fruits, flowers, leaves, stems, vegetative propagations, cells, cuttings, seed propagations (e.g. self-ings) and also in vitro cell- or tissue cultures, as well as pollen, ovaries, rootstocks, scions, etc. are encompassed herein. Thus, in one embodiment the diploid plant, or seeds from which the plant can be grown, or tissue or parts of the plant (pollen, anthers, ovules) comprises a mutant wop1 allele as described above, e.g. the mutant allele as found in seeds deposited under NCIMB42533 or a different mutant wop1 allele.

Tetraploid Watermelon Plants Comprising a Mutant wop1 Allele

Seedless triploid watermelon production involves using pollen from diploid male parent plants to fertilize flowers of tetraploid maternal parent plants. Pollination of the tetraploid flowers with diploid pollen leads to F1 seeds which are triploid (Kihara, 1951, Proceedings of American Society for Horticultural Science 58: 217-230; Eigsti 1971, Hort Science 6: 1-2). The triploid hybrid plants, grown from these F1 seeds, are self-infertile as they produce sterile pollen due to chromosome imbalance. The triploid hybrids, therefore, normally need to be pollinated by a diploid pollenizer to produce watermelon fruit.

However, according to the present invention a triploid plant comprising three copies of a mutant wop1 gene produce fruits without pollination and there is no need anymore for a pollenizer plant being present.

In one aspect of the invention therefore both tetraploid plants, comprising four copies of a recessive wop1 allele, for use as a female parent, and diploid plants comprising two copies of a recessive wop1 allele, for use as a male parent, are provided, as well as triploid F1 hybrids (comprising three copies of a mutant wop1 allele) produced by crossing the diploid male parent with the tetraploid female parent.

To make such a tetraploid plant, any of the diploid plants described above, which are preferably homozygous for wop1, may be used as starting material to generate tetraploid plants. Chromosome doubling techniques known to the skilled person may be used to generate a tetraploid plant from such diploid plants. For example Noh et al. (2012) Hort. Environ. Biotechnol. 53(6):521-529, evaluated different methods of generating tetraploid watermelons. In all methods an antimitotic agent is used, such as colchicine, dinitoalanine, or oryzalin, in order to induce chromosome doubling. Optionally tissue culture may be used to generate tetraploid plants from plant parts. To verify that plants are tetraploid chromosome number can be confirmed. Ploidy can be easily determined by chromosome counting or flow cytometry or other known methods (Sari et al. 1999, Scientia Horticulturae 82: 265-277, incorporated herein by reference).

Thus, in one aspect of the invention a tetraploid cultivated watermelon plant of the species Citrullus lanatus is provided, wherein said plant comprises four copies of a mutant wop1 allele (as described above), one on each of the four chromosomes 4. The wop1 allele is found in the region as described above, between one or more of the SNP markers as described further above and/or linked to one or more of the sequences SEQ ID NO: 1 (or SEQ ID NO: 29) to SEQ ID NO: 24 as described above.

All embodiments described for the mutant wop1 allele above apply equally to the tetraploid. So for example the tetraploid plant may comprise four copies of the wop1 allele as found in seeds deposited under NCIMB42533, or four copies of a different mutant wop1 allele as described further above.

Thus in one aspect the invention encompasses a tetraploid watermelon plant or plant part comprising one, two, three or four copies of a mutant allele of a gene name WOP1 encoding a protein of SEQ ID NO: 32, or a protein comprising at least 95%, 96%, 97% or 98% sequence identity to SEQ ID NO: 32 (said protein optionally comprising the conserved domain of SEQ ID NO: 35). The aspects regarding the mutant wop1 allele described above for diploid watermelon plants comprising one or two copies of a mutant wop1 allele apply to the tetraploid plants and plant parts. So, for example, in one aspect the mutant allele results in reduced expression or no expression of the WOP1 gene or the mutant allele encodes a protein having a decreased function or a loss-of-function.

In a specific aspect, the tetraploid watermelon plant or plant part comprises four copies of the allele encoding the mutant WOP1 protein of SEQ ID NO: 31.

In another specific aspect, the tetraploid watermelon plant or plant part comprises four copies of a different mutant wop1 allele, e.g. selected from the alleles described above.

Genotyping of tetraploid plants or plant parts (cells, leaves, DNA, etc.) can be done in the same way as for diploids, using for example a KASP-assay to distinguish SNP genotypes, e.g. plants or parts comprising AAAA for SNP1 can be distinguished from plants or parts comprising GAAA, GGAA, GGGA or GGGG for SNP1 in their genome. Plants and plant parts comprising AAAA for SNP16a, i.e. four copies of SEQ ID NO: 30 encoding the mutant WOP1 protein of SEQ ID NO: 31, can equally be distinguished from the other genotypes.

In one aspect of the invention a tetraploid watermelon comprising at least one or two or three copies of the mutant wop1 allele (as described above), but preferably comprising four copies of the mutant wop1 allele (as described above) is provided. Preferably the watermelon plant is a tetraploid inbred female line, suitable as a parent for F1 hybrid seed production.

The generation of the tetraploid female inbred line can be carried out by using a diploid plant, comprising one or preferably two copies of the wop1 allele in order to double the chromosomes and generate a tetraploid plant. E.g. a diploid inbred line homozygous for wop1 can be used to generate the tetraploid plant. For example plants grown from seeds deposited under NCIMB42533 comprising two copies of a mutant wop1 allele can be used.

A tetraploid plant comprising four copies of a mutant wop1 allele (i.e. being homozygous for wop1) will express the phenotype, i.e. be facultative parthenocarpic.

Seeds from which such a tetraploid plant can be grown are also encompassed herein, as are parts of such a plant, such as tetraploid seedless fruits produced in the absence of pollination, flowers, leaves, stems, cuttings, vegetative propagations, cells, seed propagations (e.g. selfings) and also in vitro cell- or tissue cultures, as well as pollen, ovaries, rootstocks, scions, etc. are encompassed herein. Thus, in one embodiment the tetraploid plant, or seeds from which the plant can be grown, or tissue or parts of the plant (pollen, anthers, ovules) comprises a mutant wop1 allele as described above, e.g. the mutant allele as found in seeds deposited under NCIMB42533 or another mutant wop1 allele.

A tetraploid can comprise different mutant wop1 alleles, e.g. two mutant wop1 alleles encoding a truncated WOP1 protein and two mutant wop1 allele encoding a WOP1 protein having an amino acid substitution, e.g. Serine 143 of SEQ ID NO: 32 being replaced by Asparagine (mutant S143N). Such plants can for example be made by first making a diploid comprising different mutant wop1 alleles and then doubling the chromosomes of such diploid. In one aspect the tetraploid does, however, comprise four copies of the same mutant wop1 allele, i.e. the tetraploid is made from a diploid which is homozygous for the wop1 allele.

Triploid Watermelon Plants Comprising a Mutant wop1 Allele

In a further aspect triploid watermelon seeds, plants and plant parts comprising one, two or three copies of a mutant wop1 allele are provided, i.e. wop1/WOP1/WOP1 or wop1/wop1/WOP1 or wop1/wop1/wop1, respectively. Such triploids can be made as described above, and as shown in the Table 2 below:

TABLE 2

| | Female tetraploid parent | Male diploid parent | Genotype of F1 triploid seed produced by pollinating female tetraploid with pollen of male diploid |
|---|---|---|---|
| A | wop1/wop1/wop1/wop1 | wop1/wop1 | wop1/wop1/wop1 |
| B | wop1/wop1/wop1/wop1 | WOP1/WOP1 | wop1/wop1/WOP1 |
| C | WOP1/WOP1/WOP1/WOP1 | wop1/wop1 | WOP1/WOP1/wop1 |

In one aspect a tetraploid plant comprising four copies of a mutant wop1 allele is used as female parent and is pollinated with pollen of diploid male parent comprising two copies of a mutant wop1 allele and the seeds from the cross are harvested. These seeds are triploid and they comprise three copies of a mutant wop1 allele of the invention (Table 2, row A). Plants grown from these seeds produce seedless watermelon fruits (triploid fruits) without the need for pollination to induce fruit set. The triploid hybrid plants, grown from these F1 triploid seeds, are self-infertile as they produce sterile pollen due to chromosome imbalance. These seeds can thus be grown in production fields without the need for pollenizer plants. This is the first time that seedless triploid watermelon fruits can be produced in the absence of pollen and pollenizer plants.

In one aspect the triploid under A above comprises three identical mutant wop1 alleles, i.e. the female and male parents comprise the same mutant allele. However, in another aspect the female parent and the male parent may comprise different mutant wop1 alleles. For example the female parent may comprise four mutant wop1 allele encoding a truncated WOP1 protein and the male parent may comprise two mutant wop1 allele encoding a WOP1 protein having an amino acid substitution, e.g. Serine 143 of SEQ ID NO: 32 being replaced by Asparagine (mutant S143N), or the other way around.

The triploid, seedless fruits are preferably marketable. Preferably they have an average brix of at least 6.0, 7.0, 8.0 or preferably at least 9.0, preferably at least 10.0, more preferably at least 11.0. Fruits may be of any size, shape, color and rind pattern. Preferably fruit flesh color at maturity is uniform. In one aspect fruit flesh is red or dark red.

The average fruit weight of a triploid hybrid comprising wop1 in three copies may be equal to or above 2, 3, 4, 5, 6, 7, 8, 9, 10, 11, 12, 13 or 14 kg. In another embodiment average fruit weight of a triploid hybrid comprising wop1 in three copies may be equal to or less than 5 kg, e.g. 4, 3, 2, 1.5 or 1 kg or even less.

Seedless fruits may be of any shape (e.g. elongate, oval, blocky, spherical or round), fruit surface (furrow, smooth), flesh color (red, dark red, scarlet red, coral red, orange, salmon, pink, pinkish red, yellow, canary yellow or white), rind color (e.g. light green; dark green; green-striped with narrow, medium or wide stripes; grey types; with or without spotting; Golden yellow), rind thickness, rind toughness, rind pattern (e.g. striped, non-striped, netted), flesh structure/flesh firmness, lycopene and/or vitamin content, different sugar to acid ratios, fruit flavour, etc.

Thus, the mutant wop1 allele may be used to breed a range of seedless varieties, producing fruits of different shapes and sizes, etc. by traditional breeding. See Guner and Wehner 2004, Hort Science 39(6): 1175-1182, in particular pages 1180-1181 describing genes for fruit characteristics. Generally important breeding objectives are early maturity, high fruit yield, high internal fruit quality (good uniform color, high sugar, proper sugar: acid ratio, good flavor, high vitamin and lycopene content, firm flesh texture, non-fibrous flesh texture, freedom from defects such as hollow heart, rind necrosis, blossom-end rot or cross stitch and good rind characteristics and cracking-resistance).

Seeds from which such triploid F1 hybrid plants can be grown are one aspect of the invention.

Regarding triploid seeds and triploid plants comprising only one or two copies of a mutant wop1 allele of the invention (as shown in the Table 2 above, row B and C), the phenotype has not yet been tested, but these may also be suitable to produce seedless fruits without pollen and they may also be grown in a field without pollenizer plants. In any case, such triploid plants and seeds from which such plants can be grown are an aspect of the invention, as are parts thereof and triploid fruits produced by such plants. Preferably such triploid fruits are marketable. Preferably they have an average brix of at least 6.0, 7.0, 8.0 or preferably at least 9.0, preferably at least 10.0, more preferably at least 11.0. Fruits may be of any size, shape, color and rind pattern. Preferably fruit flesh color at maturity is uniform. In one aspect fruit flesh is red or dark red.

In one aspect the triploid plant of the invention is a vegetative propagation.

Also provided is a method for producing triploid hybrid watermelon seeds, wherein triploid plants grown from such seeds produce fruits in the absence of pollination, said method comprising:
(a) providing a facultative parthenocarpic diploid watermelon plant and a facultative parthenocarpic tetraploid plant (see e.g. Table 2 row A),
(b) allowing pollination of pistillate flowers of the tetraploid plant with pollen of the diploid plant, and
(c) harvesting seeds produced in the fruits of the tetraploid plant, and optionally
(d) drying the harvested seeds.

Optionally the dried and harvested F1 seeds are then packaged. They may also be treated prior to packaging. Thus packages or containers comprising or consisting of seeds obtained by the above method are an embodiment herein.

Also provided is a method for producing triploid hybrid watermelon seeds, said method comprising:
(a) providing a diploid watermelon plant lacking a mutant wop1 allele and a tetraploid plant comprising four copies of a mutant wop1 allele (see e.g. Table 2 row B), or providing a diploid watermelon plant homozygous for the mutant wop1 allele and a tetraploid plant lacking a mutant wop1 allele (e.g. Table 2 row C),
(b) allowing pollination of pistillate flowers of the tetraploid plant with pollen of the diploid plant, and
(c) harvesting seeds produced in the fruits of the tetraploid plant, and optionally
(d) drying the harvested seeds.

Optionally the dried and harvested F1 seeds are then packaged. They may also be treated prior to packaging. Thus packages or containers comprising or consisting of seeds obtained by the above method are an embodiment herein.

Seeds from which any the above triploid plants can be grown are also encompassed herein, as are parts of such a plant, such as triploid fruits, flowers, leaves, stems, cuttings, vegetative propagations, cells, seed propagations (e.g. selfings) and also in vitro cell- or tissue cultures, as well as pollen, ovaries, rootstocks, scions, etc. are encompassed herein. Thus, in one embodiment the triploid plant, or seeds from which the plant can be grown, or tissue or parts of the plant (pollen, anthers, ovules) comprises a mutant wop1 allele as described above, e.g. the mutant allele as found in seeds deposited under NCIMB42533 or another mutant wop1 allele as described above.

Vegetative Propagations and Cell or Tissue Cultures

The above diploid plants, tetraploid plants or triploid plants (or other polyploids) can also be reproduced vegetatively (clonally) and such vegetatively propagated plants, or 'vegetative propagations' are an embodiment of the invention. They can easily be distinguished from other watermelon plants by the presence of a mutant wop1 allele and/or phenotypically. The presence of one or more mutant wop1 alleles can be determined as described elsewhere herein.

Vegetative propagations can be made by different methods. For example one or more scions of a plant of the invention may be grafted onto a different rootstock, e.g. a biotic or abiotic stress tolerant rootstock.

Other methods include in vitro cell or tissue culture methods and regeneration of vegetative propagations from such cultures. Such cell or tissue cultures comprise or consist of various cells or tissues of a plant of the invention. In one aspect such a cell or tissue culture comprises or consists of vegetative cells or vegetative tissues of a plant of the invention.

In another aspect a cell or tissue culture comprises or consists of reproductive cells or tissues, such as anthers or ovules of a plant of the invention. Such cultures can be treated with chromosome doubling agents to make e.g. double haploid plants, or they can alternatively be used to make haploid plants (e.g. to make diploids from a tetraploid or to make haploids from a diploid).

An in vitro cell or tissue culture may, thus, comprise or consist of cells or protoplasts or plant tissue from a plant part selected from the group consisting of: fruit, embryo, meristem, cotyledon, pollen, ovule, leaf, anther, root, root tip, pistil, flower, seed, stem. Also parts of any of these are included, such as e.g. only the seed coat (maternal tissue).

Thus, in one aspect of the invention a cell culture or a tissue culture of cells of a plant comprising one, two, three or four copies of a mutant wop1 allele, all as described above, is provided. As mentioned, a cell culture or a tissue culture comprises cells or protoplasts or plant tissue from a plant part of a plant comprising a mutant wop1 allele may comprise or consist of cells or tissues selected from the group consisting of: embryo, meristem, cotyledon, pollen, leaf, anther, root, root tip, pistil, flower, seed, stem; or parts of any of these.

Also provided is a watermelon plant regenerated from such a cell culture or tissue culture, wherein the regenerated plant (or progeny thereof, e.g. obtained after selfing the regenerated plant) comprises the mutant wop1 allele. Therefore, in one aspect the watermelon plant comprising a mutant wop1 allele in one or more copies is a vegetatively propagated watermelon plant.

In a different aspect the cells and tissues of the invention (and optionally also the cell or tissue culture), comprising wop1 in one or more copies, are non-propagating cells or tissues.

Methods According to the Invention

A method for seedless triploid watermelon fruit production is provided, said method comprising:
1. providing a triploid hybrid (F1) watermelon plant or seed comprising at least one, preferably two or preferably three copies of a mutant wop1 allele,
2. planting or seeding said triploid hybrid plants in a field, preferably without planting or seeding diploid pollenizer plants in the same field, and optionally
3. harvesting the seedless watermelon fruits produced on the triploid plants, whereby the fruits are preferably produced without pollination of the female flowers.

In one aspect the triploid hybrid plant of step 1 is preferably not grafted onto a different rootstock.

As mentioned, there is no need anymore to provide diploid pollenizer plants to induce fruit set on of the female flowers of the triploid plants. This means that an entire field can be sown or transplanted with essentially only seeds or transplants of the F1 triploid seeds or plants. Yield of seedless watermelon fruits per hectare is therefore greatly enhanced. Also seeding and planting is made much easier as only one genotype is seeded or planted.

Thus, the method can also be described as a method of producing seedless watermelon fruits, said method comprising growing a triploid plant comprising at least one, preferably two, more preferably three copies of mutant wop1 allele and harvesting the fruits produced by said plants. The fruits develop preferably without pollination of the female flowers, i.e. in the absence of viable pollen. No insects, such as bees, are required anymore for fruit set, i.e. placing bee hives into or near the fields is not necessary.

The harvested triploid fruits may be packaged for fresh markets or for processing. Fruits comprising one, two or three wop1 alleles obtainable by the above method are encompassed herein. Optionally detection of the mutant wop1 allele e.g. by detection of the mutant wop1 allele using DNA, RNA or protein detection as described elsewhere, e.g. by PCR, genotyping or marker analysis of markers linked to (or closely linked to) the wop1 allele, can distinguish such fruits. Thus, in one embodiment, harvested triploid fruits (i.e. wop1/WOP1/WOP1 or wop1/wop1/WOP1 or wop1/wop1/wop1) are provided, such as packaged whole fruits or fruit parts and/or processed fruits or fruit parts.

Also provided is a method for production of a facultative parthenocarpic cultivated watermelon plant comprising the steps of
a) introducing mutations in a population of watermelon plants or providing a mutant population of watermelon plants;
b) selecting a plant producing seedless fruits without pollination of the female flowers and producing a seeded fruit after pollination of the female flowers and/or selecting a plant comprising a mutant allele of the WOP1 gene;
c) optionally verifying if the plant selected under b) comprises a mutant allele of a WOP1 gene; and d) optionally growing the plants obtained under c).

A watermelon plant produced by the above method is encompassed.

The population of watermelon plants under a) is preferably a single genotype of a cultivated watermelon breeding line or variety, which is treated/has been treated with (or subjected to) a mutagenic agent, or progeny of such a population e.g. obtained after selfing individuals of the population to produce M2, M3 or further generation plants. This may for example be a TILLING population.

In step b) plants are screened for the phenotype, i.e. for being facultative parthenocarpic and/or the plants (or plant parts or DNA therefrom) are screened for the presence of a mutant allele of the WOP1 gene, i.e. an allele which either has reduced expression or no expression of the WOP1 protein or an allele encoding a mutant WOP1 protein. Regarding the screening for the phenotype, it is understood that without pollination of the female flowers, seedless fruits should develop; with pollination of the female flowers seeded fruits should develop. This phenotypic screening can be done in several steps. For example first plants can be grown in an insect free environment and male flowers can be removed. Female flowers can be observed visually for flowering and fruit development (in absence of pollen). The developed fruit can be cut in half at maturity to check if these are seedless. Selected plants can e.g. be vegetatively reproduced to confirm the parthenocarpy phenotype and/or to e.g. hand-pollinate flowers to see if fruits are seeded upon pollination (facultative parthenocarpy). Regarding the screening of the plants for the presence of a mutant allele of the WOP1 gene, this can be done by various methods which detect wop1 DNA, RNA or protein, for example by e.g. designing PCR primers which amplify part of the coding region or all of the coding region to amplify the genomic DNA in order to determine if a plant comprises a mutation in the genomic DNA, or other methods.

Step c) can involve various methods to determine whether a mutant wop1 allele is present. For example an allelism test with plants deposited herein can be carried out. Alternatively or in addition marker analysis or sequence analysis of the chromosome 4 region comprising the WOP1 locus can be carried out, or PCR or RT-PCR can be used to amplify the wop1 allele (or a part thereof) or the mRNA (cDNA). Also genetic analysis to determine the recessive inheritance may be carried out.

Also the use of a facultative parthenocarpic watermelon plant for producing seedless watermelon fruits is provided, preferably without pollination of the female flowers of the plant. Further the use of a mutant wop1 allele for generating facultative parthenocarpic watermelon plants and/or seedless watermelon fruits in the absence of pollination of the female flowers is provided. Likewise the use of a mutant wop1 allele of a WOP1 gene according to the invention for producing facultative parthenocarpic watermelon plants is encompassed herein.

In one aspect the plants, plant parts and plant cells according to the invention are not exclusively obtained by means of an essentially biological process as defined by Rule 28 (2) EPC (European Patent Convention).

In one aspect the plants are non-GMO (not genetically modified).

In one aspect the mutant allele of the WOP1 gene comprises a human induced mutation, i.e. a mutation introduced by mutagenesis techniques, such as chemical mutagenesis or UV mutagenesis, or targeted mutagenesis techniques.

In one aspect an isolated mutant WOP1 protein and an isolated wild type WOP1 protein is provided or an isolated nucleic acid molecule encoding a mutant WOP1 protein or a wild type WOP1 protein. Also an antibody able to bind a mutant or wild type WOP1 protein is encompassed herein.

Detection Methods:

In one aspect a screening method for identifying and/or selecting seeds, plants or plant parts or DNA from such seeds, plants or plant parts comprising in their genome a mutant allele of a WOP1 protein-encoding gene is provided.

The method comprises screening at the DNA, RNA (or cDNA) or protein level using known methods, in order to detect the presence of the mutant allele. There are many methods to detect the presence of a mutant allele of a gene.

Thus a method for screening and/or selecting plants or plant material or plant parts, or DNA or RNA or protein derived therefrom, for the presence of a mutant wop1 allele is provided comprising one or more of the following steps:

a) determining if the gene expression of the endogenous WOP1 gene is reduced or abolished;
b) determining if the amount of wild type WOP1 protein is reduced or abolished;
c) determining if a mutant mRNA, cDNA or genomic DNA encoding a mutant WOP1 protein is present;
d) determining if a mutant WOP1 protein is present;
e) determining if plants or progeny thereof have a modified leaf morphology as shown in FIG. 3;
f) determining if plants or progeny thereof are facultative parthenocarpic.

Routine methods can be used, such as RT-PCR, PCR, antibody based assays, sequencing, genotyping assays, phenotyping for steps e and f, etc.

The plants or plant material or plant parts may be watermelon, cucumber or melon plants or plant materials or plant parts, such as leaves, leaf parts, cells, fruits, fruit parts, ovaries, stem, hypocotyl, seed, parts of seeds, seed coat, embryo, etc.

For example if there is a single nucleotide difference (single nucleotide polymorphism, SNP) between the wild type and the mutant allele, a SNP genotyping assay can be used to detect whether a plant or plant part or cell comprises the wild type nucleotide or the mutant nucleotide in its genome. For example the SNP can easily be detected using a KASP-assay (see world wide web at kpbioscience.co.uk) or other SNP genotyping assays. For developing a KASP-assay, for example 70 base pairs upstream and 70 base pairs downstream of the SNP can be selected and two allele-specific forward primers and one allele specific reverse primer can be designed. See e.g. Allen et al. 2011, Plant Biotechnology J. 9, 1086-1099, especially p097-1098 for KASP-assay method.

Equally other genotyping assays can be used. For example, a TaqMan SNP genotyping assay, a High Resolution Melting (HRM) assay, SNP-genotyping arrays (e.g. Fluidigm, Illumina, etc.) or DNA sequencing may equally be used.

Also provided is a method for determining, or detecting or assaying, whether a cell or of a watermelon plant or plant part comprises a mutant allele of a gene name WOP1 encoding a protein of SEQ ID NO: 32, or a protein comprising at least 95%, 96%, 97% or 98% sequence identity to SEQ ID NO: 32, is provided herein. In one aspect the method comprises determining the expression of the allele, and/or determining the coding sequence of the allele and/or determining part of the coding sequence of the allele (e.g. a SNP genotype of the allele), and/or determining the amino acid sequence of the protein produced and/or the amount of protein produced. The same applies to a method for determining, or detecting or assaying, whether a cell or of a cucumber or melon plant or plant part comprises a mutant allele of a gene name WOP1 encoding a protein of SEQ ID NO: 33, or a protein comprising at least 95%, 96%, 97% or 98% sequence identity to SEQ ID NO: 33 (cucumber), or a protein of SEQ ID NO: 34, or a protein comprising at least 95%, 96%, 97% or 98% sequence identity to SEQ ID NO: 34 (melon).

Various method can be used to determine whether a plant or part thereof comprises a mutant wop1 allele of the invention. As mentioned, the mRNA (or cDNA) level of the wild type allele may be determined, or the wild type protein level may be determined, to see if there is a reduced expression or no expression of the wild type allele. Also, the coding sequence or part thereof may be analysed, for example if one already knows which mutant allele may be presence, an assay can be developed to detect the mutation, e.g. a SNP genotyping assay can e.g. distinguish between the presence of the mutant allele in watermelon and the wild type allele, e.g. genotyping for SNP16a.

A method for selection of a plant comprising the steps of:
a) identifying a plant which has a mutation in an allele encoding a WOP1 protein-encoding gene wherein the wild type allele of the gene encodes a WOP1 protein comprising at least 95%, 96%, 97% or 98% sequence identity to any one of the proteins selected from the group of: SEQ ID NO:32 or SEQ ID NO: 33 or SEQ ID NO: 34, and optionally
b) determining whether the plant, or a progeny plant produced by self-fertilization, is facultative parthenocarpic and optionally
c) selecting a plant comprising at least on copy of the mutant allele of step a).

A method for production of a plant comprising the steps of:
a) introducing mutations in a population of plants,
b) selecting a plant producing seedless fruit in the absence of pollination and seeded fruits after pollination and/or comprising a mutant wop1 allele,
c) optionally verifying if the plant selected under b) has a mutation in an allele encoding a WOP1 protein encoding gene and selecting a plant comprising such a mutation, and optionally
d) growing/cultivating the plants obtained under c),
wherein the wild type allele of the gene encodes a WOP1 protein comprising at least 95% sequence identity to any one of the proteins selected from the group of: SEQ ID NO:32 or SEQ ID NO: 33 or SEQ ID NO: 34.

A method for production of a plant comprising the steps of:
a) introduction of a foreign nucleic acid molecule into a plant, wherein the foreign nucleic acid molecule is chosen from the group consisting of
i) DNA molecules, which code at least one antisense RNA, which effects a reduction in the expression of an endogenous gene encoding a WOP1 protein;
ii) DNA molecules, which by means of a co-suppression effect lead to the reduction in the expression of an endogenous gene encoding a WOP1 protein;
iii) DNA molecules, which code at least one ribozyme, which splits specific transcripts of an endogenous gene encoding a WOP1 protein;
iv) DNA molecules, which simultaneously code at least one antisense RNA and at least one sense RNA, wherein the said antisense RNA and the said sense RNA form a double-stranded RNA molecule, which effects a reduction in the expression of an endogenous gene encoding a WOP1 protein (RNAi technology);
v) nucleic acid molecules introduced by means of in vivo mutagenesis, which lead to a mutation or an insertion of a heterologous sequence in an endogenous gene encoding a WOP1 protein, wherein the mutation or insertion effects a reduction in the expression of a gene encoding a WOP1 protein or results in the synthesis of a loss-of-function or reduced function WOP1 protein;
vi) nucleic acid molecules, which code an antibody, wherein the antibody results in a reduction in the activity of an endogenous gene encoding a WOP1 protein due to the bonding of the antibody to an endogenous WOP1 protein,
vii) DNA molecules, which contain transposons, wherein the integration of these transposons leads to a mutation or an insertion in an endogenous gene encoding a WOP1 protein, which effects a reduction in the expression of an endogenous gene encoding a WOP1 protein, or results in the synthesis of an inactive cyclin SDS like protein;
viii) T-DNA molecules, which, due to insertion in an endogenous gene encoding a cyclin SDS like protein, effect a reduction in the expression of an endogenous gene encoding a cyclin SDS like protein, or result in the synthesis of a loss-of-function or reduced function WOP1 protein;
ix) nucleic acid molecules encoding rare-cleaving endonucleases or custom-tailored rare-cleaving endonucleases preferably a meganuclease, a TALENs or a CRISPR/Cas system
b) selecting a plant wherein the plant, or a progeny of the plant produced by self-fertilization, produces seedless fruit in the absence of pollination and seeded fruits after pollination, optionally
c) verifying if the plant selected under b) has a decreased activity of a WOP1 protein compared to wild type plants into whose genome no foreign nucleic acid molecules had been integrated, optionally
d) growing/cultivating the plants obtained under c).

A plant obtained by any of the methods above is encompassed herein.

In one aspect a genetically modified plant and plant part is provided, whereby the plant has reduced expression or no expression of the endogenous WOP1 gene, e.g. through silencing of the endogenous WOP1 gene. Such a plant may be any plant, in one aspect it is a watermelon, melon or cucumber. However, it can also be a maize, soybean, wheat, canola, tomato, cotton, etc.

In another aspect a plant and plant part is provided comprising a mutation in the endogenous WOP1 gene, e.g. an induced mutation generated e.g. by targeted mutagenesis, whereby either the gene expression is reduced or abolished or the expressed gene encodes a reduced function or loss of function WOP1 protein compared to the wild type protein. Such a plant may be any plant, in one aspect it is a watermelon, melon or cucumber as described. However, it can also be a maize, soybean, wheat, canola, tomato, cotton, pepper, etc. As the WOP1 gene in other species may have less sequence identity to the Cucurbitaceae WOP1 gene, it is encompassed herein that in this aspect of the invention the WOP1 gene is a gene encoding a protein comprising at least 60%, 65%, 70%, 75%, 80%, 85%, 90%, 95% sequence identity to SEQ ID NO: 32. Optionally the WOP1 gene is a gene encoding a protein comprising at least 60%, 65%, 70%, 75%, 80%, 85%, 90%, 95% sequence identity to SEQ ID NO: 32 whereby the protein comprises the conserved domain of SEQ ID NO: 35 or a sequence comprising at least 70%, 75%, 80%, 85%, 90%, 95% sequence identity to SEQ ID NO: 35. The skilled person can identify orthologs of the WOP1 gene in such other species, e.g. in pepper or tomato, and thereby make facultative parthenocarpic pepper or tomato plants. All embodiments described herein for watermelon, cucumber and melon apply equally for other crop species, with the difference that the WOP1 gene may thus encode a protein with less than 95% sequence identity to the wild type WOP1 watermelon protein of SEQ ID NO: 32.

Deposit Information

Diploid *Citrullus lanatus* seeds of plants segregating for a mutant wop1 allele have been deposited by Nunhems B.V. under the Budapest Treaty under accession No. NCIMB42533 at NCIMB Ltd., Ferguson Building, Craibstone Estate, Bucksburn Aberdeen AB21 9YA, Scotland, UK on 27 Jan. 2016. The seeds were produced by selfing a plant heterozygous for the mutant wop1 allele (i.e. WOP1/wop1). The deposited seeds consist of 25% WOP1/WOP1 (homozygous wild type WOP1 allele), 50% WOP1/wop1 (heterozygous) and 25% wop1/wop1 (homozygous for the mutant wop1 allele) plants.

Diploid *Citrullus lanatus* seeds of plants segregating for a mutant allele of a cyclin SDS like protein encoding gene (mutant emb1 allele) have been deposited by Nunhems B.V. under the Budapest Treaty under accession No. NCIMB 42532 at NCIMB Ltd., Ferguson Building Craibstone Estate Bucksburn Aberdeen AB21 9YA, Scotland, UK on 27 Jan. 2016. The deposited seeds were obtained from a self-pollinated back-cross of a plant homozygous for the emb1 mutant allele with plants homozygous for the emb1 wild type allele. Therefore 25% of the deposited seeds are homozygous for the emb1 mutant allele and produce seedless fruits, 50% are heterozygous for the mutant allele and 25% are homozygous for the wild type allele, encoding the wild type cyclin SDS like protein.

The Applicant requests that samples of the biological material and any material derived from said samples be only released to a designated Expert in accordance with Rule 32(1) EPC or related legislation of countries or treaties having similar rules and regulation, until the mention of the grant of the patent, or for 20 years from the date of filing if the application is refused, abandoned, withdrawn or deemed to be withdrawn.

Access to the deposits will be available during the pendency of this application to persons determined by the Commissioner of Patent and Trademarks to be entitled thereto upon request.

Subject to 37 C.F.R. § 1.808(b), all restrictions imposed by the depositor on the availability to the public of one or more deposits will be irrevocably removed upon the granting of the patent by affording access to the deposits. The deposits will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Sequence Description

SEQ ID NO 1-24 and SEQ ID NO 29: Sequences of *Citrullus lanatus* comprising Single Nucleotide Polymorphisms on chromosome 4, said SNPs being polymorphic between plants comprising the mutant wop1 allele and plants lacking the mutant wop1 allele of seeds deposited under NCIMB42533.
SEQ ID NO 25: Genomic sequence of a wild type cyclin SDS like protein encoding gene (Emb1 gene) from *Citrullus lanatus*.
SEQ ID NO 26: Amino acid sequence of a SDS like protein from *Citrullus lanatus*. The amino acid sequence is derivable from the coding sequence of SEQ ID NO 25.
SEQ ID NO 27: mRNA sequence of a mutant allele of a cyclin SDS like protein from *Citrullus lanatus*.
SEQ ID NO 28: Amino acid sequence of the mutant allele of a SDS like protein. The amino acid sequence is derivable from SEQ ID NO 27.
SEQ ID NO 30: cDNA and genomic DNA of watermelon encoding the mutant WOP1 protein of SEQ ID NO: 31
SEQ ID NO 31: Amino acid sequence of a mutant WOP1 protein, comprising an S143N mutation, as found in seed deposited under NCIMB42533.
SEQ ID NO 32: Amino acid sequence of a wild type WOP1 protein of watermelon
SEQ ID NO 33: *Cucumis sativus* wild type WOP1 protein
SEQ ID NO 34: *Cucumis melo* wild type WOP1 protein
SEQ ID NO 35: conserved domain "myb-like DNA binding domain SHAQKYF-class" comprised in the WOP1 proteins of SEQ ID NO: 32, SEQ ID NO: 33 and SEQ ID NO: 34
SEQ ID NO 36 to 38: primer pair for WOP1 gene expression analysis and resulting amplified product
SEQ ID NO 39 to 41: primer pair for WOP1 gene expression analysis and resulting amplified product Examples Forward Screening of Mutant Plants A mutant population was established by treating approximately 10.000 watermelon seeds from an inbred diploid line with EMS several hours and subsequently washing the seeds in streaming tap water for 30 minutes. After that the seeds were kept wet until sowing in soil. M1 Plants were grown from the mutagenized seeds, self-pollinated and the seeds (M2 generation) were harvested.

M2 families were grown in insect proof greenhouse and monitored regularly for fruit setting.

Mutant plants producing seedless fruits were isolated. One of these mutant plants was designated wop1.

Propagation of the wop1 mutant plant was performed by grafting cuttings of the wop1 mutant plant to rootstock of a non-mutagenized watermelon plant. The plant was analysed to confirm that the fruit setting was not coming from accidental insect pollination or from hermaphroditic flowers. The plant phenotype was confirmed in two growing seasons. Pollination of the female flowers led to normal, seeded fruits, while in the absence of pollination seedless fruits developed.

The wop1 gene is a single recessive gene.

An homozygous wop1 mutant was back-crossed with the original non-mutagenized watermelon inbred line, (BC1 generation). 25% of the plants grown from the self-pollinated BC1 generation did produce seedless fruits without pollination. Results show that the wop1 mutation is due to a single recessive gene.

Identification of the Gene Causing the Seedless Fruit Phenotype

Pollen from the wop1 mutant was also used for crossing with a watermelon inbred line for establishing an F2 mapping population. F2 individuals were phenotyped for the production of seedless fruits in the absence of pollination of the female flowers. From selected F2 individuals, F2:3 families were phenotyped in the same way.

Using the genotyping and phenotyping data, the mutant wop1 allele was mapped to chromosome 4, between SNP1a and SNP24, especially between SNP1 and SNP24, most likely between SNP3 and SNP23.

Further Identification of the WOP1 Gene

Whole Genome Sequencing was carried out and the mutant wop1 allele was identified to lie in-between SNP16 and SNP17. In this region a SNP was identified in a coding sequence of a gene, SNP16a, which resulted in an amino acid substitution in a small protein comprising a myb-like DNA binding domain SHAQKYF-class. This mutation was unique in the mutant population and was only found in the single mutant plant, the wop1 mutant plant.

Protein WOP1 mutant
(SEQ ID NO: 31)
MREEHSNWFSRWEEELPSPDELMPLSQTLITPDLALAFDIQNPSNSSPPLP

CPSPPLSNPLPGSGNGIAQPNSADFGDSADLGSGAASDEPARTLKRPRLV

WTPQLHKRFVDAVAHLGIKNAVPKTIMQLMSVDGLTRENVANHLQKYRLYL

KRMQGLSSGGGGGGGLVASSDPATDHLFASSPVPPHLLHSARTSSDHFLP

FVPMATLQQHHHHQQQMAAAAAVAVHPQLQPPYHRQVGHFGSPPNGQFEHP

FLARQSQPIHRMGAPVPNSVPNYIEDLESANASGGRKVLTLFPTGDD

Protein WOP1 wildtype
(SEQ ID NO: 32)
MREEHSNWFSRWEEELPSPDELMPLSQTLITPDLALAFDIQNPSNSSPPLP

CPSPPLSNPLPGSGNGIAQPNSADFGDSADLGSGAASDEPARTLKRPRLV

WTPQLHKRFVDAVAHLGIKNAVPKTIMQLMSVDGLTRENVASHLQKYRLYL

KRMQGLSSGGGGGGGLVASSDPATDHLFASSPVPPHLLHSARTSSDHFLP

FVPMATLQQHHHHQQQMAAAAAVAVHPQLQPPYHRQVGHFGSPPNGQFEHP

FLARQSQPIHRMGAPVPNSVPNYIEDLESANASGGRKVLTLFPTGDD

The protein contained a conserved myb-like DNA binding domain SHAQKYF-class (highlighted in boxes above) and the amino acid substation was in the SHAQKYF motif of the domain. This motif is a conserved motif having amino acids SH[A/L]QKY[R/F]L and is part of an alpha-helix.

SIFT analysis (Pauline and Henikoff 2003, NAR 31, 3812-3814) confirmed that the mutant WOP protein is predicted to have a reduced function or loss of function.

The facultative parthenocarpic phenotype co-segregated with the mutant wop1 allele and in plants homozygous for the mutation (wop1/wop1) leaf margin and leaf blade was found to be modified, see FIG. 3. This phenotype was also seen in most plants heterozygous for the mutant allele (WOP1/wop1) and appears to be caused by the mutant wop1 allele. The modified leaf morphology can therefore be used as a phenotypic trait in distinguishing plants homozygous or heterozygous for the mutant wop1 allele from plants lacking the mutant wop1 allele and only comprising the wild type allele (WOP1/WOP1). Out of 10 backcross inbred lines, 8 comprised the modified leaf morphology and comprised the wop1 allele in homozygous or heterozygous form. Two backcross inbred lines heterozygous for the mutant wop1 allele could not be clearly distinguished from the wild type plant, indicating that the genetic background may influence the expression of the morphology when the allele is in heterozygous form.

Orthologs of the WOP1 gene were identified using protein BLAST analysis.

Protein WOP1 cucumber
(SEQ ID NO: 33)
MREEHSNWFSRWEDELPSPDELMPLSQTLITPDLALAFDIQNPSNSSPPLP

CPSPPLSNPLPGSGNGIVPPNSADFGDSADLGSGAASDEPARTLKRPRLVW

TPQLHKRFVDAVAHLGIKNAVPKTIMQLMSVDGLTRENVASHLQKYRLYLK

RMQGLSGGGGGGGAALVGSSDPATDHLFASSPVPPHLLHSARTSSDHFLPY

VPMATLQQHHHHQQQMAAAAAVAGHTQLQPPYHRQVGHFGSPPNGQFEHPF

LARQSQPIHRMGTPVHNSVPNYIEDLESANATGGRKVLTLFPTGDD

Protein WOP1 melon
(SEQ ID NO: 34)
MREEHSNWFSRWEEELPSPDELMPLSQTLITPDLALAFDIQNPSNSSPPLP

CPSPPLSNPLPGSGNGIVPPNSADFGDSADLGSGAASDEPARTLKRPRLVW

TPQLHKRFVDAVAHLGIKNAVPKTIMQLMSVDGLTRENVASHLQKYRLYLK

RMQGLSGGGAGGGAALVGSSDPATDHLFASSPVPPHLLHSARTSSDHFLPF

VPMATLQQHHHHQQQMAAAAAVAGHTQLQPPYHRQVGHFGSPPNGQFEHPF

LARQSQPIHRMGTSVHNSVPNYIEDLESANATGGRKVLTLFPTGDD

These two proteins also contain the myb-like DNA binding domain SHAQKYF-class (highlighted in boxes above). The proteins each have 95.3% sequence identity to the wild type watermelon WOP1 protein (SEQ ID NO: 32) and comprise 98.7% sequence identity to each other using the program Needle of website ebi.ac.uk with default parameters).

Expression Analysis of the WOP1 Gene in Watermelon:

RT-PCR analysis was carried out to determine mRNA expression in the wop1 mutant plant and in the WOP1 wild type plant. Tissue samples were taken from young leaf tissue, ovary tissue of open flowers, ovary tissue at 3-4 and 5-6 days after pollination/fruit development of both wild type and mutant plants.

Two primer combination (A6254-6255 and A6256-6257) were used for measuring the expression of WOP1. The primer combinations amplify different parts of the mRNA/cDNA. Two household genes (C1PP2A and C1YLS8) were added as control.

A6254
(SEQ ID NO: 36)
CCTACACGACGCTCTTCCAAGAGGAGCTTCCATCTCCAG

A6255
(SEQ ID NO: 37)
CTGCTGAACCGCTCTTCCAGCCCAAATCGGCAGAATC

Amplified fragment (nucleotides 38 to 250 of SEQ ID NO: 30):

(SEQ ID NO: 38)
AAGAGGAGCTTCCATCTCCAGATGAATTGATGCCTCTTTCTCAAACCCTA

ATAACCCCCGATCTAGCTTTGGCCTTTGATATTCAGAATCCCAGCAATAG

CAGTCCGCCGTTGCCTTGTCCATCTCCGCCGCTTTCGAATCCTCTGCCTG

GCTCTGGCAACGGAATTGCGCAGCCCAACTCGGCGGATTTCGGCGATTCT

GCCGATTTGGGCT

A6256

(SEQ ID NO: 39)

CCTACACGACGCTCTTCCGTGGCTTGGTTGCTTCCTC

A6265

(SEQ ID NO: 40)

CTGCTGAACCGCTCTTCCGATGATAAGGCGGCTGGAG

Amplified fragment (nucleotides 500 to 712 of SEQ ID NO: 30):

(SEQ ID NO: 41)

GTGGCTTGGTTGCTTCCTCCGATCCCGCCACTGACCATTTGTTTGCCAGC

TCCCCAGTTCCACCCCATTTGCTTCACTCTGCTCGCACCAGTTCAGACCA

TTTCTTGCCCTTTGTTCCCATGGCCACTCTGCAGCAGCACCACCATCACC

AGCAGCAGATGGCCGCTGCTGCTGCTGTCGCCGTCCATCCGCAGCTCCAG

CCGCCTTATCATC

The expression was normalized to one of the household genes. The wild type young leaf sample was put at 100%. The expression of the wop1 mutant allele was essentially similar to the expression of the WOP1 wild type allele in the young leaf and in the developing ovary tissues. For both primer pairs similar results were obtained. This shows that the wop1 mutation in the coding sequence has no effect on WOP1 gene expression.

The invention claimed is:

1. A watermelon plant or plant part comprising at least one copy of a mutant allele comprising a nucleotide sequence encoding a protein having the amino acid sequence of SEQ ID NO: 32 wherein amino acid 143 of SEQ ID NO: 32 is replaced by Asparagine, said mutant allele conferring facultative parthenocarpy when the mutant allele is in homozygous form.

2. The watermelon plant or plant part according to claim 1, wherein said plant or plant part is diploid and is homozygous for the mutant allele.

3. The watermelon plant or plant part according to claim 1, wherein the plant is diploid, triploid or tetraploid.

4. The watermelon plant or plant part according to claim 3, wherein the diploid plant or plant part comprises two copies, the triploid plant or plant part comprises one, two or three copies and the tetraploid plant or plant part comprises four copies of the mutant allele.

5. A seed from which a plant or plant part according to claim 1 can be grown.

6. A fruit produced by a plant according to claim 1, wherein the fruit comprises the mutant allele, and optionally wherein the fruit is seedless and is produced in the absence of pollination.

7. The watermelon plant or plant part according to claim 1, wherein said plant or plant part further comprises a gene conferring male sterility or a gene conferring stenospermocarpy.

8. The watermelon plant part according to claim 1, wherein the plant part is a cell, a flower, a leaf, a stem, a cutting, an ovule, pollen, a root, a rootstock, a scion, a fruit, a protoplast, an embryo, or an anther, wherein the plant part comprises the mutant allele.

9. A vegetatively propagated plant propagated from a plant part according to claim 8, wherein the vegetatively propagated plant comprises the mutant allele.

10. A method of producing seedless watermelon fruits, comprising growing a triploid watermelon plant comprising one, two or three copies of the mutant allele according to claim 1, and harvesting the fruits produced by said plants.

11. The method according to claim 10, whereby the fruits develop without pollination of the female flowers.

12. The watermelon plant or plant part of claim 1, wherein the watermelon plant is a triploid watermelon plant.

13. A seed from which a diploid watermelon plant comprising two copies of a mutant allele comprising a nucleotide sequence encoding a protein having the amino acid sequence of SEQ ID NO: 32, wherein amino acid 143 of SEQ ID NO: 32 is replaced by Asparagine, can be grown.

14. A seed from which a triploid watermelon plant comprising at least one copy of a mutant allele comprising a nucleotide sequence encoding a protein having the amino acid sequence of SEQ ID NO: 32, wherein amino acid 143 of SEQ ID NO: 32 is replaced by Asparagine, can be grown.

15. A method of growing a plant comprising growing the seed of claim 13 in a field.

16. A method of growing a plant comprising growing the seed of claim 14 in a field.

17. A method for producing triploid hybrid watermelon seeds, comprising
(a) providing a diploid watermelon plant comprising two copies of a mutant allele comprising a nucleotide sequence encoding a protein having the amino acid sequence of SEQ ID NO: 32, wherein amino acid 143 of SEQ ID NO: 32 is replaced by Asparagine and a tetraploid plant lacking the mutant allele,
(b) allowing pollination of the pistillate flowers of the tetraploid plant with pollen of the diploid plant, and
(c) harvesting seeds produced in the fruits of the tetraploid plant, and optionally
(d) drying the harvested seeds.

* * * * *

SEQUENCE LISTING

<160> NUMBER OF SEQ ID NOS: 41

<210> SEQ ID NO 1
<211> LENGTH: 151
<212> TYPE: DNA
<213> ORGANISM: Citrullus lanatus

<400> SEQUENCE: 1
tagctttcaa ttagaatttc ttatgaaaat tgtttacgta tcaattatca ttgtcatttt    60
gctagtttta cctttaaagt ttaattgata caattgtaaa tctcaccatg tttttcaaac   120
gaaatctaaa agagtataaa ttgatacaat t                                  151

<210> SEQ ID NO 2
<211> LENGTH: 151
<212> TYPE: DNA
<213> ORGANISM: Citrullus lanatus

<400> SEQUENCE: 2
agaagarggc gaagttgagg aaagagctca gagccctaag aagaggagca gaggaaattg    60
ctaaggacgc attgttcaac aaaaaggtgt gcagggtagt gcaacctgaa gaagaaatac   120
aaacgcatag acttcctgat cctcaagtag a                                  151

<210> SEQ ID NO 3
<211> LENGTH: 151
<212> TYPE: DNA
<213> ORGANISM: Citrullus lanatus

<400> SEQUENCE: 3
taaaatggtt gttcaaggaa ggttattgaa agatgataat ttgattttca agtcaaacga    60
taataggaga cgcatcaaag aatcaaaagg gattttgag tgaaaattat tatttaaaat   120
gtttcctaat tggttataag gatgtttttc c                                  151

<210> SEQ ID NO 4
<211> LENGTH: 151
<212> TYPE: DNA
<213> ORGANISM: Citrullus lanatus

<400> SEQUENCE: 4
ccgagagcga gattctgagc gagagcgaga gagcgagagt ctgagcgaga gagtgagatt    60
ctggcgaggg acttcccgga aagtagaatc cgtcaaggcg agcggcgact gagagagaga   120

```
caacgggaaa caaaggtaaa gagagagtgt g                                    151

<210> SEQ ID NO 5
<211> LENGTH: 151
<212> TYPE: DNA
<213> ORGANISM: Citrullus lanatus

<400> SEQUENCE: 5
aagcagcagg cattttagtt aattaaacga aaacttacgg gaattaggat tcattaactt     60
aaattaacta aagttaattt taaaaaatag tggaattggt ttaacttaag tttaattaac    120
taattaaaaa tataaaactt aatcagcttt g                                   151

<210> SEQ ID NO 6
<211> LENGTH: 151
<212> TYPE: DNA
<213> ORGANISM: Citrullus lanatus

<400> SEQUENCE: 6
aaaatttacc tttagagttt ggactcgctg ccactggaaa tcgactcact cactagcact     60
gatctgagac ttttacaaaa atggagaaag acttttacat gagttggtaa cacatacggt    120
gaccaactcc aacaaacaat catcgcctta c                                   151

<210> SEQ ID NO 7
<211> LENGTH: 151
<212> TYPE: DNA
<213> ORGANISM: Citrullus lanatus

<400> SEQUENCE: 7 caccctcttag atgcagggtt gatagttttt ggactcgtag tgcactagtt agacgcctaa    60
ttttcttcat aaaggttctc aacttttctt aatttgagtt ctaaagtgat tttcagtgag   120
taaagaagtg attccccgag tcttatttat a                                   151

<210> SEQ ID NO 8
<211> LENGTH: 151
<212> TYPE: DNA
<213> ORGANISM: Citrullus lanatus

<400> SEQUENCE: 8
aaatgaagtt aaaccgaaaa aagtgtgctt tcggagtagc ttcaggcaag tttctaggct     60
tcatggtcaa tcatagagga attaaagcaa atctagacaa gatacgagct gtcctggaga   120
tggagtctcc taagacacta aagcaacttc a                                   151

<210> SEQ ID NO 9
<211> LENGTH: 151
<212> TYPE: DNA
<213> ORGANISM: Citrullus lanatus

<400> SEQUENCE: 9
aagggtgatt gtacaagaga aggatttgta gctaagaatg gacataagga aagagagagg     60
acgcatgata gtatgcgatt aaggcagacg catggtatta tatggtaagc tgaaacgtat   120
agtagtatgc gtttaagact taaacaccta g                                   151

<210> SEQ ID NO 10
<211> LENGTH: 151
<212> TYPE: DNA
<213> ORGANISM: Citrullus lanatus

<400> SEQUENCE: 10
```

```
atgtttgatt gaaaccaaaa accagaagaa ttcgaagctc aacccaatcc caagaaagag      60
gagttggaag tggtgaaaac gggagaagaa gaagaagaac aacaacaaca acaagatgct     120
gaatcttact gttcgaagtt tactgggtag a                                    151
```

<210> SEQ ID NO 11
<211> LENGTH: 151
<212> TYPE: DNA
<213> ORGANISM: Citrullus lanatus

<400> SEQUENCE: 11

```
gtttggtgaa tatctgaaac atacaaaatg gatttaattg tgtagataaa ttcattgttt      60
agaaactttc aaattgaatt gaaatttcaa attaaaatga tgtttcatgt acaaatttaa     120
catgtatgaa agttaaattt gtagtttctt c                                    151
```

<210> SEQ ID NO 12
<211> LENGTH: 151
<212> TYPE: DNA
<213> ORGANISM: Citrullus lanatus
<220> FEATURE:
<221> NAME/KEY: misc_feature
<222> LOCATION: (146)..(146)
<223> OTHER INFORMATION: n is a, c, g, or t

<400> SEQUENCE: 12

```
ttttgttatc tactttctaa aagtgttcta aaaaaccaat caatggtttg gaaactagtt      60
ttcaaaaatt tattttttgtt tttaaaaatt tgacgaaaaa ttcaaaagtt tctttaagaa    120
aggttgaagc tatagtaaag aatttntgag g                                    151
```

<210> SEQ ID NO 13
<211> LENGTH: 151
<212> TYPE: DNA
<213> ORGANISM: Citrullus lanatus

<400> SEQUENCE: 13

```
caaaagttgc atgatatagt aatagccaaa cacataatgt aatgttaagt atccgaaggt      60
cgtagtaatt ctcttgactt acattaacag caacaatgga aggaaaaaaa aacccaaata    120
agtacccaaa aattaaagaa tactttctat g                                    151
```

<210> SEQ ID NO 14
<211> LENGTH: 151
<212> TYPE: DNA
<213> ORGANISM: Citrullus lanatus

<400> SEQUENCE: 14

```
ttgtagaaat taaacccaca aatgatagaa atcgaactct cacatttgta cgattattac      60
aatttgtaca attatattag tctgagagtt caattttaac atttgtataa gtttgaagtc    120 tcaatttta aaattaaaag tttaagggga t                                     151
```

<210> SEQ ID NO 15
<211> LENGTH: 151
<212> TYPE: DNA
<213> ORGANISM: Citrullus lanatus

<400> SEQUENCE: 15

```
tggagtcacc cttcgtcggc catattctcg catttccccg tcactcagtt gcagcgctcc      60
agccttcacg gtgcggcctt aatcgcagtt cacagcattg tggcatcgtc atagttgtcg    120
```
cgccgcagca tcttggtcgt cgcgccccag c    151

<210> SEQ ID NO 16
<211> LENGTH: 151
<212> TYPE: DNA
<213> ORGANISM: Citrullus lanatus

<400> SEQUENCE: 16 actttctaa aaaacaacca ttacttatgc aatatgattg attcctaatt tcttgaaacc    60
aagttaataa gcataacatt aagattagtc atgatcaact ttttctaata acctagctat    120
ttaattaata gagattcaat gctatagatc c    151

<210> SEQ ID NO 17
<211> LENGTH: 151
<212> TYPE: DNA
<213> ORGANISM: Citrullus lanatus

<400> SEQUENCE: 17
atgtaattag agtaagtatc catatgaaat atgatccaat cgatatttga ataattaac    60 aaacttgcta ctaaagaaaa ctttagcttt taaacctaca caaatttaat atatgaaata    120 cactttgat ctggttgaat tccaattcta a    151

<210> SEQ ID NO 18
<211> LENGTH: 151
<212> TYPE: DNA
<213> ORGANISM: Citrullus lanatus

<400> SEQUENCE: 18
tttactcaaa ttttaaaaaa cttgttttgt ttttagaacg gtgaaaatta ccataattta    60
aaaattggaa ggaaccaata taaattttta aggaaaaaaa aacaaaaaaa ttaaaacaaa    120
atcgttgcaa aaagaccttt aattatattg a    151

<210> SEQ ID NO 19
<211> LENGTH: 151
<212> TYPE: DNA
<213> ORGANISM: Citrullus lanatus

<400> SEQUENCE: 19
tctaccaatc ttactctatt aattctccca atttttatta gaaaaattct aagaaaattc    60
ttattcccat aagcggttcc cacaaaccag atctttgcgc gagtcatagc gaggaagatc    120
tcttggaaaa gaaagactac aaggagaaga c    151

<210> SEQ ID NO 20
<211> LENGTH: 151
<212> TYPE: DNA
<213> ORGANISM: Citrullus lanatus

<400> SEQUENCE: 20
aacattttac tataaatttt ggaaacacat tcacatatta tatttcttta cataaaaatt    60
attgttgtta tttaatcaat ttcaataaaa attaactttg agagactaaa tttaagattt    120
attaaaaata cataaattaa aattggacaa t    151

<210> SEQ ID NO 21
<211> LENGTH: 151
<212> TYPE: DNA
<213> ORGANISM: Citrullus lanatus

<400> SEQUENCE: 21
aacatcctaa aactatgagt ttagccacgg atagacatca aatacataca ttcatatgag    60
ttctcaagca taaaagtaaa agagaaagag aaacttagga agaaagactc tcgaattgct   120
tccccgcgtt gaattccttc gatctccact t                                  151

<210> SEQ ID NO 22
<211> LENGTH: 151
<212> TYPE: DNA
<213> ORGANISM: Citrullus lanatus

<400> SEQUENCE: 22
cttttcaggt ggctactcct aaacatttct ttacaggtgg gtgcttctag catgacagtt    60
ttacgtagta tttggcagag ttactggctc gataagcatg gggatgccat ggagagcgtt   120
gttgatcagc ttgcacgaag tctatcagag a                                  151

<210> SEQ ID NO 23
<211> LENGTH: 151
<212> TYPE: DNA
<213> ORGANISM: Citrullus lanatus

<400> SEQUENCE: 23
atatgtcatt aataaattgc taactagact aaaaatttag atgtctaaac acatatgttg    60
cttaggtgtg ccaaataatc ggattgatat atatggaaat ttacgatcat agaataatta   120
ttttagggcc atttttttaa ttgacgttta a                                  151

<210> SEQ ID NO 24
<211> LENGTH: 151
<212> TYPE: DNA
<213> ORGANISM: Citrullus lanatus

<400> SEQUENCE: 24
tcagatgagt gacgttcaat tgtctatttt tattgtacaa tcaatgatca caacaaagct    60
atttatattt tcaatcattc tattttgtt gtatagtaat tttgttatat agtaatttcg    120
ttatcctaaa ctattttcat tcttctaagt a                                  151

<210> SEQ ID NO 25
<211> LENGTH: 5135
<212> TYPE: DNA
<213> ORGANISM: Citrullus lanatus
<220> FEATURE:
<221> NAME/KEY: exon
<222> LOCATION: (1018)..(2088)
<220> FEATURE:
<221> NAME/KEY: CDS
<222> LOCATION: (1018)..(2088)
<220> FEATURE:
<221> NAME/KEY: Intron
<222> LOCATION: (2089)..(2185)
<220> FEATURE:
<221> NAME/KEY: exon
<222> LOCATION: (2186)..(2353)
<220> FEATURE:
<221> NAME/KEY: CDS
<222> LOCATION: (2186)..(2353)
<220> FEATURE:
<221> NAME/KEY: Intron
<222> LOCATION: (2354)..(3098)
<220> FEATURE:
<221> NAME/KEY: exon
<222> LOCATION: (3099)..(3265)
<220> FEATURE:
<221> NAME/KEY: CDS
<222> LOCATION: (3099)..(3265)
<220> FEATURE:

```
<221> NAME/KEY: Intron
<222> LOCATION: (3266)..(4324)
<220> FEATURE:
<221> NAME/KEY: exon
<222> LOCATION: (4325)..(4607)
<220> FEATURE:
<221> NAME/KEY: CDS
<222> LOCATION: (4325)..(4604)

<400> SEQUENCE: 25
```

| | |
|---|---:|
| aaacattcat acttttgaag aaaattagta tattatttat ttatattata tttacagatt | 60 |
| atttattgat tatttttaa atatttattg aattttttat aatataataa aaatgtcgac | 120 |
| atgtcaacac aaaattaatt tcatatattg aattagaagt agggaataag agtatgtttg | 180 |
| gaataaattt tcaagtattt aattttaaaa ataagtcact tcaaaagaaa tataagtgtt | 240 |
| tggcaaccac tcaaactgta ttttaaaagc cattagtgtc tttattataa atacttttct | 300 |
| tatcaaaagt gtttaaatga aaataaaagt ttgaagacat ttcttttcta ggttaatcga | 360 |
| atggcttcta aatttaagat ttatcaaatg tatatggtat gtttggttca aaagagtttt | 420 |
| tgagcttata attaaagaac atcaatctca tgacttatca attttttgta atgtgtattt | 480 |
| aaaaaaaaaa agaaataaaa aagaaaaaga aagaaaaac attttgtaat aggaccctac | 540 |
| aattaaacaa tttaggacat gtctagggag tgattctaaa atagttaaat ccacttttgt | 600 |
| tattattgaa atcacttta aatatttcaa atcttccaaa cacaaaattt attatataaa | 660 |
| aattatactt aaaaatgtaa aattaaatac taaattaatt tggagtgatt taatatatgt | 720 |
| tttggggata tatccatttc aaaatcactc caaatatgaa tttcataaaa ttaaagttga | 780 |
| atatttgaaa gtagaagact aaaatggaaa agaatataga ggtgagggggc caaaatgata | 840 |
| tttaactaaa taattattat tatttattag attagcacga gaggaggtga cagtgaggga | 900 |
| ccctctccaa aaaaaaaaa aactcacttc caattcacaa ttctcttttg cttcctaact | 960 |
| tccataactg ctctgctttc catcacgaaa ctcatcttca tcttcttcat tcgaaca | 1017 |

| | | | | | | | | | | | | | | | | |
|---|---|---|---|---|---|---|---|---|---|---|---|---|---|---|---|---:|
| atg | aag | tcc | aag | aag | cca | agg | gca | aat | ccc | aaa | ccc | gaa | tcc | tac | tct | 1065 |
| Met | Lys | Ser | Lys | Lys | Pro | Arg | Ala | Asn | Pro | Lys | Pro | Glu | Ser | Tyr | Ser | |
| 1 | | | | 5 | | | | | 10 | | | | | 15 | | |
| ccg | ccg | aag | aag | aag | ctc | cgt | tct | cag | ctt | cca | cgg | cgc | aga | cgc | tct | 1113 |
| Pro | Pro | Lys | Lys | Lys | Leu | Arg | Ser | Gln | Leu | Pro | Arg | Arg | Arg | Arg | Ser | |
| | | 20 | | | | | 25 | | | | | 30 | | | | |
| cgg | att | tct | cct | ttt | ttc | tgc | tcc | ttg | gac | tcc | gat | tcc | cct | gct | cct | 1161 |
| Arg | Ile | Ser | Pro | Phe | Phe | Cys | Ser | Leu | Asp | Ser | Asp | Ser | Pro | Ala | Pro | |
| | | | 35 | | | | | 40 | | | | | 45 | | | |
| tct | acc | acc | att | gct | ttt | gct | tct | tct | tcc | ttt | gct | gcc | gcc | gaa | tcc | 1209 |
| Ser | Thr | Thr | Ile | Ala | Phe | Ala | Ser | Ser | Ser | Phe | Ala | Ala | Ala | Glu | Ser | |
| | 50 | | | | | 55 | | | | | 60 | | | | | |
| agc | tcc | act | tcc | ttc | cac | gca | ggc | gga | cct | gag | gtt | tct | agc | cag | ctc | 1257 |
| Ser | Ser | Thr | Ser | Phe | His | Ala | Gly | Gly | Pro | Glu | Val | Ser | Ser | Gln | Leu | |
| 65 | | | | 70 | | | | | 75 | | | | | 80 | | |
| aac | gcg | tgt | ttt | gga | ttc | cag | agg | ccg | aat | ttg | cgg | aag | aga | cga | ttt | 1305 |
| Asn | Ala | Cys | Phe | Gly | Phe | Gln | Arg | Pro | Asn | Leu | Arg | Lys | Arg | Arg | Phe | |
| | | | 85 | | | | | 90 | | | | | 95 | | | |
| ggt | tcg | ggt | ggt | gtt | aat | ttg | gat | gaa | gtt | tcg | aag | aag | gag | gtt | gga | 1353 |
| Gly | Ser | Gly | Gly | Val | Asn | Leu | Asp | Glu | Val | Ser | Lys | Lys | Glu | Val | Gly | |
| | | | 100 | | | | | 105 | | | | | 110 | | | |
| gta | ggg | agt | aat | gtg | gaa | gtg | tct | gaa | tcg | tct | tgc | gtt | gaa | tca | aat | 1401 |
| Val | Gly | Ser | Asn | Val | Glu | Val | Ser | Glu | Ser | Ser | Cys | Val | Glu | Ser | Asn | |
| | | 115 | | | | | 120 | | | | | 125 | | | | |
| tct | gga | gtt | gat | ttt | ggt | gtt | ctc | gga | cca | agc | act | agc | tcc | agg | ttg | 1449 |
| Ser | Gly | Val | Asp | Phe | Gly | Val | Leu | Gly | Pro | Ser | Thr | Ser | Ser | Arg | Leu | |

```
                130                 135                 140
aag att aga agt gat ttt agg aga act att gac gaa aat gaa gat cca       1497
Lys Ile Arg Ser Asp Phe Arg Arg Thr Ile Asp Glu Asn Glu Asp Pro
145                 150                 155                 160 atc gat caa gcg gat aat gga gtt gtg aag ttt caa ttg acg gat gct       1545
Ile Asp Gln Ala Asp Asn Gly Val Val Lys Phe Gln Leu Thr Asp Ala
                    165                 170                 175 gat gtc tcg tcg aag ctt tgt gaa aag gga gct gtg cca ctc act cct       1593
Asp Val Ser Ser Lys Leu Cys Glu Lys Gly Ala Val Pro Leu Thr Pro
                180                 185                 190 tgt gga gag tct tgc gct gag tct atc ttc cag agc gtt tgt tcg ttc       1641
Cys Gly Glu Ser Cys Ala Glu Ser Ile Phe Gln Ser Val Cys Ser Phe
            195                 200                 205 gaa gag aaa gga tta gac gtt gaa gaa aac aga cta tgg gaa ttt cag       1689
Glu Glu Lys Gly Leu Asp Val Glu Glu Asn Arg Leu Trp Glu Phe Gln
210                 215                 220 tta cca gaa cta ccg aga aat gag atc aat gaa act ttc act gtt tcg       1737
Leu Pro Glu Leu Pro Arg Asn Glu Ile Asn Glu Thr Phe Thr Val Ser
225                 230                 235                 240 aag tcg gat tcg acg ata gaa cag tgg cct aat agc ttg aag ttt gaa       1785
Lys Ser Asp Ser Thr Ile Glu Gln Trp Pro Asn Ser Leu Lys Phe Glu
                245                 250                 255 tcg gat ctt gct tgc acg gag caa ttc tct tat gag aat gtt tcg gaa       1833
Ser Asp Leu Ala Cys Thr Glu Gln Phe Ser Tyr Glu Asn Val Ser Glu
            260                 265                 270 tac tct agc cag gcg ttg tcc gag ctt caa tca aca att cta ttg gag       1881
Tyr Ser Ser Gln Ala Leu Ser Glu Leu Gln Ser Thr Ile Leu Leu Glu
        275                 280                 285 acg tct gat act gac tgc tca gat tac act cct tca att ttt ttg gaa       1929
Thr Ser Asp Thr Asp Cys Ser Asp Tyr Thr Pro Ser Ile Phe Leu Glu
    290                 295                 300 tcc gga agc gaa ttt tca gag aaa tcg aac gac gac gca gct cct tcg       1977
Ser Gly Ser Glu Phe Ser Glu Lys Ser Asn Asp Asp Ala Ala Pro Ser
305                 310                 315                 320 tca aca ttt agc atg ttg ctg cag tac aga cgc gac ttt cta aac tta       2025
Ser Thr Phe Ser Met Leu Leu Gln Tyr Arg Arg Asp Phe Leu Asn Leu
                325                 330                 335 aat gcc tct cca gac atc aga act agc tcg tct att gaa gaa gag aaa       2073
Asn Ala Ser Pro Asp Ile Arg Thr Ser Ser Ser Ile Glu Glu Glu Lys
            340                 345                 350 gta gat caa tct acg gtaattcgct atcttcatgc ttccttgacg tttcatttgc       2128
Val Asp Gln Ser Thr
        355 aacaaacctg aagctaatca aacaactata tatatatatt atttgatttt aaattag       2185 att ttg aga ttt gaa gaa ttg gac gat gaa gaa gcc tat cta atg ttc       2233
Ile Leu Arg Phe Glu Glu Leu Asp Asp Glu Glu Ala Tyr Leu Met Phe
        360                 365                 370 aga agt aga gaa aga cgc caa ttg att att cgc gac tac gta gag gag       2281
Arg Ser Arg Glu Arg Arg Gln Leu Ile Ile Arg Asp Tyr Val Glu Glu
    375                 380                 385 tat cgg tcc aca acg gat tat ggc gat ctc att ctc cag caa cgg tca       2329
Tyr Arg Ser Thr Thr Asp Tyr Gly Asp Leu Ile Leu Gln Gln Arg Ser
390                 395                 400                 405 aat gtg gtc caa tgg ata gtt gaa gtaagtcctt gataccaaac caccgtgttt     2383
Asn Val Val Gln Trp Ile Val Glu
                410 ctctcaataa ttcctgaatt agcatgagat attttgctcc ggttttccat tttcatcgtt     2443 aatagcattg gtattctgag acattggaac tgtttagtgt atcgaggtag tttgaagcac     2503
```

```
tgactctcat atttcaattt gcactgaatc gctaattagt tcttaacatc tcataaaatg    2563
agttcccttg ccttatttgc tatggaactt tatccgacag cgtacttttc tgatttggct    2623
atcccaacaa tgtgatttac taatgaaaat tacaaagtca ttaccatgat catactttcc    2683
actacttaaa agccagcagt ttatgatctt gcacctgtta catctagttg ttataagctc    2743
attctaacga atgaggcctg ccaccagcac aacgcatctg gcatcttgaa tcaactaagt    2803
ttaactgatt tttcatttct tttcttactt ctgcttgaat atattttctg tttgtttttc    2863
atcttaataa tagaatacag attcataacc gcgagatttg tgcttattac tgtggatgtt    2923
gacattttct taggaatact ccaatgtagt tgcattttca tcatctgttg acgtttctag    2983
ttcaaggaat acattcttta tactattttt attccttttc tgcgttaata cttgtcacca    3043
accaattggg tcaaatttt tacattatgt tgctttgttt gttgaatga tgcag cga       3101
                                                             Arg
tcg aga gat tcc aaa ctt cat cag gag acg aca ttt tta gga gtt acc      3149
Ser Arg Asp Ser Lys Leu His Gln Glu Thr Thr Phe Leu Gly Val Thr
415                 420                 425                 430 ctc ctg gac cag att ctg agc aga gga ttc ttc aaa gct gga aga cac      3197
Leu Leu Asp Gln Ile Leu Ser Arg Gly Phe Phe Lys Ala Gly Arg His
                435                 440                 445 ctt caa att ctg ggc ata gca tgt cta act ttg gcg act aga att gaa      3245
Leu Gln Ile Leu Gly Ile Ala Cys Leu Thr Leu Ala Thr Arg Ile Glu
            450                 455                 460 gaa aat cag tca tac agc tg  gtgactttt ttctatcttt tgtctatttg          3295
Glu Asn Gln Ser Tyr Ser Trp
                465 tgtgcatctc agttttaact atataacaag tgttgttctt atctactgta acttcaactt    3355 aacttcgtta gtatgatgaa tattgcttga aaacaaactg tatgccagtt ggtcttcttg    3415 tttcgatcca agggagtgaa attgggtaag ttaggatcga atgctaagta gtactagaaa    3475 taataatcag aaagaattgt attaaagtaa ttgaatctaa tagtcttgaa tattttttct    3535 aaagttcaaa gtgtcgagcc tgaaagcttt gcgtttacat ggaccaaagt aatgttgtga    3595 atatatcgta ggtcctctta tagcaattat gtaacaaata tagccatac attagtgtcg     3655 atacacacca cccgtacggt actgtagtcg aatattgcca taacactatc tttcagttct    3715 tatgttaaca attcatgtgc acagaagaga cccgagaccc accaagaaaa cattatcttt    3775 gacttgtata tagaactcta agtcgagtca aatgtaaaac aattcttttt cttctcttct    3835 ctttctcaaa cttcctttg tagccttcat ttatctttga cttgcaattt acatgcaaaa     3895 tgttaaataa ttgtgatttg tttaattaaa tagagccttg tgaattgaga aggtatccaa    3955 gctagctggt gggtctcgag cttggtggat atatttataa agctatgata ggactgattt    4015 gttttatttt tgggcatttc agggtgcagc aaaggaatat ccgtgtagag agcaacacgt    4075 acagaagatc tgaagttgtt ggcatggaat ggcttgttga agaagtctta aagttccatt    4135 gtttcttgcc aactgtttac aacttcttat ggtacatctt cctttgacta acttgaccat    4195 tggtgggaag ggaaaaagtt ttcccttcg tgcatccatt ttcaataaac tccttccgcc     4255 cattaacaat ttgaatctac tgcgaataac atgcttatt taattttctt tttttgaaaa    4315 ttatcttag g ttc tac ctg aaa gct gct gga gct gac tcg aat ttg gag     4364
            Phe Tyr Leu Lys Ala Ala Gly Ala Asp Ser Asn Leu Glu
                470                 475                 480 aat cga gct aag aac ttt gcg gag ctg gtt ctt tca gac aaa gtc caa      4412
Asn Arg Ala Lys Asn Phe Ala Glu Leu Val Leu Ser Asp Lys Val Gln
485                 490                 495
```

-continued

| | | | | | | | | | | | | | | | | |
|---|---|---|---|---|---|---|---|---|---|---|---|---|---|---|---|---|
| ttt | tgt | tat | ttc | cct | tca | act | att | gca | gct | gcg | gtt | gtc | atc | ttg | gcg | 4460 |
| Phe | Cys | Tyr | Phe | Pro | Ser | Thr | Ile | Ala | Ala | Ala | Val | Val | Ile | Leu | Ala | |
| 500 | | | | 505 | | | | | 510 | | | | | | | |

| | | | | | | | | | | | | | | | | |
|---|---|---|---|---|---|---|---|---|---|---|---|---|---|---|---|---|
| tcc | cta | gga | gaa | aaa | caa | gat | gca | cca | agt | caa | cga | gtc | att | gag | gta | 4508 |
| Ser | Leu | Gly | Glu | Lys | Gln | Asp | Ala | Pro | Ser | Gln | Arg | Val | Ile | Glu | Val | |
| 515 | | | | | 520 | | | | | 525 | | | | | 530 | |

| | | | | | | | | | | | | | | | | |
|---|---|---|---|---|---|---|---|---|---|---|---|---|---|---|---|---|
| cat | aaa | tac | aaa | tac | ctg | tta | gag | aga | aaa | ctc | ctt | tat | ctt | tat | att | 4556 |
| His | Lys | Tyr | Lys | Tyr | Leu | Leu | Glu | Arg | Lys | Leu | Leu | Tyr | Leu | Tyr | Ile | |
| | | | | 535 | | | | | 540 | | | | | 545 | | |

| | | | | | | | | | | | | | | | | |
|---|---|---|---|---|---|---|---|---|---|---|---|---|---|---|---|---|
| gac | cca | att | gaa | caa | ata | aac | aag | tat | ttt | gaa | atc | gag | aag | aaa | ctt | 4604 |
| Asp | Pro | Ile | Glu | Gln | Ile | Asn | Lys | Tyr | Phe | Glu | Ile | Glu | Lys | Lys | Leu | |
| | | | | 550 | | | | | 555 | | | | | 560 | | |

| | | | | |
|---|---|---|---|---|
| taa agttttacaa | aaacaccata | atctaaatcc | aattagattc | aactgtaatg | 4657 |
| taaagtacaa | taataaaata | catataccat | aaggaaatgg | taggttatag tgtttgtttc | 4717 |
| aattagatat | tcaatttata | tattagttag | tgttgttaat | ctccctgaat atttcttact | 4777 |
| aacttgagga | aggtctcctg | tcttctggaa | acccttccat | gcccaaaatt tcagccttct | 4837 |
| gctattccca | ttaagtcaaa | catgtaatga | gtttactttt | ctttctcctt ctaattatta | 4897 |
| attatttta | ataatttatt | tgtctaattc | attttctgta | gtctgaaccc acgaacttgc | 4957 |
| ttatcacaaa | atccaaaacc | aaaaacccca | tcacaatttt | ggaaatcttt ttgagaactg | 5017 |
| ctactataac | catgtaattt | ctttcaaaat | ctacaaaaat | agaaataaca cttatttaga | 5077 |
| ctatctgtgg | tactatctca | taacatctgg | tgcattgtgg | ctttgcagac gcatgtca | 5135 |

<210> SEQ ID NO 26
<211> LENGTH: 562
<212> TYPE: PRT
<213> ORGANISM: Citrullus lanatus

<400> SEQUENCE: 26

Met Lys Ser Lys Lys Pro Arg Ala Asn Pro Lys Pro Glu Ser Tyr Ser
1               5                   10                  15

Pro Pro Lys Lys Lys Leu Arg Ser Gln Leu Pro Arg Arg Arg Arg Ser
            20                  25                  30

Arg Ile Ser Pro Phe Phe Cys Ser Leu Asp Ser Asp Ser Pro Ala Pro
        35                  40                  45

Ser Thr Thr Ile Ala Phe Ala Ser Ser Ser Phe Ala Ala Ala Glu Ser
    50                  55                  60

Ser Ser Thr Ser Phe His Ala Gly Gly Pro Glu Val Ser Ser Gln Leu
65                  70                  75                  80

Asn Ala Cys Phe Gly Phe Gln Arg Pro Asn Leu Arg Lys Arg Arg Phe
                85                  90                  95

Gly Ser Gly Gly Val Asn Leu Asp Glu Val Ser Lys Lys Glu Val Gly
            100                 105                 110

Val Gly Ser Asn Val Glu Val Ser Glu Ser Ser Cys Val Glu Ser Asn
        115                 120                 125

Ser Gly Val Asp Phe Gly Val Leu Gly Pro Ser Thr Ser Ser Arg Leu
    130                 135                 140

Lys Ile Arg Ser Asp Phe Arg Arg Thr Ile Asp Glu Asn Glu Asp Pro
145                 150                 155                 160

Ile Asp Gln Ala Asp Asn Gly Val Val Lys Phe Gln Leu Thr Asp Ala
                165                 170                 175

Asp Val Ser Ser Lys Leu Cys Glu Lys Gly Ala Val Pro Leu Thr Pro
            180                 185                 190

Cys Gly Glu Ser Cys Ala Glu Ser Ile Phe Gln Ser Val Cys Ser Phe
            195                 200                 205

Glu Glu Lys Gly Leu Asp Val Glu Glu Asn Arg Leu Trp Glu Phe Gln
210                 215                 220

Leu Pro Glu Leu Pro Arg Asn Glu Ile Asn Glu Thr Phe Thr Val Ser
225                 230                 235                 240

Lys Ser Asp Ser Thr Ile Glu Gln Trp Pro Asn Ser Leu Lys Phe Glu
            245                 250                 255

Ser Asp Leu Ala Cys Thr Glu Gln Phe Ser Tyr Glu Asn Val Ser Glu
            260                 265                 270

Tyr Ser Ser Gln Ala Leu Ser Glu Leu Gln Ser Thr Ile Leu Leu Glu
            275                 280                 285

Thr Ser Asp Thr Asp Cys Ser Asp Tyr Thr Pro Ser Ile Phe Leu Glu
290                 295                 300

Ser Gly Ser Glu Phe Ser Glu Lys Ser Asn Asp Ala Ala Pro Ser
305                 310                 315                 320

Ser Thr Phe Ser Met Leu Leu Gln Tyr Arg Arg Asp Phe Leu Asn Leu
            325                 330                 335

Asn Ala Ser Pro Asp Ile Arg Thr Ser Ser Ile Glu Glu Glu Lys
            340                 345                 350

Val Asp Gln Ser Thr Ile Leu Arg Phe Glu Glu Leu Asp Asp Glu Glu
            355                 360                 365

Ala Tyr Leu Met Phe Arg Ser Arg Glu Arg Arg Gln Leu Ile Ile Arg
            370                 375                 380

Asp Tyr Val Glu Glu Tyr Arg Ser Thr Thr Asp Tyr Gly Asp Leu Ile
385                 390                 395                 400

Leu Gln Gln Arg Ser Asn Val Val Gln Trp Ile Val Glu Arg Ser Arg
            405                 410                 415

Asp Ser Lys Leu His Gln Glu Thr Thr Phe Leu Gly Val Thr Leu Leu
            420                 425                 430

Asp Gln Ile Leu Ser Arg Gly Phe Phe Lys Ala Gly Arg His Leu Gln
            435                 440                 445

Ile Leu Gly Ile Ala Cys Leu Thr Leu Ala Thr Arg Ile Glu Glu Asn
450                 455                 460

Gln Ser Tyr Ser Trp Phe Tyr Leu Lys Ala Ala Gly Ala Asp Ser Asn
465                 470                 475                 480

Leu Glu Asn Arg Ala Lys Asn Phe Ala Glu Leu Val Leu Ser Asp Lys
            485                 490                 495

Val Gln Phe Cys Tyr Phe Pro Ser Thr Ile Ala Ala Val Val Ile
            500                 505                 510

Leu Ala Ser Leu Gly Glu Lys Gln Asp Ala Pro Ser Gln Arg Val Ile
            515                 520                 525

Glu Val His Lys Tyr Lys Tyr Leu Leu Glu Arg Lys Leu Leu Tyr Leu
530                 535                 540

Tyr Ile Asp Pro Ile Glu Gln Ile Asn Lys Tyr Phe Glu Ile Glu Lys
545                 550                 555                 560

Lys Leu

<210> SEQ ID NO 27
<211> LENGTH: 1673
<212> TYPE: RNA
<213> ORGANISM: Artificial Sequence
<220> FEATURE:
<223> OTHER INFORMATION: Induced by mutation
<220> FEATURE:

```
<221> NAME/KEY: mRNA
<222> LOCATION: (1)..(1673)
<220> FEATURE:
<221> NAME/KEY: CDS
<222> LOCATION: (1)..(1098)

<400> SEQUENCE: 27 aug aag ucc aag aag cca agg gca aau ccc aaa ccc gaa ucc uac ucu        48
Met Lys Ser Lys Lys Pro Arg Ala Asn Pro Lys Pro Glu Ser Tyr Ser
1               5                   10                  15 ccg ccg aag aag aag cuc cgu ucu cag cuu cca cgc aga cgc ucu            96
Pro Pro Lys Lys Lys Leu Arg Ser Gln Leu Pro Arg Arg Arg Ser
            20                  25                  30 cgg auu ucu ccu uuu uuc ugc ucc uug gac ucc gau ucc ccu gcu ccu       144
Arg Ile Ser Pro Phe Phe Cys Ser Leu Asp Ser Asp Ser Pro Ala Pro
        35                  40                  45 ucu acc acc auu gcu uuu gcu ucu ucc uuu gcu gcc gcc gaa ucc           192
Ser Thr Thr Ile Ala Phe Ala Ser Ser Phe Ala Ala Ala Glu Ser
    50                  55                  60 agc ucc acu ucc uuc cac gca ggc gga ccu gag guu ucu agc cag cuc       240
Ser Ser Thr Ser Phe His Ala Gly Gly Pro Glu Val Ser Ser Gln Leu
65                  70                  75                  80 aac gcg ugu uuu gga uuc cag agg cca aau uug cgg aag aga cga uuu       288
Asn Ala Cys Phe Gly Phe Gln Arg Pro Asn Leu Arg Lys Arg Arg Phe
                85                  90                  95 ggu ucg ggu ggu guu aau uug gau gaa guu ucg aag aag gag guu gga       336
Gly Ser Gly Gly Val Asn Leu Asp Glu Val Ser Lys Lys Glu Val Gly
            100                 105                 110 gua ggg agu aau gug gaa gug ucu gaa ucg ucu ugc guu gaa uca aau       384
Val Gly Ser Asn Val Glu Val Ser Glu Ser Ser Cys Val Glu Ser Asn
        115                 120                 125 ucu gga guu gau uuu ggu guu cuc gga cca agc acu agc ucc agg uug       432
Ser Gly Val Asp Phe Gly Val Leu Gly Pro Ser Thr Ser Ser Arg Leu
    130                 135                 140 aag auu aga agu gau uuu agg aga acu auu gac gaa aau gaa gau cca       480
Lys Ile Arg Ser Asp Phe Arg Arg Thr Ile Asp Glu Asn Glu Asp Pro
145                 150                 155                 160 auc gau caa gcg gau aau gga guu gug aag uuu caa uug acg gau gcu       528
Ile Asp Gln Ala Asp Asn Gly Val Val Lys Phe Gln Leu Thr Asp Ala
                165                 170                 175 gau guc ucg ucg aag cuu ugu gaa aag gga gcu gug cca cuc acu ccu       576
Asp Val Ser Ser Lys Leu Cys Glu Lys Gly Ala Val Pro Leu Thr Pro
            180                 185                 190 ugu gga gag ucu ugc gcu gag ucu auc uuc cag agc guu ugu ucg uuc       624
Cys Gly Glu Ser Cys Ala Glu Ser Ile Phe Gln Ser Val Cys Ser Phe
        195                 200                 205 gaa gag aaa gga uua gac guu gaa gaa aac aga cua ugg gaa uuu cag       672
Glu Glu Lys Gly Leu Asp Val Glu Glu Asn Arg Leu Trp Glu Phe Gln
    210                 215                 220 uua cca gaa cua ccg aga aau gag auc aau gaa acu uuc acu guu ucg       720
Leu Pro Glu Leu Pro Arg Asn Glu Ile Asn Glu Thr Phe Thr Val Ser
225                 230                 235                 240 aag ucg gau ucg acg aua gaa cag ugg ccu aau agc uug aag uuu gaa       768
Lys Ser Asp Ser Thr Ile Glu Gln Trp Pro Asn Ser Leu Lys Phe Glu
                245                 250                 255 ucg gau cuu gcu ugc acg gag caa uuc ucu uau gag aau guu ucg gaa       816
Ser Asp Leu Ala Cys Thr Glu Gln Phe Ser Tyr Glu Asn Val Ser Glu
            260                 265                 270 uac ucu agc cag gcg uug ucc gag cuu caa uca aca auu cua uug gag       864
Tyr Ser Ser Gln Ala Leu Ser Glu Leu Gln Ser Thr Ile Leu Leu Glu
        275                 280                 285
```

```
acg ucu gau acu gac ugc uca gau uac acu ccu uca auu uuu uug gaa      912
Thr Ser Asp Thr Asp Cys Ser Asp Tyr Thr Pro Ser Ile Phe Leu Glu
    290                 295                 300
ucc gga agc gaa uuu uca gag aaa ucg aac gac gac gca gcu ccu ucg      960
Ser Gly Ser Glu Phe Ser Glu Lys Ser Asn Asp Asp Ala Ala Pro Ser
305                 310                 315                 320
uca aca uuu agc aug uug cug cag uac aga cgc gac uuu cua aac uua     1008
Ser Thr Phe Ser Met Leu Leu Gln Tyr Arg Arg Asp Phe Leu Asn Leu
                325                 330                 335
aau gcc ucu cca gac auc aga acu agc ucg ucu auu gaa gaa gag aaa     1056
Asn Ala Ser Pro Asp Ile Arg Thr Ser Ser Ser Ile Glu Glu Glu Lys
            340                 345                 350
gua gau caa ucu acg aau ugg acg aug aag aag ccu auc uaa             1098
Val Asp Gln Ser Thr Asn Trp Thr Met Lys Lys Pro Ile
        355                 360                 365
uguucagaag uagagaaaga cgccaauuga uuauucgcga cuacguagag gaguaucggu   1158
ccacaacgga uuauggcgau cucauucucc agcaacgguc aaaugugguc caauggauag   1218
uugaacgauc gagagauucc aaacuucauc aggagacgac auuuuuagga guuacccucc   1278
uggaccagau ucugagcaga ggauucuuca aagcuggaag acaccuucaa auucugggca   1338
uagcaugucu aacuuuggcg acuagaauug aagaaaauca gucauacagc ugguucuacc   1398
ugaaagcugc uggagcugac ucgaauuugg agaaucgagc uaagaacuuu gcggagcugg   1458
uucuuucaga caaaguccaa uuuuguuauu ucccuucaac uauugcagcu gcgguuguca   1518
ucuuggcguc ccuaggagaa aaacaagaug caccaaguca acgagucauu gagguacaua   1578
aauacaaaua ccuguuagag agaaaacucc uuuaucuuua uauugaccca auugaacaaa   1638
uaaacaagua uuuugaaauc gagaagaaac uuuaa                               1673

<210> SEQ ID NO 28
<211> LENGTH: 365
<212> TYPE: PRT
<213> ORGANISM: Artificial Sequence
<220> FEATURE:
<223> OTHER INFORMATION: Synthetic Construct

<400> SEQUENCE: 28

Met Lys Ser Lys Lys Pro Arg Ala Asn Pro Lys Pro Glu Ser Tyr Ser
1               5                   10                  15

Pro Pro Lys Lys Lys Leu Arg Ser Gln Leu Pro Arg Arg Arg Arg Ser
            20                  25                  30

Arg Ile Ser Pro Phe Phe Cys Ser Leu Asp Ser Asp Ser Pro Ala Pro
        35                  40                  45

Ser Thr Thr Ile Ala Phe Ala Ser Ser Ser Phe Ala Ala Ala Glu Ser
    50                  55                  60

Ser Ser Thr Ser Phe His Ala Gly Gly Pro Glu Val Ser Ser Gln Leu
65                  70                  75                  80

Asn Ala Cys Phe Gly Phe Gln Arg Pro Asn Leu Arg Lys Arg Arg Phe
                85                  90                  95

Gly Ser Gly Gly Val Asn Leu Asp Glu Val Ser Lys Lys Glu Val Gly
            100                 105                 110

Val Gly Ser Asn Val Glu Val Ser Glu Ser Ser Cys Val Glu Ser Asn
        115                 120                 125

Ser Gly Val Asp Phe Gly Val Leu Gly Pro Ser Thr Ser Ser Arg Leu
    130                 135                 140

Lys Ile Arg Ser Asp Phe Arg Arg Thr Ile Asp Glu Asn Glu Asp Pro
```

```
                145                 150                 155                 160
Ile Asp Gln Ala Asp Asn Gly Val Val Lys Phe Gln Leu Thr Asp Ala
                    165                 170                 175

Asp Val Ser Ser Lys Leu Cys Glu Lys Gly Ala Val Pro Leu Thr Pro
                    180                 185                 190

Cys Gly Glu Ser Cys Ala Glu Ser Ile Phe Gln Ser Val Cys Ser Phe
                    195                 200                 205

Glu Glu Lys Gly Leu Asp Val Glu Glu Asn Arg Leu Trp Glu Phe Gln
        210                 215                 220

Leu Pro Glu Leu Pro Arg Asn Glu Ile Asn Glu Thr Phe Thr Val Ser
225                 230                 235                 240

Lys Ser Asp Ser Thr Ile Glu Gln Trp Pro Asn Ser Leu Lys Phe Glu
                245                 250                 255

Ser Asp Leu Ala Cys Thr Glu Gln Phe Ser Tyr Glu Asn Val Ser Glu
                260                 265                 270

Tyr Ser Ser Gln Ala Leu Ser Glu Leu Gln Ser Thr Ile Leu Leu Glu
            275                 280                 285

Thr Ser Asp Thr Asp Cys Ser Asp Tyr Thr Pro Ser Ile Phe Leu Glu
        290                 295                 300

Ser Gly Ser Glu Phe Ser Glu Lys Ser Asn Asp Asp Ala Ala Pro Ser
305                 310                 315                 320

Ser Thr Phe Ser Met Leu Leu Gln Tyr Arg Arg Asp Phe Leu Asn Leu
                325                 330                 335

Asn Ala Ser Pro Asp Ile Arg Thr Ser Ser Ser Ile Glu Glu Glu Lys
            340                 345                 350

Val Asp Gln Ser Thr Asn Trp Thr Met Lys Lys Pro Ile
        355                 360                 365

<210> SEQ ID NO 29
<211> LENGTH: 151
<212> TYPE: DNA
<213> ORGANISM: Citrullus lanatus

<400> SEQUENCE: 29
attggtttgt gactcggatt cagaggaatt gttattggaa gagaagctat catttatgca      60
tgaaacgagg catgcattcg gaaggactgc cctgctctta agtggaggtg cttcacttgg     120
agcttttcat acaggagttg tcaaaactct g                                    151

<210> SEQ ID NO 30
<211> LENGTH: 906
<212> TYPE: DNA
<213> ORGANISM: Citrullus lanatus

<400> SEQUENCE: 30
atgagggaag aacactcgaa ttggttctct aggtgggaag aggagcttcc atctccagat      60
gaattgatgc tcctttctca aaccctaata accccgatc tagctttggc ctttgatatt     120
cagaatccca gcaatagcag tccgccgttg ccttgtccat ctccgccgct ttcgaatcct     180
ctgcctggct ctggcaacgg aattgcgcag cccaactcgg cggatttcgg cgattctgcc     240
gatttgggct ccggcgccgc cagcgacgag ccggctcgga ccctcaagcg accacgcctt     300
gtttggacgc ctcagctcca caagcgattc gtcgatgctg ttgctcattt agggataaaa     360
aatgccgtcc ccaagaccat aatgcagctc atgagtgtcg atggcttgac ccagagaaac     420
gtagctaacc atttgcagaa gtaccgcctc tatctcaagc ggatgcaggg gttgtcctcc     480
```

-continued

```
ggcggcggcg gtggtggtgg tggcttggtt gcttcctccg atcccgccac tgaccatttg    540
tttgccagct ccccagttcc accccatttg cttcactctg ctcgcaccag ttcagaccat    600
ttcttgccct ttgttcccat ggccactctg cagcagcacc accatcacca gcagcagatg    660
gccgctgctg ctgctgtcgc cgtccatccg cagctccagc cgccttatca tcggcaggtc    720
gggcatttcg ggtcaccgcc gaatggccag tttgagcatc catttttagc tagacagtcc    780
cagcctatcc atagaatggg agcaccagtg cctaattcag ttcctaatta catagaggat    840
ttggaatcag ccaatgccag tgaggaagaa aaagttctca ccttatttcc tactggggat    900
gattga    906
```

<210> SEQ ID NO 31
<211> LENGTH: 301
<212> TYPE: PRT
<213> ORGANISM: artificial
<220> FEATURE:
<223> OTHER INFORMATION: Citrullus lanatus mutant wop1 protein

<400> SEQUENCE: 31

```
Met Arg Glu Glu His Ser Asn Trp Phe Ser Arg Trp Glu Glu Glu Leu
1               5                   10                  15

Pro Ser Pro Asp Glu Leu Met Pro Leu Ser Gln Thr Leu Ile Thr Pro
            20                  25                  30

Asp Leu Ala Leu Ala Phe Asp Ile Gln Asn Pro Ser Asn Ser Ser Pro
        35                  40                  45

Pro Leu Pro Cys Pro Ser Pro Pro Leu Ser Asn Pro Leu Pro Gly Ser
    50                  55                  60

Gly Asn Gly Ile Ala Gln Pro Asn Ser Ala Asp Phe Gly Asp Ser Ala
65                  70                  75                  80

Asp Leu Gly Ser Gly Ala Ala Ser Asp Glu Pro Ala Arg Thr Leu Lys
                85                  90                  95

Arg Pro Arg Leu Val Trp Thr Pro Gln Leu His Lys Arg Phe Val Asp
            100                 105                 110

Ala Val Ala His Leu Gly Ile Lys Asn Ala Val Pro Lys Thr Ile Met
        115                 120                 125

Gln Leu Met Ser Val Asp Gly Leu Thr Arg Glu Asn Val Ala Asn His
    130                 135                 140

Leu Gln Lys Tyr Arg Leu Tyr Leu Lys Arg Met Gln Gly Leu Ser Ser
145                 150                 155                 160

Gly Gly Gly Gly Gly Gly Gly Leu Val Ala Ser Ser Asp Pro Ala
                165                 170                 175

Thr Asp His Leu Phe Ala Ser Ser Pro Val Pro Pro His Leu Leu His
            180                 185                 190

Ser Ala Arg Thr Ser Ser Asp His Phe Leu Pro Phe Val Pro Met Ala
        195                 200                 205

Thr Leu Gln Gln His His His Gln Gln Gln Met Ala Ala Ala Ala
    210                 215                 220

Ala Val Ala Val His Pro Gln Leu Gln Pro Pro Tyr His Arg Gln Val
225                 230                 235                 240

Gly His Phe Gly Ser Pro Pro Asn Gly Gln Phe Glu His Pro Phe Leu
                245                 250                 255

Ala Arg Gln Ser Gln Pro Ile His Arg Met Gly Ala Pro Val Pro Asn
            260                 265                 270

Ser Val Pro Asn Tyr Ile Glu Asp Leu Glu Ser Ala Asn Ala Ser Gly
        275                 280                 285
```

```
Gly Arg Lys Val Leu Thr Leu Phe Pro Thr Gly Asp Asp
        290                 295                 300
```

<210> SEQ ID NO 32
<211> LENGTH: 301
<212> TYPE: PRT
<213> ORGANISM: artificial
<220> FEATURE:
<223> OTHER INFORMATION: Citrullus lanatus wild type WOP1 protein

<400> SEQUENCE: 32

```
Met Arg Glu Glu His Ser Asn Trp Phe Ser Arg Trp Glu Glu Leu
1               5                   10                  15

Pro Ser Pro Asp Glu Leu Met Pro Leu Ser Gln Thr Leu Ile Thr Pro
                20                  25                  30

Asp Leu Ala Leu Ala Phe Asp Ile Gln Asn Pro Ser Asn Ser Ser Pro
            35                  40                  45

Pro Leu Pro Cys Pro Ser Pro Pro Leu Ser Asn Pro Leu Pro Gly Ser
        50                  55                  60

Gly Asn Gly Ile Ala Gln Pro Asn Ser Ala Asp Phe Gly Asp Ser Ala
65              70                  75                  80

Asp Leu Gly Ser Gly Ala Ala Ser Asp Glu Pro Ala Arg Thr Leu Lys
                85                  90                  95

Arg Pro Arg Leu Val Trp Thr Pro Gln Leu His Lys Arg Phe Val Asp
                100                 105                 110

Ala Val Ala His Leu Gly Ile Lys Asn Ala Val Pro Lys Thr Ile Met
            115                 120                 125

Gln Leu Met Ser Val Asp Gly Leu Thr Arg Glu Asn Val Ala Ser His
        130                 135                 140

Leu Gln Lys Tyr Arg Leu Tyr Leu Lys Arg Met Gln Gly Leu Ser Ser
145                 150                 155                 160

Gly Gly Gly Gly Gly Gly Gly Leu Val Ala Ser Ser Asp Pro Ala
                165                 170                 175

Thr Asp His Leu Phe Ala Ser Ser Pro Val Pro Pro His Leu Leu His
            180                 185                 190

Ser Ala Arg Thr Ser Ser Asp His Phe Leu Pro Phe Val Pro Met Ala
        195                 200                 205

Thr Leu Gln Gln His His His Gln Gln Met Ala Ala Ala
        210                 215                 220

Ala Val Ala Val His Pro Gln Leu Gln Pro Pro Tyr His Arg Gln Val
225                 230                 235                 240

Gly His Phe Gly Ser Pro Pro Asn Gly Gln Phe Glu His Pro Phe Leu
                245                 250                 255

Ala Arg Gln Ser Gln Pro Ile His Arg Met Gly Ala Pro Val Pro Asn
            260                 265                 270

Ser Val Pro Asn Tyr Ile Glu Asp Leu Glu Ser Ala Asn Ala Ser Gly
        275                 280                 285

Gly Arg Lys Val Leu Thr Leu Phe Pro Thr Gly Asp Asp
        290                 295                 300
```

<210> SEQ ID NO 33
<211> LENGTH: 301
<212> TYPE: PRT
<213> ORGANISM: Cucumis sativus

<400> SEQUENCE: 33

```
Met Arg Glu Glu His Ser Asn Trp Phe Ser Arg Trp Glu Asp Glu Leu
1               5                   10                  15

Pro Ser Pro Asp Glu Leu Met Pro Leu Ser Gln Thr Leu Ile Thr Pro
            20                  25                  30

Asp Leu Ala Leu Ala Phe Asp Ile Gln Asn Pro Ser Asn Ser Ser Pro
            35                  40                  45

Pro Leu Pro Cys Pro Ser Pro Pro Leu Ser Asn Pro Leu Pro Gly Ser
        50                  55                  60

Gly Asn Gly Ile Val Pro Asn Ser Ala Asp Phe Gly Asp Ser Ala
65                  70                  75                  80

Asp Leu Gly Ser Gly Ala Ala Ser Asp Glu Pro Ala Arg Thr Leu Lys
                85                  90                  95

Arg Pro Arg Leu Val Trp Thr Pro Gln Leu His Lys Arg Phe Val Asp
            100                 105                 110

Ala Val Ala His Leu Gly Ile Lys Asn Ala Val Pro Lys Thr Ile Met
            115                 120                 125

Gln Leu Met Ser Val Asp Gly Leu Thr Arg Glu Asn Val Ala Ser His
        130                 135                 140

Leu Gln Lys Tyr Arg Leu Tyr Leu Lys Arg Met Gln Gly Leu Ser Gly
145                 150                 155                 160

Gly Gly Gly Gly Gly Ala Ala Leu Val Gly Ser Ser Asp Pro Ala
                165                 170                 175

Thr Asp His Leu Phe Ala Ser Ser Pro Val Pro His Leu Leu His
            180                 185                 190

Ser Ala Arg Thr Ser Ser Asp His Phe Leu Pro Tyr Val Pro Met Ala
            195                 200                 205

Thr Leu Gln Gln His His His His Gln Gln Gln Met Ala Ala Ala Ala
        210                 215                 220

Ala Val Ala Gly His Thr Gln Leu Gln Pro Pro Tyr His Arg Gln Val
225                 230                 235                 240

Gly His Phe Gly Ser Pro Pro Asn Gly Gln Phe Glu His Pro Phe Leu
            245                 250                 255

Ala Arg Gln Ser Gln Pro Ile His Arg Met Gly Thr Pro Val His Asn
            260                 265                 270

Ser Val Pro Asn Tyr Ile Glu Asp Leu Glu Ser Ala Asn Ala Thr Gly
            275                 280                 285

Gly Arg Lys Val Leu Thr Leu Phe Pro Thr Gly Asp Asp
            290                 295                 300

<210> SEQ ID NO 34
<211> LENGTH: 301
<212> TYPE: PRT
<213> ORGANISM: Cucumis melo

<400> SEQUENCE: 34

Met Arg Glu Glu His Ser Asn Trp Phe Ser Arg Trp Glu Glu Leu
1               5                   10                  15

Pro Ser Pro Asp Glu Leu Met Pro Leu Ser Gln Thr Leu Ile Thr Pro
            20                  25                  30

Asp Leu Ala Leu Ala Phe Asp Ile Gln Asn Pro Ser Asn Ser Ser Pro
            35                  40                  45

Pro Leu Pro Cys Pro Ser Pro Pro Leu Ser Asn Pro Leu Pro Gly Ser
        50                  55                  60

Gly Asn Gly Ile Val Pro Pro Asn Ser Ala Asp Phe Gly Asp Ser Ala
65                  70                  75                  80
```

```
Asp Leu Gly Ser Gly Ala Ala Ser Asp Glu Pro Ala Arg Thr Leu Lys
                85                  90                  95

Arg Pro Arg Leu Val Trp Thr Pro Gln Leu His Lys Arg Phe Val Asp
            100                 105                 110

Ala Val Ala His Leu Gly Ile Lys Asn Ala Val Pro Lys Thr Ile Met
        115                 120                 125

Gln Leu Met Ser Val Asp Gly Leu Thr Arg Glu Asn Val Ala Ser His
    130                 135                 140

Leu Gln Lys Tyr Arg Leu Tyr Leu Lys Arg Met Gln Gly Leu Ser Gly
145                 150                 155                 160

Gly Gly Ala Gly Gly Ala Ala Leu Val Gly Ser Ser Asp Pro Ala
                165                 170                 175

Thr Asp His Leu Phe Ala Ser Ser Pro Val Pro Pro His Leu Leu His
            180                 185                 190

Ser Ala Arg Thr Ser Ser Asp His Phe Leu Pro Phe Val Pro Met Ala
        195                 200                 205

Thr Leu Gln Gln His His His Gln Gln Gln Met Ala Ala Ala Ala
    210                 215                 220

Ala Val Ala Gly His Thr Gln Leu Gln Pro Pro Tyr His Arg Gln Val
225                 230                 235                 240

Gly His Phe Gly Ser Pro Pro Asn Gly Gln Phe Glu His Pro Phe Leu
                245                 250                 255

Ala Arg Gln Ser Gln Pro Ile His Arg Met Gly Thr Ser Val His Asn
            260                 265                 270

Ser Val Pro Asn Tyr Ile Glu Asp Leu Glu Ser Ala Asn Ala Thr Gly
        275                 280                 285

Gly Arg Lys Val Leu Thr Leu Phe Pro Thr Gly Asp Asp
    290                 295                 300

<210> SEQ ID NO 35
<211> LENGTH: 54
<212> TYPE: PRT
<213> ORGANISM: artificial
<220> FEATURE:
<223> OTHER INFORMATION: myb-like DNA binding domain SHAQKYF

<400> SEQUENCE: 35

Arg Pro Arg Leu Val Trp Thr Pro Gln Leu His Lys Arg Phe Val Asp
1               5                   10                  15

Ala Val Ala His Leu Gly Ile Lys Asn Ala Val Pro Lys Thr Ile Met
            20                  25                  30

Gln Leu Met Ser Val Asp Gly Leu Thr Arg Glu Asn Val Ala Ser His
        35                  40                  45

Leu Gln Lys Tyr Arg Leu
    50

<210> SEQ ID NO 36
<211> LENGTH: 39
<212> TYPE: DNA
<213> ORGANISM: artificial
<220> FEATURE:
<223> OTHER INFORMATION: PCR primer

<400> SEQUENCE: 36
cctacacgac gctcttccaa gaggagcttc catctccag                          39

<210> SEQ ID NO 37
```

```
<211> LENGTH: 37
<212> TYPE: DNA
<213> ORGANISM: artificial
<220> FEATURE:
<223> OTHER INFORMATION: PCR primer

<400> SEQUENCE: 37
ctgctgaacc gctcttccag cccaaatcgg cagaatc                                37

<210> SEQ ID NO 38
<211> LENGTH: 213
<212> TYPE: DNA
<213> ORGANISM: artificial
<220> FEATURE:
<223> OTHER INFORMATION: amplified fragment

<400> SEQUENCE: 38
aagaggagct tccatctcca gatgaattga tgcctctttc tcaaaccta ataacccccg        60 atctagcttt ggcctttgat attcagaatc ccagcaatag cagtccgccg ttgccttgtc      120
catctccgcc gctttcgaat cctctgcctg gctctggcaa cggaattgcg cagcccaact      180
cggcggattt cggcgattct gccgatttgg gct                                    213

<210> SEQ ID NO 39
<211> LENGTH: 37
<212> TYPE: DNA
<213> ORGANISM: artificial
<220> FEATURE:
<223> OTHER INFORMATION: PCR primer

<400> SEQUENCE: 39
cctacacgac gctcttccgt ggcttggttg cttcctc                                37

<210> SEQ ID NO 40
<211> LENGTH: 37
<212> TYPE: DNA
<213> ORGANISM: artificial
<220> FEATURE:
<223> OTHER INFORMATION: PCR primer

<400> SEQUENCE: 40
ctgctgaacc gctcttccga tgataaggcg gctggag                                37

<210> SEQ ID NO 41
<211> LENGTH: 213
<212> TYPE: DNA
<213> ORGANISM: artificial
<220> FEATURE:
<223> OTHER INFORMATION: ampliefied PCR fragment

<400> SEQUENCE: 41
gtggcttggt tgcttcctcc gatcccgcca ctgaccattt gtttgccagc tccccagttc       60
caccccattt gcttcactct gctcgcacca gttcagacca tttcttgccc tttgttccca      120
tggccactct gcagcagcac caccatcacc agcagcagat ggccgctgct gctgctgtcg      180
ccgtccatcc gcagctccag ccgccttatc atc                                    213
```